United States Patent
Beck et al.

(10) Patent No.: US 11,912,692 B2
(45) Date of Patent: Feb. 27, 2024

(54) SUBSTITUTED S-ALANINATE DERIVATIVES

(71) Applicant: BAYER AKTIENGESELLSCHAFT, Leverkusen (DE)

(72) Inventors: Hartmut Beck, Wuppertal (DE); Stefanie Mesch, Basel (CH); Alexandros Vakalopoulos, Hilden (DE); Nils Pfaff, Düsseldorf (DE); Stefanie Zimmermann, Düsseldorf (DE); Markus Follmann, Köin (DE); Elisabeth Kersten, Wuppertal (DE); Guillaume Levilain, Wuppertal (DE); Kartrin Partikel, Wuppertal (DE); Andreas Peter Broehl, Wuppertal (DE); Stefan Heitmeier, Wülfrath (DE); Julia Dietze-Torres, Wuppertal (DE); Lutz Lehmann, Berlin (DE); Kersten Matthias Gericke, Wuppertal (DE); Frank Süßmeier, Munich (DE); Lars Bärfacker, Düsseldorf (DE); Alexander Hillisch, Solingen (DE); Adrian Tersteegen, Wuppertal (DE); Anja Buchmüller, Essen (DE); Christoph Gerdes, Cologne (DE)

(73) Assignee: Bayer Aktiengesellschaft, Leverkusen (DE)

(*) Notice: Subject to any disclaimer, the term of this patent is extended or adjusted under 35 U.S.C. 154(b) by 0 days.

(21) Appl. No.: 18/233,031

(22) Filed: Aug. 11, 2023

(65) Prior Publication Data

US 2023/0391761 A1    Dec. 7, 2023

Related U.S. Application Data

(63) Continuation of application No. PCT/EP2022/073889, filed on Aug. 29, 2022.

(30) Foreign Application Priority Data

Sep. 3, 2021 (EP) .................... 21194781

(51) Int. Cl.
  C07D 409/14   (2006.01)
  A61P 7/02     (2006.01)

(52) U.S. Cl.
  CPC .............. *C07D 409/14* (2013.01); *A61P 7/02* (2018.01)

(58) Field of Classification Search
  CPC .............. A61K 31/381; A61K 31/4015; A61K 31/402; A61K 31/4025; A61K 31/4178; A61P 7/02; C07D 409/14
  See application file for complete search history.

(56) References Cited

FOREIGN PATENT DOCUMENTS

| WO | 2009103440 A1 | 8/2009 |
| WO | 2014174102 A1 | 10/2014 |

OTHER PUBLICATIONS

Atlenburger, Jean-Michel, et al., "SSR182289A, a selective and potent orally active thrombin inhibitor", Bioorganic & Medicinal Chemistry, 2004, pp. 1713-1730, vol. 12.

Berry, et al., "Antithrombotic actions of argatroban in rat models of venous, 'mixed' and arterial thrombosis, and its effect on the tail transection bleeding time", Br. J. Pharmacol., 1994, pp. 1209-1214, vol. 113.

International Search Report from PCT Application No. PCT/EP2022/073889, dated Nov. 18, 2022.

Meneyrol, Jerome, et al., "5-Chlorothiophene-2-carboxylic Acid [(S)-2-[2-Methyl-3-(2-oxopyrrolidin-1-yl) benzenesulfonylamino]-3-(4-methylpiperazin-1-yl)-3-oxopropyl]amide (SAR107375), a Selective and Potent Orally Active Dual Thrombin and Factor Xa Inhibitor", Journal of Medicinal Chemistry, 2013, pp. 9441-9456, vol. 56.

Written Opinion from PCT Application No. PCT/EP2022/073889, dated Nov. 18, 2022.

*Primary Examiner* — Theodore R. Howell

(57) ABSTRACT

The invention relates to substituted S-alaninate derivatives and to processes for their preparation, and also to their use for preparing medicaments for the treatment and/or prophylaxis of diseases, in particular vascular disorders, preferably thrombotic or thromboembolic disorders and/or thrombotic or thromboembolic complications.

17 Claims, 5 Drawing Sheets

SUBSTITUTED S-ALANINATE DERIVATIVES

CROSS REFERENCE TO RELATED APPLICATION

This application is a continuation of PCT International Application No. PCT/EP2022/073889, filed Aug. 29, 2022, which claims the benefit from the earlier filed foreign application, EP Application No. 21194781.7, filed Sep. 3, 2021 and is hereby incorporated into this application by reference as if fully set forth herein.

The invention relates to substituted S-alaninate derivatives and to processes for their preparation, and also to their use for preparing medicaments for the treatment and/or prophylaxis of diseases, in particular vascular disorders, preferably thrombotic or thromboembolic disorders and/or thrombotic or thromboembolic complications.

Haemostasis is the crucial mechanism to protect organisms from excessive and potentially life-threatening blood losses after injury, which closes leakages in the arterial or venous vessel wall quickly and reliably with a clot mainly formed of a net of fibrin and platelets. Fibrin formation is initiated at the site of injury, when subendothelial tissue factor is exposed to blood after endothelial cell damage and triggers a waterfall cascade of complex enzymatic reactions, in which an activated blood coagulation factor converts the next zymogen into its active protease form. Traditionally, the early steps of the cascade are divided into the extrinsic (or tissue factor) pathway and the intrinsic (or contact activation) pathway, depending on whether the trigger might be tissue factor bound to various cell types or factor XII activated on negatively charged surfaces. Both pathways converge at the level of factor X activation, which is the key enzyme of thrombin generation. Finally, via transformation of a number of substrates thrombin translates the signals generated in the cascade to the coagulation state of the blood: Thrombin cleaves fibrinogen thereby leads to the generation of the fibrin net, it activates factor XIII to XIIIa, which is required for clot stabilization. In addition, thrombin is a potent trigger of platelet aggregation (via PAR-1 activation), which also contributes considerably to clot formation. By activating TAFI (thrombin-activatable fibrinolysis inhibitor) to TAFIa in a complex with thrombomodulin, thrombin inhibits the dissolution of the clot. In positive feedback loops, activation of the factors V, VIII and XI potentiates the production of thrombin and thus amplifies the coagulation reaction. Contrarily, activation of protein C by the thrombin/thrombomodulin complex leads to degradation of factor VIIIa in tenase complexes and factor Va in prothrombinase complexes—and thereby reduces further thrombin generation.

The coagulation factors often exist in complexes on surfaces, e.g. factor Xa is bound in the prothrombinase complex with factor Va. During the formation of a fibrin clot, thrombin and the prothrombinase are integrated and bound in the fibrin net. These enzyme molecules remain active and difficult to reach by endogenous anticoagulants, e.g. antithrombin III.

Haemostasis is subject to a complex regulatory mechanism between clot formation and dissolution. While coverage of a vessel wall leakage is an essential procedure to prevent bleedings, excessive clot formation caused by vessel wall disorders, like atherosclerotic lesions, ongoing inflammatory processes in the blood, like in the course of infections, or reductions in blood flow may result in vessel occlusions, which lead to events of great danger for the surrounding tissues, because the supply with nutrients and the clearance of potentially harmful degradation products is hampered. These clots can block veins, arteries or lymph vessels at the site of generation or may travel as emboli through the vessels, until they get stuck. Many of these thrombi are formed following local vessel disorders, e.g. rupture of atherosclerotic plaques or blood flow deficiencies in deep veins. These may lead to severe events, which can occur in any vessel, including stroke, myocardial infarction or pulmonary embolism, which are among the leading causes of death. In other cases, tissue factor exposure on blood cells, e.g. on monocytes in the course of infections, or exposure of negatively charged surfaces or macromolecules to factor XII, e.g. after cell death, may lead to a system-wide hypercoagulable state, resulting in microthrombotic disorders with potential subsequent organ damage. These hypercoagulable states may be caused for example by infections with bacteria, viruses or fungi or by trauma.

In addition, systemic hypercoagulation may lead to consumptive coagulopathies in the context of a disseminated intravascular coagulopathy (DIC). Thromboembolic complications are furthermore encountered in microangiopathic haemolytic anaemias, extracorporeal circulatory procedures, such as haemodialysis, in cardiac cavities, at prosthetic heart valves and stents, and during transplantations.

Anticoagulant drugs are used in the prophylactic setting to prevent thrombus formation and during acute thrombotic/embolic events to support the lysis of already existing fibrin by plasmin. Because these compounds may not only inhibit the generation of thrombi, but impact hemostatic processes as well, prolonged bleeding times may occur, which may potentially limit the options for strong anticoagulant efficacy. Compounds with a broad therapeutic window are therefore advantageous.

In acute prophylactic or interventional settings, fast onset and sufficient controllability of anticoagulant efficacy is desired, which can be achieved by parenteral administration of compounds with a short duration of pharmacological action. Therefore, anticoagulant compounds for oral administration, which include mainly vitamin K antagonists and direct oral anticoagulants (DOACs) are not preferable in this setting—because of their delayed pharmacological onset and prolonged pharmacological action which limit controllability of treatment. In addition, for many patients the administration of oral medication might be challenging. In order to be able to apply such an anticoagulant compound intravenously, sufficient solubility is needed. Since acute care patients are often treated with more than one drug, a low acute drug-drug interaction potential is preferable.

The anticoagulants known from the prior art, for example substances for inhibiting or preventing blood coagulation, have various disadvantages. Accordingly, in practice, efficient treatment methods or the prophylaxis of thrombotic/thromboembolic disorders are found to be very difficult and unsatisfactory.

In acute situations hypercoagulable states can be initiated via the intrinsic or the extrinsic pathway. Therefore, it is beneficial to target the common pathway with factor Xa and thrombin in such indications. While factor Xa inhibition alone does not inhibit the pre-existing thrombin in already formed clots, thrombin inhibition alone, e.g. with hirudin, bivalirudin or argatroban, might be disadvantageous with regards to the therapeutic window, potentially because large compound amounts are needed to stop the waterfall cascade of the coagulation system just at the final step. Therefore, compounds, which can regulate thrombin generation by factor Xa inhibition and inhibit already pre-existing thrombin, as well, might be of interest in the treatment of hypercoagulable states, as they exist for example in the course of infectious diseases caused for example by bacteria, viruses and fungi. In addition, such patients are often linked to extracorporeal systems, in which the blood is exposed to procoagulant surfaces, and may benefit from the anticoagulation therapy.

In the therapy and prophylaxis of acute thromboembolic disorders, use is made firstly of heparin, which is administered intravenously or subcutaneously. Because of more favorable pharmacokinetic and pharmacodynamic properties, preference is these days increasingly given to low-molecular-weight heparin. However, the known disadvantages described hereinbelow encountered in heparin therapy cannot be avoided in this manner. There is a high risk of bleeding, in particular cerebral hemorrhages and gastrointestinal bleedings, and treatment over days enhances the risk for heparin-induced thrombocytopenia (HIT) development. Heparins inhibit factor Xa and thrombin indirectly by accelerating the binding of antithrombin-III (ATIII) to factor Xa and thrombin, which leads to additional ATIII consumption. Given its protective role towards the endothelium, an increased heparin-induced depletion of ATIII is additionally critical during a consumptive coagulopathy. In addition, heparins contribute only little to the inhibition of clot-bound thrombin and factor Xa.

Lately, small molecules have been described, which combine thrombin and factor Xa inhibition with varying ratios within one molecule. These approaches have been tested in vitro and in vivo and have demonstrated remarkable synergistic potential.

EP42675 combines a peptidomimetic part for direct thrombin inhibition and a Fondaparinux-like part, which indirectly inhibits factor Xa. This molecule, however, is dependent on the presence of ATIII. Tanogitran is another small molecule compound, which inhibits both thrombin and factor Xa in vitro but with a stronger efficacy towards thrombin. To a large extent tanogitran is eliminated via the kidney unmetabolized and thus would require dose adaptations and close monitoring in patients with renal insufficiency.

It is therefore an object of the present invention to provide novel compounds which act as factor Xa and thrombin inhibitors for the treatment of cardiovascular disorders, in particular of thrombotic or thromboembolic disorders and/or thrombotic or thromboembolic complications, in humans and animals, which compounds have a wide therapeutic window, good solubility and a short duration of pharmacological action to achieve a sufficient controllability.

WO2009/103440, WO2014/174102 and J. Meneyrol, et al., J. Med. Chem. 2013, 56, 9441-945 describe inter alia substituted chlorothiophene-amides as inhibitors of factor Xa and thrombin. J.-M. Altenburger, et al., Bioorg. Med. Chem. 2004, 12, 1713-1730 describe inter alia substituted sulfonamides as inhibitors of thrombin.

The invention provides 2-(1-Methyl-1H-imidazol-2-yl)ethyl 3-[(5-chlorothiophene-2-carbonyl)amino]-N-{2-ethyl-3-[(3S)-3-hydroxy-2-oxopyrrolidin-1-yl]benzene-1-sulfonyl}-S-alaninate of the formula (I)

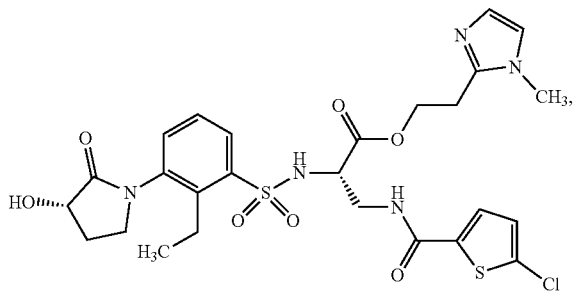

and the salts thereof, the solvates thereof and the solvates of the salts thereof.

The inventive compounds may, depending on their structure, exist in different stereoisomeric forms, i.e. in the form of configurational isomers or else, if appropriate, of conformational isomers (enantiomers and/or diastereomers, including those in the case of rotamers and atropisomers). The present invention therefore encompasses the enantiomers and diastereomers, and the respective mixtures thereof. The stereoisomerically uniform constituents can be isolated from such mixtures of enantiomers and/or diastereomers in a known manner; chromatography processes are preferably used for this, especially HPLC chromatography on an achiral or chiral phase.

If the compounds according to the invention can occur in tautomeric forms, the present invention encompasses all the tautomeric forms.

The present invention also encompasses all suitable isotopic variants of the compounds according to the invention. An isotopic variant of an inventive compound is understood here as meaning a compound in which at least one atom within the inventive compound has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, phosphorus, sulfur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$J and $^{131}$I. Particular isotopic variants of a compound according to the invention, especially those in which one or more radioactive isotopes have been incorporated, may be beneficial, for example, for the examination of the mechanism of action or of the active ingredient distribution in the body; due to comparatively easy preparability and detectability, especially compounds labelled with $^3$H or $^{14}$C isotopes are suitable for this purpose. In addition, the incorporation of isotopes, for example of deuterium, may lead to particular therapeutic benefits as a consequence of greater metabolic stability of the compound, for example an extension of the half-life in the body or a reduction in the active dose required; such modifications of the inventive compounds may therefore in some cases also constitute a preferred embodiment of the present invention. Isotopic variants of the compounds according to the invention can be prepared by the processes known to those skilled in the art, for example by the methods described further below and the procedures described in the working examples, by using corresponding isotopic modifications of the respective reagents and/or starting compounds.

Preferred salts in the context of the present invention are physiologically acceptable salts of the compounds according to the invention. However, the invention also encompasses salts which themselves are unsuitable for pharmaceutical applications but which can be used, for example, for the isolation or purification of the compounds according to the invention.

Physiologically acceptable salts of the compounds according to the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid. Preferred physiologically acceptable salts of the compounds according to the invention include acid addition salts of hydrochloric acid, sulfuric acid, phosphoric acid, methanesulfonic acid, toluenesulfonic acid, tartaric acid, malic acid and citric acid.

Physiologically acceptable salts of the compounds according to the invention also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine and choline.

Solvates in the context of the invention are described as those forms of the inventive compounds which form a complex in the solid or liquid state by coordination with solvent molecules. Hydrates are a specific form of the solvates in which the coordination is with water.

The present invention additionally also encompasses prodrugs of the inventive compounds. The term "prodrugs" encompasses compounds which for their part may be biologically active or inactive but are converted during their residence time in the body into compounds according to the invention (for example by metabolism or hydrolysis).

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

Preference is given to the compound 2-(1-Methyl-1H-imidazol-2-yl)ethyl 3-[(5-chlorothiophene-2-carbonyl)amino]-N-{2-ethyl-3-[(3S)-3-hydroxy-2-oxopyrrolidin-1-yl]benzene-1-sulfonyl}-S-alaninate of the formula (I)

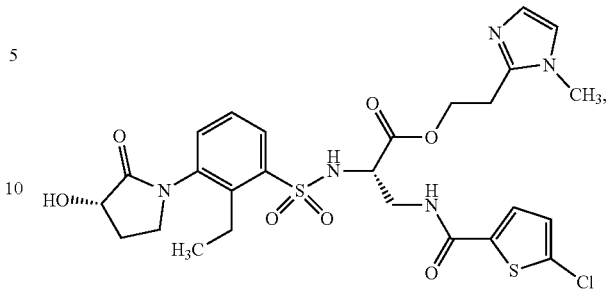

Preference is also given to the compound 2-(1-Methyl-1H-imidazol-2-yl)ethyl 3-[(5-chlorothiophene-2-carbonyl)amino]-N-{2-ethyl-3-[(3S)-3-hydroxy-2-oxopyrrolidin-1-yl]benzene-1-sulfonyl}-S-alaninate of the formula (I)

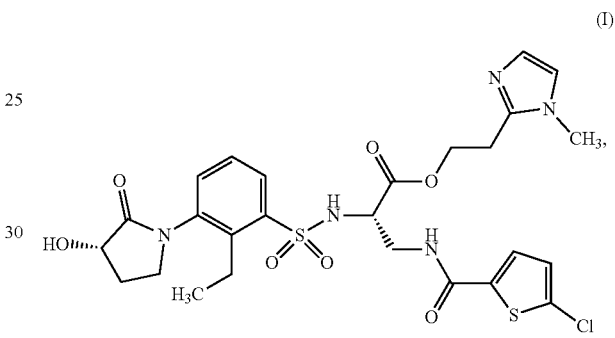

and the physiologically acceptable salts thereof.

Preference is also given to a physiologically acceptable salt of the compound of the formula (I) selected from the group consisting of 2-(1-methyl-1H-imidazol-2-yl)ethyl 3-[(5-chlorothiophene-2-carbonyl)amino]-N-{2-ethyl-3-[(3S)-3-hydroxy-2-oxopyrrolidin-1-yl]benzene-1-sulfonyl}-S-alaninate hydrochloride and 2-(1-methyl-1H-imidazol-2-yl)ethyl 3-{[(5-chloro-2-thienyl)carbonyl]amino}-N-({2-ethyl-3-[(3S)-3-hydroxy-2-oxopyrrolidin-1-yl]phenyl}sulfonyl)-S-alaninate sulfate and 2-(1-methyl-1H-imidazol-2-yl)ethyl 3-{[(5-chloro-2-thienyl)carbonyl]amino}-N-({2-ethyl-3-[(3S)-3-hydroxy-2-oxopyrrolidin-1-yl]phenyl}sulfonyl)-S-alaninate methanesulfonate and 2-(1-methyl-1H-imidazol-2-yl)ethyl 3-{[(5-chloro-2-thienyl)carbonyl]amino}-N-({2-ethyl-3-[(3S)-3-hydroxy-2-oxopyrrolidin-1-yl]phenyl}sulfonyl)-S-alaninate 4-methylbenzene-sulfonate and 2-(1-methyl-1H-imidazol-2-yl)ethyl 3-{[(5-chloro-2-thienyl)carbonyl]amino}-N-({2-ethyl-3-[(3S)-3-hydroxy-2-oxopyrrolidin-1-yl]phenyl}sulfonyl)-S-alaninate maleate and 2-(1-methyl-1H-imidazol-2-yl)ethyl 3-{[(5-chloro-2-thienyl)carbonyl]amino}-N-({2-ethyl-3-[(3S)-3-hydroxy-2-oxopyrrolidin-1-yl]phenyl}sulfonyl)-S-alaninate phosphate and
2-(1-methyl-1H-imidazol-2-yl)ethyl 3-{[(5-chloro-2-thienyl)carbonyl]amino}-N-({2-ethyl-3-[(3S)-3-hydroxy-2-oxopyrrolidin-1-yl]phenyl}sulfonyl)-S-alaninate (2R, 3R)-tartrate
and
2-(1-methyl-1H-imidazol-2-yl)ethyl 3-{[(5-chloro-2-thienyl)carbonyl]amino}-N-({2-ethyl-3-[(3S)-3-hydroxy-2-oxopyrrolidin-1-yl]phenyl}sulfonyl)-S-alaninate citrate.

The invention further provides a method for preparing the compound of the formula (I), or salts thereof, solvates thereof or solvates of the salts thereof, wherein the compound of the formula (II)

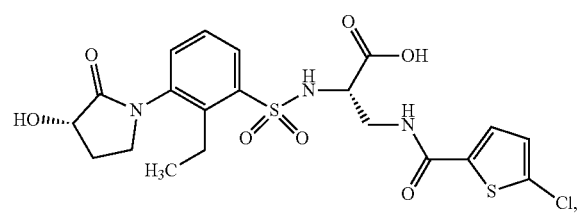

is reacted with the compound of the formula (III)

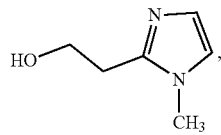

in the presence of a dehydrating agent to give the compound of the formula (I), and the compound of the formula (I) is optionally converted with the corresponding (i) solvents and/or (ii) bases or acids into its solvates, salts and/or solvates of the salts.

The reaction is generally carried out in inert solvents, if appropriate in the presence of a base, preferably in a temperature range from −20° C. to 80° C. at atmospheric pressure.

Suitable dehydrating agents here are, for example, carbodiimides such as N,N'-diethyl-, N,N'-dipropyl-, N,N'-diisopropyl-, N,N'-dicyclohexylcarbodiimide, 1-ethyl-3-(3-dimethylaminopropyl)-carbodiimide hydrochloride (EDCI), N-cyclohexylcarbodiimide-N'-propyloxymethyl-polystyrene (PS-carbodiimide) or carbonyl compounds such as carbonyldiimidazole, or 1,2-oxazolium compounds such as 2-ethyl-5-phenyl-1,2-oxazolium 3-sulfate or 2-tert-butyl-5-methyl-isoxazolium perchlorate, or acylamino compounds such as 2-ethoxy-1-ethoxycarbonyl-1,2-dihydroquinoline, or isobutyl chloroformate, or bis-(2-oxo-3-oxazolidinyl) phosphoryl chloride or benzotriazolyloxy-tri(dimethylamino)-phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), (benzotriazol-1-yloxy)bisdimethylaminomethylium fluoroborate (TBTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethyl-amino)phosphonium hexafluorophosphate (BOP), or ethyl cyano(hydroxyimino)acetate (Oxyma), or (1-cyano-2-ethoxy-2-oxoethylidenaminooxy)dimethylamino-morpholino-carbenium hexafluorophosphate (COMU), or N-[(dimethylamino)(3H-[1,2,3]triazolo[4,5-b]pyridin-3-yloxy)methylidene]-N-methylmethan-aminium hexafluorophosphate, or 2,4,6-tripropyl-1,3,5,2,4,6-trioxatriphosphinane-2,4,6-trioxide (T3P), or mixtures of these with bases. The condensation with ethyl cyano(hydroxyimino)acetate (Oxyma) and 1-ethyl-3-(3-dimethylaminopropyl)carbodiimide hydrochloride (EDCI) is preferred.

Bases are, for example, organic bases such as trialkylamines, for example triethylamine, N-methylmorpholine, N-methylpiperidine, 4-dimethylaminopyridine or diisopropylethylamin, or pyridine. Preference is given to a condensation without a base.

Inert solvents are, for example, halogenated hydrocarbons such as dichloromethane or trichloromethane, hydrocarbons such as benzene or toluene, or other solvents such as 1,4-dioxane, diethyl ether, tetrahydrofuran, ethyl acetate, N,N-dimethylformamide, dimethyl sulfoxide or acetonitrile, or mixtures of the solvents. Preference is given to a mixture of dichloromethane and N,N-dimethylformamide.

The compounds of the formula (II) and (III) are known, can be synthesized from the corresponding starting compounds by known processes or can be prepared analogously to the processes described in the A) Examples section.

The preparation of the starting compounds and of the compounds of the formula (I) can be illustrated by the synthesis scheme which follows.

Scheme

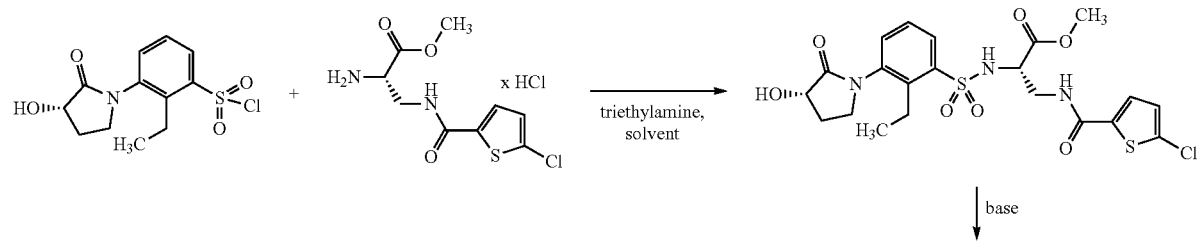

-continued

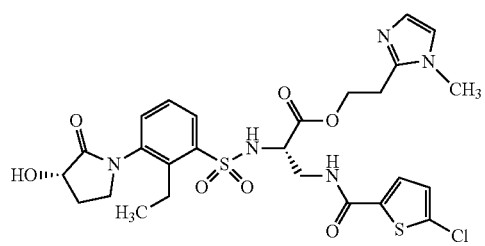 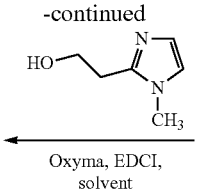 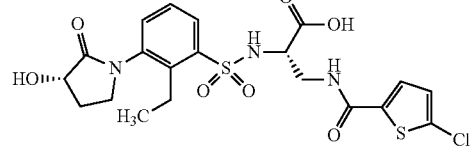

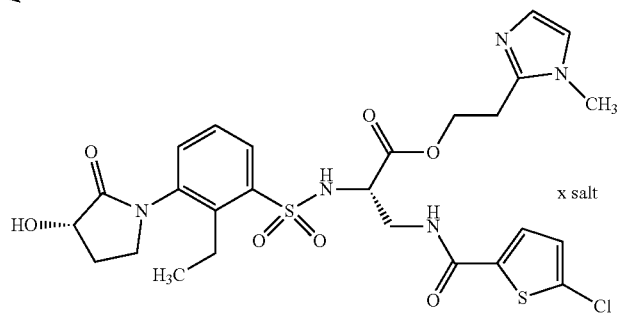

The compounds according to the invention have an unforeseeable useful pharmacological activity spectrum and good pharmacokinetic properties. They are compounds that inhibit factor Xa and thrombin. They are therefore suitable for use as medicaments for the treatment and/or prophylaxis of diseases in humans and animals.

The present invention further provides for the use of the compounds according to the invention for the treatment and/or prophylaxis of disorders, in particular vascular disorders, preferably thrombotic or thromboembolic disorders and/or thrombotic or thromboembolic complications such as disseminated intravascular coagulation, and/or inflammatory disorders.

Factor Xa (FXa) and Factor IIa (FIIa, i.e. thrombin) are crucial enzymes involved in coagulation. Thrombin is directly activated by FXa in the prothrombinase complex and in turn activates Fibrinogen into Fibrin, one of the major components of blood clots.

As part of the "common" pathway of coagulation, FXa and thrombin are important components for both the intrinsic and extrinsic initiation of coagulation. In the extrinsic pathway, coagulation is triggered via tissue factor (TF), which is expressed in the vascular adventitia and becomes exposed to blood as a result of vascular injury. Tissue factor can also be secreted by monocytes or activated endothelial cells upon certain triggers (e.g. bacterial endotoxins). In the intrinsic pathway, the coagulation system can be activated particularly on negatively charged surfaces, which include not only surface structures of foreign cells (e.g. bacteria) but also artificial surfaces such as vascular prostheses, stents and extracorporeal circulation. On the surface, initially factor XII (FXII) is activated to factor XIIa (FXIIa) which subsequently activates factor XI (FXI), attached to cell surfaces, to factor XIa (FXIa). Both, the extrinsic and intrinsic pathway converge in the common pathway, in which FXa activates prothrombin to thrombin, which in turn will 1) further propagate the downstream coagulation cascade resulting in fibrin generation and clot formation as described above and 2) re-initiate the coagulation cascade in a feedback loop via activation of FXI to FXIa.

Accordingly, the compounds according to the invention are suitable for the treatment and/or prophylaxis of disorders or complications which may arise from the formation of clots.

For the purpose of the present invention, the "thrombotic or thromboembolic disorders" include disorders which occur both in the arterial and in the venous vasculature and which can be treated with the compounds according to the invention, in particular for the treatment and prevention of disseminated intravascular coagulation (DIC) which may occur in connection with sepsis inter alia, but also owing to surgical interventions, neoplastic disorders, burns or other injuries that may lead to severe organ damage through microthromboses. In the course of an infection, there may be a generalized activation of the coagulation system (disseminated intravascular coagulation or consumption coagulopathy, hereinbelow referred to as "DIC") with microthrombosis in various organs and secondary haemorrhagic complications. During DIC, there is a massive activation of the coagulation system at the surface of damaged endothelial cells, the surfaces of foreign bodies or crosslinked extravascular tissue. Consequently, there is coagulation in small vessels of various organs with hypoxia and subsequent organ dysfunction. A secondary effect is the consumption of coagulation factors (for example factor X, prothrombin and fibrinogen) and platelets, which reduces the coagulability of the blood and may result in heavy bleeding. Moreover, there may be endothelial damage with increased permeability of the vessels and diffusion of fluid and proteins into the extravasal space.

The compounds according to the invention are also suitable to prevent or treat complications that may arise in the context of an infectious disease, and/or of systemic inflammatory syndrome (SIRS), such as septic organ dysfunction, septic organ failure and multiorgan failure, acute respiratory distress syndrome (ARDS), acute lung injury (ALI), septic shock and/or septic organ failure.

Thromboembolic complications furthermore occur in microangiopathic haemolytical anaemias and by the blood coming into contact with foreign surfaces in the context of extracorporeal circulation such as, for example, haemodialysis, ECMO ("extracorporeal membrane oxygenation"), LVAD ("left ventricular assist device") and similar methods, AV fistulas, vascular and heart valve prostheses.

In addition, the inventive compounds are suitable for the treatment and prevention of disorders in the coronary arteries of the heart, such as acute coronary syndrome (ACS), myocardial infarction with ST segment elevation (STEMI) and without ST segment elevation (non-STEMI), stable angina pectoris, unstable angina pectoris, reocclusions and restenoses after coronary interventions such as angioplasty, stent implantation or aortocoronary bypass.

The inventive compounds are also suitable for the prevention and treatment of cardiogenic thromboembolisms, for example brain ischaemias, stroke and systemic thromboembolisms and ischaemias, in patients with acute, intermittent or persistent cardiac arrhythmias, for example atrial fibrillation, and in patients undergoing cardioversion, and also in patients with heart valve disorders or with artificial heart valves The compounds according to the invention can also be used for use in the treatment and/or prophylaxis of disorders in the cerebrovascular arteries, such as transitory ischaemic attacks (TIA), ischemic strokes including cardioembolic strokes, such as strokes due to atrial fibrillation, non-cardioembolic strokes, such as lacunar stroke, strokes due to large or small artery diseases, or strokes due to undetermined cause, cryptogenic strokes, embolic strokes, embolic strokes of undetermined source, or events of thrombotic and/or thromboembolic origin leading to stroke or TIA.

The compounds according to the invention can also be used for the treatment and/or prophylaxis of disorders of peripheral arteries, leading to peripheral artery disease, including peripheral artery occlusion, acute limb ischemia, amputation, reocclusions and restenoses after interventions such as angioplasty, stent implantation or surgery and bypass, and/or stent thrombosis.

In addition, the compounds according to the invention can also be used for the treatment and/or prophylaxis of disorders in venous vessels, leading to venous thromboses, in particular among others in deep leg veins, kidney veins, retinal veins and/or cerebrovascular sinus veins, and/or venous thromboembolisms resulting potentially in pulmonary artery emboli.

Stimulation of the coagulation system may occur by various causes or associated disorders. In the context of surgical interventions, immobility, confinement to bed, infections, inflammation or cancer or cancer therapy, inter alia, the coagulation system can be highly activated, and there may be thrombotic complications, in particular venous thromboses. The compounds according to the invention are therefore suitable for the prophylaxis of thromboses in the context of surgical interventions in patients suffering from cancer.

The compounds according to the invention are also suitable for the primary prophylaxis of thrombotic or thromboembolic disorders and/or inflammatory disorders and/or disorders with increased vascular permeability in patients in which gene mutations lead to enhanced activity of the enzymes, or increased levels of the zymogens and these are established by relevant tests/measurements of the enzyme activity or zymogen concentrations.

The present invention further provides for the use of the compounds according to the invention for the treatment and/or prophylaxis of disorders, especially the disorders mentioned above.

The present invention further provides for the use of the compounds according to the invention for production of a medicament for the treatment and/or prophylaxis of disorders, especially the disorders mentioned above.

The present invention further provides a method for the treatment and/or prophylaxis of disorders, especially the disorders mentioned above, using a therapeutically effective amount of a compound according to the invention.

The present invention further provides the compounds according to the invention for use in a method for the treatment and/or prophylaxis of disorders, especially the disorders mentioned above, using a therapeutically effective amount of a compound according to the invention.

Particular the present invention provides the compounds according to the invention for use in a method for the treatment and/or prophylaxis of thrombotic or thromboembolic disorders using a therapeutically effective amount of a compound according to the invention.

The present invention further provides medicaments comprising a compound according to the invention and one or more further active compounds.

In addition, the compounds according to the invention can also be used for preventing coagulation ex vivo, for example for the protection of organ transplants against damage caused by formation of clots and for protecting the organ recipient against thromboemboli from the transplanted organ, for preserving blood and plasma products, for cleaning/pretreating catheters and other medical auxiliaries and instruments, for coating synthetic surfaces of medical auxiliaries and instruments used in vivo or ex vivo or for biological samples which may contain factor Xa or thrombin.

The present invention further provides medicaments comprising a compound according to the invention and one or more further active compounds, in particular for the treatment and/or prophylaxis of the disorders mentioned above. Preferred examples of active compounds suitable for combinations include:

lipid-lowering substances, especially HMG-CoA (3-hydroxy-3-methylglutaryl-coenzyme A) reductase inhibitors, for example lovastatin (Mevacor), simvastatin (Zocor), pravastatin (Pravachol), fluvastatin (Lescol) and atorvastatin (Lipitor);

coronary therapeutics/vasodilatators, especially ACE (angiotensin converting enzyme) inhibitors, for example captopril, lisinopril, enalapril, ramipril, cilazapril, benazepril, fosinopril, quinapril and perindopril, or AII (angiotensin II) receptor antagonists, for example embusartan, losartan, valsartan, irbesartan, candesartan, eprosartan and temisartan, or β-adrenoceptor antagonists, for example carvedilol, alprenolol, bisoprolol, acebutolol, atenolol, betaxolol, carteolol, metoprolol, nadolol, penbutolol, pindolol, propanolol and timolol, or alpha-1-adrenoceptor antagonists, for example prazosine, bunazosine, doxazosine and terazosine, or diuretics, for example hydrochlorothiazide, furosemide, bumetanide, piretanide, torasemide, amiloride and dihydralazine, or calcium channel blockers, for example verapamil and diltiazem, or dihydropyridine derivatives, for example nifedipin (Adalat) and nitrendipine (Bayotensin), or nitro preparations, for example isosorbide 5-mononitrate, isosorbide dinitrate and glycerol trinitrate, or substances causing an increase in cyclic guanosine monophosphate (cGMP), for example stimulators of soluble guanylate cyclase, for example riociguat;

plasminogen activators (thrombolytics/fibrinolytics) and compounds which promote thrombolysis/fibrinolysis such as inhibitors of the plasminogen activator inhibitor (PAI inhibitors) or inhibitors of the thrombin-activated fibrinolysis inhibitor (TAFI inhibitors) such as, for example, tissue plasminogen activator (t-PA, for example Actilyse®), streptokinase, reteplase and urokinase or plasminogen-modulating substances causing increased formation of plasmin;

anticoagulatory substances (anticoagulants) such as, for example, heparin (UFH), low-molecular-weight heparins (LMW), for example tinzaparin, certoparin, parnaparin, nadroparin, ardeparin, enoxaparin, reviparin, dalteparin, danaparoid, semuloparin (AVE 5026), adomiparin (M118) and EP-42675/ORG42675;

direct thrombin inhibitors (DTI) such as, for example, Pradaxa (dabigatran), atecegatran (AZD-0837), DP-4088, SSR-182289A, argatroban, bivalirudin and tanogitran (BIBT-986 and prodrug BIBT-1011), hirudin;

direct factor Xa inhibitors such as, for example, rivaroxaban, apixaban, edoxaban (DU-176b), betrixaban (PRT-54021), R-1663, darexaban (YM-150), otamixaban (FXV-673/RPR-130673), letaxaban (TAK-442), razaxaban (DPC-906), DX-9065a, LY-517717, tanogitran (BIBT-986, prodrug: BIBT-1011), idraparinux and fondaparinux, substances which inhibit the aggregation of platelets (platelet aggregation inhibitors, thrombocyte aggregation inhibitors), such as, for example, acetylsalicylic acid (such as, for example, aspirin), P2Y12 antagonists such as, for example, ticlopidine (Ticlid), clopidogrel (Plavix), prasugrel, ticagrelor, cangrelor, elinogrel, PAR-1 antagonists such as, for example, vorapaxar, PAR-4 antagonists, EP3 antagonists such as, for example, DG041;

platelet adhesion inhibitors such as GPVI and/or GPIb antagonists such as, for example, Revacept or caplacizumab;

fibrinogen receptor antagonists (glycoprotein-IIb/IIIa antagonists), for example abciximab, eptifibatide, tirofiban, lamifiban, lefradafiban and fradafiban;

recombinant human activated protein C such as, for example, Xigris or recombinant thrombomudulin;

and also antiarrhythmics;

corticosteroids such as, for example, anecortave, betamethasone, dexamethasone, triamcinolone, fluocinolone and fluocinolone acetonide;

cyclooxygenase inhibitors such as, for example, bromfenac and nepafenac;

inhibitors of the kallikrein-kinin system such as, for example, safotibant and ecallantide;

inhibitors of the sphingosine 1-phosphate signal paths such as, for example, sonepcizumab;

inhibitors of the complement-C5a receptor such as, for example, eculizumab;

inhibitors of the 5HT1a receptor such as, for example, tandospirone;

inhibitors of coagulation factor XI or XIa such as, for example, osocimab, abelacimab, asundexian and milvexian;

vasoconstricting agents such as, for example, epinephrin, norepinephrine and dopamine;

antibiotics such as, for example, piperacillin, combactam, erythromycin, metronidazol, ciprofloxacin and vancomycin;

compounds to sustain end-organ function during the treatment of acute respiratory distress syndrome or acute kidney injury.

"Combinations" for the purpose of the invention mean not only dosage forms which contain all the components (so-called fixed combinations) and combination packs which contain the components separate from one another, but also components which are administered simultaneously or sequentially, provided that they are used for prophylaxis and/or treatment of the same disease. It is likewise possible to combine two or more active ingredients with one another, meaning that they are thus each in two-component or multicomponent combinations.

The inventive compounds can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The inventive compounds can be administered in administration forms suitable for these administration routes.

Suitable administration forms for oral administration are those which function according to the prior art and deliver the inventive compounds rapidly and/or in modified fashion, and which contain the inventive compounds in crystalline and/or amorphized and/or dissolved form, for example tablets (uncoated or coated tablets, for example having enteric coatings or coatings which are insoluble or dissolve with a delay, which control the release of the compound according to the invention), tablets which disintegrate rapidly in the mouth, or films/wafers, films/lyophilisates, capsules (for example hard or soft gelatin capsules), sugar-coated tablets, granules, pellets, powders, emulsions, suspensions, aerosols or solutions.

Parenteral administration can be accomplished with avoidance of a resorption step (for example by an intravenous, intraarterial, intracardiac, intraspinal or intralumbar route) or with inclusion of a resorption (for example by an intramuscular, subcutaneous, intracutaneous, percutaneous or intraperitoneal route). Administration forms suitable for parenteral administration include preparations for injection and infusion in the form of solutions, suspensions, emulsions, lyophilizates or sterile powders.

Preference is given to parenteral administration.

Suitable administration forms for the other administration routes are, for example, pharmaceutical forms for inhalation (including powder inhalers, nebulizers), nasal drops, solutions or sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (for example patches), milk, pastes, foams, dusting powders, implants or stents.

The inventive compounds can be converted to the administration forms mentioned. This can be accomplished in a manner known per se by mixing with inert, nontoxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulfate, polyoxysorbitan oleate), binders (for example polyvinylpyrrolidone), synthetic and natural polymers (for example albumin), stabilizers (e.g.

antioxidants, for example ascorbic acid), colourants (e.g. inorganic pigments, for example iron oxides) and flavour and/or odour correctants.

The present invention further provides medicaments comprising at least one inventive compound, preferably together with one or more inert nontoxic pharmaceutically suitable excipients, and the use thereof for the purposes mentioned above.

In the case of parenteral administration, it has generally been found to be advantageous to administer amounts of about 100 mg to 15 g every 24 hours to achieve effective results, it is preferred to administer amounts of about 500 mg to 7.5 g every 24 hours, and it is very preferred to administer amounts of about 1 g to 3.5 g every 24 hours.

In spite of this, it may be necessary, if appropriate, to deviate from the amounts specified, specifically depending on body weight, administration route, individual behaviour towards the active ingredient, type of formulation, and time or interval of administration.

Unless stated otherwise, the percentages in the tests and examples which follow are percentages by weight; parts are parts by weight. Solvent ratios, dilution ratios and concentration data for the liquid/liquid solutions are based in each case on volume. "w/v" means "weight/volume". For example, "10% w/v" means: 100 ml of solution or suspension comprise 10 g of substance.

A)
Examples
Abbreviations:

| Abbreviation | Meaning |
|---|---|
| Boc | tert-Butyloxycarbonyl |
| br | broad (NMR) |
| CI | chemical ionisation |
| d | doublet (NMR) |
| d | day(s) |
| DCM | dichloromethane |
| dd | double-doublet (NMR) |
| DIPEA | diisopropylethylamine |
| DMAP | 4-(dimethylamino)pyridine |
| DMEDA | N,N'-dimethylethane-1,2-diamine |
| DMF | N,N-dimethylformamide |
| DMSO | dimethyl sulfoxide |
| EDCI | 1-ethyl-3-(3-dimethylaminopropyl)carbodiimide hydrochloride |
| ESI | electrospray (ES) ionisation |
| h | hour(s) |
| H | proton |
| HBTU | (2-(1H-benzotriazol-1-yl)-1,1,3,3-tetramethyluronium hexafluorophosphate |
| HCl | hydrochloric acid |
| HPLC | high performance liquid chromatography |
| IC | ion chromatography |
| IR | infrared spectroscopy |
| LC-MS | liquid chromatography mass spectrometry |
| m | multiplet (NMR) |
| M | molar |
| min | minute(s) |
| NCS | N-chlorosuccinimide |
| MS | mass spectrometry |
| NMR | nuclear magnetic resonance spectroscopy |
| Oxyma | ethyl cyanohydroxyiminoacetate |
| RP | reversed phase (HPLC) |
| rt | room temperature |
| $R_t$ | retention time (HPLC, LC/MS) |
| s | singlet (NMR) |
| t | triplet (NMR) |
| TBTU | 2-(1H-benzotriazole-1-yl)-1,1,3,3-tetramethylaminium tetrafluoroborate |
| tert | tertiary |
| TFA | trifluoro acetic acid |
| THF | tetrahydrofuran |

-continued

A)
Examples
Abbreviations:

| Abbreviation | Meaning |
|---|---|
| UV | ultraviolet spectroscopy |
| wt % | percentage by weight |
| XRPD | X-Ray powder diffraction |

HPLC and LC-MS Methods:

Method 1 (preparative HPLC): Column: Chromatorex C18, 10 μm, 205×50 mm; eluent A: water, eluent B: acetonitril; injection at 3 min; gradient: 0.0 min 10% B→6.0 min 10% B→27 min 95% B→38 min 95% B→39 min 10% B→40.2 min 10% B; flow: 150 ml/min; UV-detection: 210 nm.

Method 2 (preparative HPLC): Column: RP18 column, eluent: acetonitril/water gradient with 0.1% TFA added to the water phase.

Method 3 (preparative HPLC): Column: Chromatorex C18, 10 μm, 205×50 mm; eluent A: water, eluent B: acetonitril; injection at 3 min; gradient: 0.0 min 10% B→5.5 min 10% B→17.65 min 95% B→19.48 min 95% B→19.66 min 10% B→20.51 min 10% B; flow: 150 ml/min; UV-detection: 210 nm.

Method 4 (preparative HPLC): Chromatorex C18, 10 μm, 250×50 mm 30% acetonitril/70% water (+0.1% TFA)→Gradient over 38 min→95% acetonitril/5% water (+0.1% TFA).

Method 5 (preparative HPLC): Chromatorex C18, 10 μm, 125×30 mm; eluent A: water+0.1% TFA, eluent B: acetonitril; injection at 3 min; gradient: 0.0 min 10% B→6.0 min 10% B→27 min 95% B→38 min 95% B→39 min 10% B→40.2 min 10% B; flow: 75 ml/min; UV-detection: 210 nm.

Method 6 (preparative HPLC): Chromatorex C18, 10 μm, 125×30 mm; eluent A: water+0.01% HCl, eluent B: acetonitril; injection bei 3 min; gradient: 0.0 min 10% B→6.0 min 10% B→27 min 95% B→38 min 95% B→39 min 10% B→40.2 min 10% B; flow: 75 ml/min, UV-detection: 210 nm.

Method 7 (LC/MS): System MS: Thermo Scientific FT-MS; System UHPLC+: Thermo Scientific UltiMate 3000; Column: Waters, HSST3, 2.1×75 mm, C18 1.8 μm; eluent A: 1 1 water+0.01% formic acid; eluent B: 1 1 acetonitrile+0.01% formic acid; gradient: 0.0 min 10% B→2.5 min 95% B→3.5 min 95% B; oven: 50° C.; flow: 0.90 ml/min; UV-detection: 210 nm/optimum integration path 210-300 nm.

Method 8 (LC/MS): Instrument: Waters ACQUITY SQD UPLC System; Column: Waters Acquity UPLC HSS T3 1.8 μm 50×1 mm; eluent A: 1 1 water+0.25 ml 99% formic acid, eluent B: 1 1 acetonitrile+0.25 ml 99% formic acid; gradient: 0.0 min 90% A→1.2 min 5% A→2.0 min 5% A; oven: 50° C.; flow: 0.40 ml/min; UV-detection: 210 nm.

Method 9 (LC/MS): Instrument: Agilent MS Quad 6150; HPLC: Agilent 1290; Column: Waters Acquity UPLC HSS T3 1.8 μm 50×2.1 mm; eluent A: 1 1 water+0.25 ml 99% formic acid, eluent B: 1 1 acetonitrile+0.25 ml 99% formic acid; gradient: 0.0 min 90% A→0.3 min 90% A→1.7 min 5% A→3.0 min 5% A; oven: 50° C.; flow: 1.20 ml/min; UV-detection: 205-305 nm.

Method 10 (chiral HPLC): Column: Daicel Chiralpak IG, 5 μm, 250×4.6 mm; eluent A: 50% iso-hexane, 50% ethanol+1% water+0.2% TFA; flow: 1.0 ml/min, temperature: 40° C.

Method 11 (chiral HPLC): Column: Daicel Chiralcel IG, 5 μm, 250×4.6 mm; eluent A: 50% n-heptane, 50% ethanol+ 0.2% diethylamine; flow: 1.0 ml/min, temperature: 60° C.

When compounds according to the invention are purified by preparative HPLC by the above-described methods in which the eluents contain additives, for example trifluoroacetic acid, formic acid or ammonia, the compounds according to the invention may be obtained in salt form, for example as trifluoroacetate, formate or ammonium salt, if the compounds according to the invention contain a sufficiently basic or acidic functionality. Such a salt can be converted to the corresponding free base or acid by various methods known to the person skilled in the art.

In the case of the synthesis intermediates and working examples of the invention described hereinafter, any compound specified in the form of a salt of the corresponding base or acid is generally a salt of unknown exact stoichiometric composition, as obtained by the respective preparation and/or purification process. Unless specified in more detail, additions to names and structural formulae, such as "hydrochloride", "trifluoroacetate", "sodium salt" or "x HCl", "x CF$_3$COOH", "x Na+" or other salts should not therefore be understood in a stoichiometric sense in the case of such salts, but have merely descriptive character with regard to the salt-forming components present therein.

This applies correspondingly if synthesis intermediates or working examples or salts thereof were obtained in the form of solvates, for example hydrates, of unknown stoichiometric composition (if they are of a defined type) by the preparation and/or purification processes described.

Microwave: The microwave reactor used was a "single-mode" instrument of the Biotage Initiator™ or Initiator Plus™ type.

Quantitative ion chromatography (IC): Determination of ions with external standards; instrument: Thermo Scientific ICS 5000+; capillary IC columns: IonPac AS11-HC and IonPac CS16; eluent: eluent gradient [H]$^+$[OH]$^-$; detector: conductivity detection.

Proton Nuclear Magnetic Resonance Spectroscopy ($^1$H-NMR): $^1$H-NMR spectra were recorded in deuterated solvent (DMSO-d$_6$) with Bruker Avance spectrometers operating at 400, 500 or 600 MHz, as indicated. Chemical shifts are reported in ppm relative to tetramethylsilane (TMS) as an internal standard. The descriptions of the coupling patterns of $^1$H NMR signals are based on the optical appearance of the signals and do not necessarily reflect the physically correct interpretation. In general, the chemical shift information refers to the center of the signal. In the case of multipletts, intervals are given. Signals obscured or partly obscured by solvent or water were either tentatively assigned or have not been listed. Significantly broadened signals—caused, for example, by rapid rotation of molecular moieties or because of exchanging protons—were likewise assigned tentatively (often referred to as a broad multiplet or broad singlet) or are not listed.

X-Ray powder diffraction (XRPD): X-Ray diffraction patterns were recorded at rt using XRD diffractometers X'Pert PRO (PANalytical) (radiation Cu K alpha 1, wavelength 1.5406 Å). There was no sample preparation. All X-Ray reflections are quoted as 020 (theta) values (peak maxima) with a resolution of ±0.2°.

Infrared spectroscopy (IR): IR spectra were recorded at rt using a FT-IR spectrophotometer using a Tensor 37 device from Bruker. Resolution was 2 cm$^{-1}$.

In NMR spectra of mixtures of stereoisomers, numbers mentioned with "and" indicate that the stereoisomers show separate signals for the respective hydrogen atom, i.e. " . . . and . . . (2×s, 1H)" means that one hydrogen atom is represented by 2 singlets, each singlet from one or more different stereoisomer(s).

STARTING COMPOUNDS

Intermediate 1

1-[3-(Benzylsulfanyl)-2-ethylphenyl]pyrrolidin-2-one

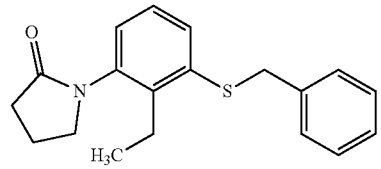 [SMILES: CCc1c(SCc2ccccc2)cccc1N1CCCC1=O]

Figure 1:
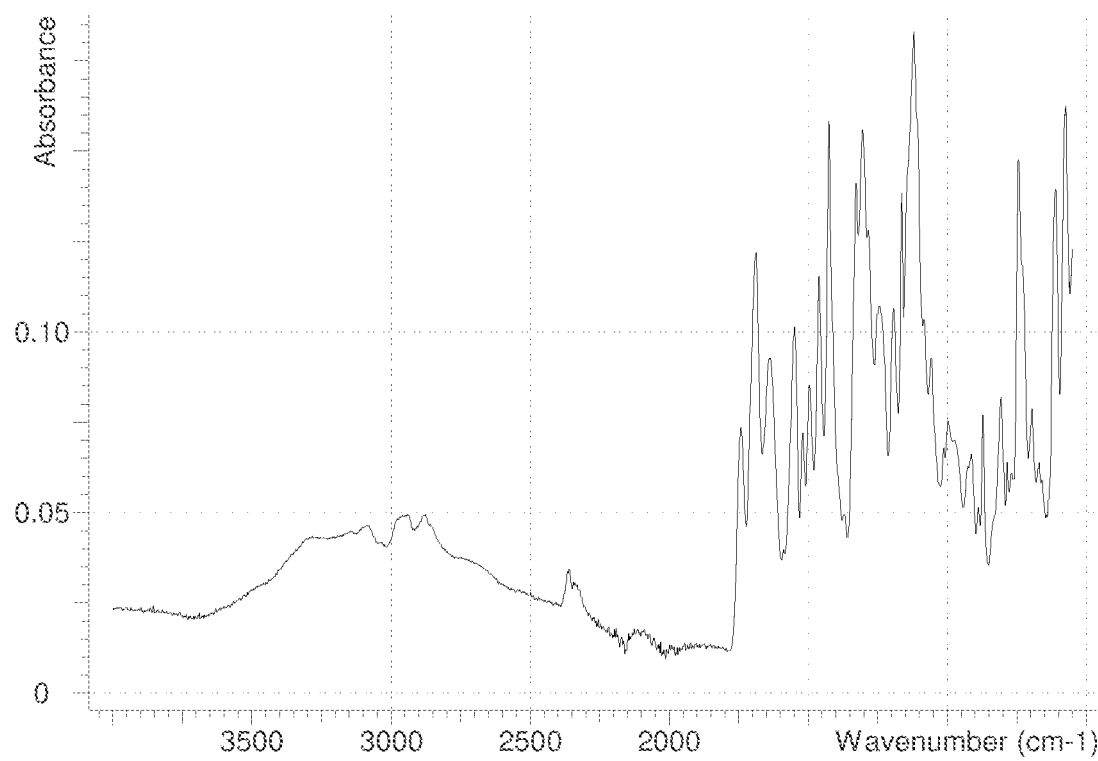
FIG. 1: Infrared spectrum of Example 1

To a solution of 1-(benzylsulfanyl)-3-bromo-2-ethylbenzene (13.0 g, 42.3 mmol; for preparation see *Journal of Medicinal Chemistry* 2013, 56, 9441-9456, compound 40b) and pyrrolidin-2-one (14.5 ml, 190 mmol) in dioxane (345 ml) and DMF (87 ml) under argon, DMEDA (5.5 ml, 50.8 mmol), copper(I)iodide (9.67 g, 50.8 mmol) and potassium carbonate (35.1 g, 254 mmol) were added and argon was bubbled through the mixture for 5 min more minutes. Then, the mixture was stirred at 110° C. for 16 h in a closed autoclave without additional pressure adjustment. After cooling to rt, the mixture was filtered and the solvent was removed under reduced pressure. The residue was taken up in water and ethyl acetate and the phases were separated. The aqueous phase was extracted three times with ethyl acetate, after which the combined organic phases were washed with saturated sodium chloride solution, dried over sodium sulfate and concentrated. The residue was purified via flash chromatography (silica, cyclohexane/ethyl acetate 1:1) to give a first batch of title compound (9.30 g, 65% of theory, 92% purity). A second batch (280 mg, 2% of theory, 99% purity) was obtained after an additional flash chromatography (Biotage Isolera, 50 g silicagel SNAP Ultra cartridge, cyclohexane/ethyl acetate gradient).

LC-MS (Method 7): R$_t$=2.03 min; MS (ESIpos): m/z=312 [M+H]$^+$ $^1$H NMR (400 MHz, DMSO-d$_6$) δ [ppm]: 7.41-7.36 (m, 3H), 7.34-7.29 (m, 2H), 7.28-7.19 (m, 2H), 7.02 (dd, 1H), 4.25 (s, 2H), 3.61 (t, 2H), 2.59-2.50 (m, 2H, partially obscured), 2.40 (t, 2H), 2.16-2.05 (m, 2H), 1.01 (t, 3H)

Intermediate 2

(3S)-1-[3-(Benzylsulfanyl)-2-methylphenyl]-3-hydroxypyrrolidin-2-one

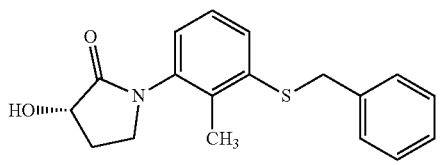 [SMILES: Cc1c(SCc2ccccc2)cccc1N1CC[C@H](O)C1=O]

Under argon, 1-(benzylsulfanyl)-3-bromo-2-methylbenzene (4.50 g, 15.3 mmol; for preparation see WO 2009/103440, page 81, intermediate 83) was mixed with (3S)-3-hydroxypyrrolidin-2-one (3.10 g, 30.7 mmol), copper(I) iodide (4.09 g, 21.5 mmol) and potassium carbonate (8.48 g, 61.4 mmol), followed by the addition of dioxane (120 ml) and DMF (31 ml). DMEDA (2.3 ml, 21.5 mmol) was then added and the mixture was stirred overnight at 110° C. After cooling to rt, the mixture was combined with mixtures from two test reactions that had been obtained under similar conditions starting from 100 mg and 1.0 g 1-(benzylsulfanyl)-3-bromo-2-methylbenzene, respectively. The combined mixtures were filtered over Celite, washed with ethyl acetate and the solvent was removed under reduced pressure. The residue was dissolved in ethyl acetate and water and filtered over Celite again. The phases were separated and the aqueous phase was extracted three times with ethyl acetate. The combined organic phases were washed with saturated sodium chloride solution, dried over sodium sulfate and concentrated. The residue was purified by flash-chromatography (Biotage Isolera, silica cartridge, cyclohexane/ethyl acetate gradient) to give the title compound (4.24 g, 65% of theory, 92% purity). The yield is based on the combined experiments.

LC-MS (Method 9): $R_t$=1.18 min; MS (ESIpos): m/z=314 [M+H]$^+$ $^1$H NMR (600 MHz, DMSO-d$_6$) δ [ppm]: 7.38 (d, 2H), 7.34-7.29 (m, 3H), 7.27-7.23 (m, 1H), 7.21 (t, 1H), 7.05 (d, 1H), 5.65 (d, 1H), 4.33-4.25 (m, 1H), 4.23 (s, 2H), 3.59-3.54 (m, 1H), 3.54-3.48 (m, 1H), 2.45-2.38 (m, 1H), 2.05 (s, 3H), 1.98-1.89 (m, 1H).

Intermediate 3

(3R)-1-[3-(Benzylsulfanyl)-2-methylphenyl]-3-hydroxypyrrolidin-2-one

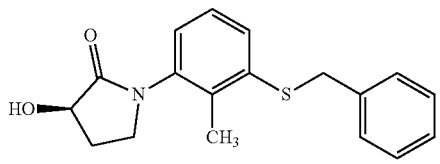 [SMILES: Cc1c(SCc2ccccc2)cccc1N1CC[C@@H](O)C1=O]

Under argon, 1-(benzylsulfanyl)-3-bromo-2-methylbenzene (3.00 g, 10.2 mmol; for preparation see WO 2009/103440, page 81, intermediate 83) was mixed with (3R)-3-hydroxypyrrolidin-2-one (1.86 g, 18.4 mmol), copper(I) iodide (2.73 g, 14.3 mmol) and potassium carbonate (5.66 g, 40.9 mmol), followed by the addition of dioxane (82 ml) and DMF (21 ml). DMEDA (1.5 ml, 14 mmol) was then added and the mixture was stirred overnight at 110° C. After cooling to rt, the mixture was combined with a mixture from a test reaction that had been obtained under similar conditions starting from 42 mg 1-(benzylsulfanyl)-3-bromo-2-methylbenzene. The combined mixtures were filtered over Celite, washed with ethyl acetate and the solvent was removed under reduced pressure. The residue was dissolved in ethyl acetate and water and filtered over Celite again. The phases were separated and the aqueous phase was extracted three times with ethyl acetate. The combined organic phases were washed with saturated sodium chloride solution, dried over sodium sulfate and concentrated. The residue was purified by flash-chromatography (Biotage Isolera, silica cartridge, cyclohexane/ethyl acetate gradient) to give the title compound (2.27 g, 54% of theory, 79% purity). The yield is based on the combined experiments.

LC-MS (Method 9): $R_t$=1.18 min; MS (ESIpos): m/z=314 [M+H]$^+$ $^1$H NMR (600 MHz, DMSO-d$_6$) δ [ppm]: 7.42 (d, 2H), 7.38-7.33 (m, 3H), 7.31-7.27 (m, 1H), 7.25 (t, 1H), 7.08 (d, 1H), 5.69 (d, 1H), 4.34-4.30 (m, 1H), 4.27 (s, 2H), 3.63-3.57 (m, 1H), 3.57-3.57 (m, 1H), 2.49-2.42 (m, 1H), 2.09 (s, 3H), 2.02-1.94 (m, 1H).

Intermediate 4

(3S)-1-[3-(Benzylsulfanyl)-2-ethylphenyl]-3-hydroxypyrrolidin-2-one

To a mixture of 1-(benzylsulfanyl)-3-bromo-2-ethylbenzene (4.05 g, 13.19 mmol; for preparation see *Journal of Medicinal Chemistry* 2013, 56, 9441-9456, compound 40b) and (3S)-3-hydroxy-2-pyrrolidinone (4.0 g, 39.56 mmol) in dioxane (105 ml) and DMF (27 ml) under argon were added DMEDA (1.14 ml, 10.55 mmol), copper(I) iodide (2.01 g, 10.55 mmol) and potassium carbonate (7.29 g, 52.75 mmol). The mixture was equally partitioned into 8 microwave vessels and capped. 2 of these vessels were heated in a microwave for 16 h at 110° C., while the other 6 vessels were stirred for 16 h at 110° C. in a heating block. After cooling to rt, the combined mixtures were filtered and the solvent was removed. The residue was taken up in ethyl acetate and water, and after phase separation, the aqueous phase was extracted three times with ethyl acetate. The combined organic phases were washed once with saturated sodium chloride solution, dried over sodium sulfate and concentrated. The residue was adsorbed on Isolute and purified via flash-chromatography (Biotage Isolera, 100 g SNAP-Ultra silicagel, cyclohexane-ethylacetate gradient). The combined product fractions were concentrated and dried in vacuo to give the title compound (2.17 g, 49% of theory, 98% purity).

LC-MS (Method 8): $R_t$=0.92 min; MS (ESIpos): m/z=328 [M+H]$^+$ $^1$H NMR (600 MHz, DMSO-d$_6$) δ [ppm]: 7.41-7.36 (m, 3H), 7.34-7.29 (m, 2H), 7.28-7.20 (m, 2H), 7.01 (dd, 1H), 5.69 (d, 1H), 4.30-4.24 (m, 3H), 3.58-3.52 (m, 1H), 3.50-3.42 (m, 1H), 2.60-2.47 (m, 2H, partially obscured), 2.45-2.36 (m, 1H), 1.98-1.87 (m, 1H), 1.01 (t, 3H).

Intermediate 5

(3R)-1-[3-(Benzylsulfanyl)-2-ethylphenyl]-3-hydroxypyrrolidin-2-one

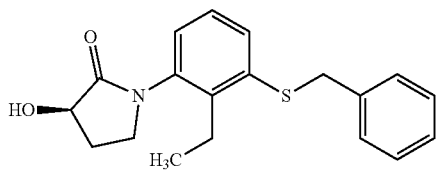

To 1-(benzylsulfanyl)-3-bromo-2-ethylbenzene (844 mg, 2.75 mmol; for preparation see *Journal of Medicinal Chemistry* 2013, 56, 9441-9456, compound 40b) under argon were added (3R)-3-hydroxy-2-pyrrolidinone (500 mg, 4.95 mmol), copper(I) iodide (733 mg, 3.85 mmol), potassium carbonate (1.52 g, 11.0 mmol), dioxane (22 ml), DMF (5.6 ml) and DMEDA (0.41 ml, 3.85 mmol). The mixture was stirred overnight at 110° C. After cooling to rt, the mixtures was filtered over Celite and the solvent was removed. The residue was taken up in ethyl acetate and water, filtered again over Celite, and after phase separation, the aqueous phase was extracted three times with ethyl acetate. The combined organic phases were washed once with saturated sodium chloride solution, dried over sodium sulfate and concentrated. The residue was purified via flash-chromatography (silicagel, cyclohexane-ethylacetate gradient). The combined product fractions were concentrated and dried in vacuo to give the title compound (548 mg, 60% of theory, 99% purity).

LC-MS (Method 7): $R_t$=1.78 min; MS (ESIpos): m/z=328 [M+H]$^+$ $^1$H NMR (600 MHz, DMSO-d$_6$) δ [ppm]: 7.41-7.36 (m, 3H), 7.34-7.29 (m, 2H), 7.28-7.20 (m, 2H), 7.01 (d, 1H), 5.66 (d, 1H), 4.30-4.24 (m, 3H), 3.58-3.52 (m, 1H), 3.50-3.42 (m, 1H), 2.60-2.47 (m, 2H, partially obscured), 2.45-2.36 (m, 1H), 1.98-1.87 (m, 1H), 1.01 (t, 3H).

Intermediate 6

(3S)-1-[3-(Benzylsulfanyl)-2-ethylphenyl]-3-([tert-butyl(dimethyl)silyl]oxy pyrrolidin-2-one

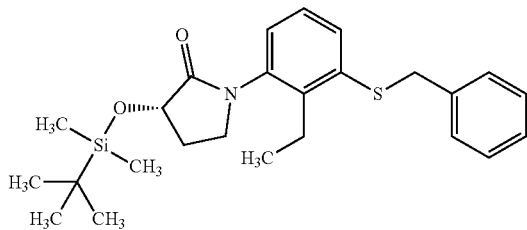 [SMILES: CCc1c(SCc2ccccc2)cccc1N1CC[C@H](O[Si](C)(C)C(C)(C)C)C1=O]

To a solution of (3S)-1-[3-(benzylsulfanyl)-2-ethylphenyl]-3-hydroxypyrrolidin-2-one (2.17 g, 6.64 mmol, Intermediate 4) in DCM (19 ml) and DMF (4.8 ml) were added tert-butyldimethylsilyl chloride (3.0 g, 19.93 mmol), DIPEA (2.9 ml, 16.61 mmol) and DMAP (16 mg, 0.13 mmol) and the mixture was stirred overnight at rt. The mixture was concentrated and the residue was taken up in acetonitrile and water and purified via preparative HPLC (Method 1). The combined product fractions were lyophilized to give the title compound (2.0 g, 68% of theory, 100% purity).

LC-MS (Method 7): $R_t$=2.84 min; MS (ESIpos): m/z=442 [M+H]$^+$ $^1$H NMR (600 MHz, DMSO-d$_6$) δ [ppm]: 7.41-7.36 (m, 3H), 7.34-7.29 (m, 2H), 7.28-7.20 (m, 2H), 7.02 (d, 1H), 4.48 (t, 1H), 4.26 (s, 2H), 3.62-3.53 (m, 1H), 3.53-3.45 (m, 1H), 2.59-2.40 (m, 3H, partially obscured), 2.03-1.90 (m, 1H), 1.01 (t, 3H), 0.9 (s, 9H), 0.13 (s, 3H), 0.12 (s, 3H).

Intermediate 7

2-Ethyl-3-(2-oxopyrrolidin-1-yl)benzene-1-sulfonyl chloride

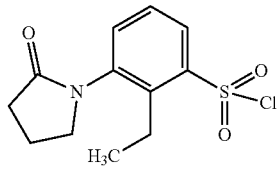

To a solution of 1-[3-(benzylsulfanyl)-2-ethylphenyl]pyrrolidin-2-one (9.30 g, 29.86 mmol, not adjusted for purity, Intermediate 1) in acetic acid (550 ml), sulfurylchoride (9.60 ml, 119.4 mmol) was added and the mixture was stirred for 1 h at rt. Water was added and the mixture was extracted three times with DCM. The combined organic phases were washed three times with saturated sodium chloride solution, dried over sodium sulfate and concentrated. The residue was taken up in cyclohexane and purified via flash chromatography (Biotage Isolera One, 100 g SNAP Ultra silicagel cartridge, cyclohexane/ethyl acetate gradient) to give the title compound (5.15 g, 55% of theory, 91% purity).

LC-MS (Method 7): $R_t$=1.66 min; MS (ESIpos): m/z=288 [M+H]$^+$

Intermediate 8

3-[(3S)-3-Hydroxy-2-oxopyrrolidin-1-yl]-2-methylbenzene-1-sulfonyl chloride

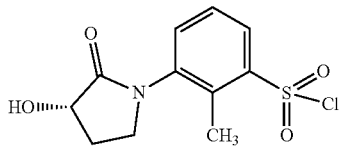 [SMILES: Cc1c(N2CC[C@H](O)C2=O)cccc1S(=O)(=O)Cl]

To a solution of (3S)-1-[3-(benzylsulfanyl)-2-methylphenyl]-3-hydroxypyrrolidin-2-one (4.24 g, 92% purity, 12.45 mmol, Intermediate 2) in DCM (73 ml) and acetic acid (290 ml), NCS (6.65 g, 49.8 mmol) was added and the mixture was stirred at rt for 1 h. Water was added and the mixture was extracted three times with dichloromethane. The combined organic phases were washed three times with saturated sodium chloride solution, dried over sodium sulfate and concentrated. The residue was taken up in DCM and washed three times with saturated sodium chloride solution. The organic phase was dried over sodium sulfate and concentrated, and the residue was dried in vacuo to give the title compound (3.94 g, 80% of theory, 73% purity).

LC-MS (Method 7): $R_t$=1.26 min; MS (ESIpos): m/z=290 [M+H]$^+$.

Intermediate 9

3-[(3R)-3-Hydroxy-2-oxopyrrolidin-1-yl]-2-methyl-benzene-1-sulfonyl chloride

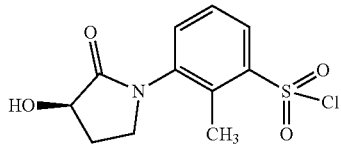 [SMILES: Cc1c(N2CC[C@@H](O)C2=O)cccc1S(=O)(=O)Cl]

To a solution of (3R)-1-[3-(benzylsulfanyl)-2-methylphenyl]-3-hydroxypyrrolidin-2-one (2.27 g, 79% purity, 5.72 mmol, Intermediate 3) in DCM (34 ml) and acetic acid (135 ml), NCS (3.06 g, 22.9 mmol) was added and the mixture was stirred at rt for 1 h. Water was added and the mixture was extracted three times with dichloromethane. The combined organic phases were washed with saturated sodium chloride solution, dried over sodium sulfate and concentrated. The residue was taken up in DCM and washed three times with saturated sodium chloride solution, followed by one reextraction of the combined aqueous phases with DCM. The combined organic phases were dried over sodium sulfate and concentrated, and the residue was dried in vacuo to give the title compound (1.90 g, 62% of theory, 54% purity).

LC-MS (Method 7): $R_t$=1.26 min; MS (ESIpos): m/z=290 [M+H]$^+$.

Intermediate 10

2-Ethyl-3-[(3S)-3-hydroxy-2-oxopyrrolidin-1-yl] benzene-1-sulfonyl chloride

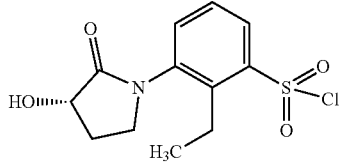 [SMILES: CCc1c(N2CC[C@H](O)C2=O)cccc1S(=O)(=O)Cl]

To a solution of (3S)-1-[3-(benzylsulfanyl)-2-ethylphenyl]-3-{[tert-butyl(dimethyl)silyl]oxy}-pyrrolidin-2-one (2.0 g, 4.53 mmol, Intermediate 6) in acetic acid (120 ml) was added sulfuryl chloride (1.50 ml, 18.1 mmol) and the mixture was stirred at rt for 1 h. The mixture was diluted with water and extracted five times with DCM, after which the aqeuous phase was saturated with sodium chloride and extracted again with DCM. The combined organic phases were dried over sodium sulfate and concentrated via rotary evaporator at a bath temperature of 25° C. The residue was purified in two portions via flash-chromatography (Biotage Isolera, 100 g SNAP-Ultra silicagel, cyclohexane-ethylacetate gradient). The combined product fractions were concentrated via rotary evaporator at a bath temperature of 25° C. to give the title compound (1.11 g, 72% of theory, 90% purity according to LC-MS).

LC-MS (Method 7): $R_t$=1.39 min; MS (ESIpos): m/z=304 [M+H]$^+$.

Intermediate 11

2-Ethyl-3-[(3R)-3-hydroxy-2-oxopyrrolidin-1-yl] benzene-1-sulfonyl chloride

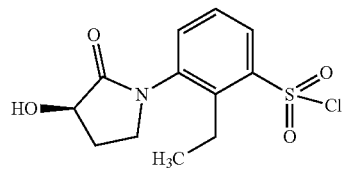 [SMILES: CCc1c(N2CC[C@@H](O)C2=O)cccc1S(=O)(=O)Cl]

To a solution of (3R)-1-[3-(benzylsulfanyl)-2-ethylphenyl]-3-hydroxypyrrolidin-2-one (545 mg, 1.65 mmol, Intermediate 5) in DCM (10 ml) and acetic acid (39 ml) was added NCS (880 mg, 6.59 mmol) and the mixture was stirred at rt for 1 h. Then, the mixture was diluted with water and extracted three times with DCM. The combined organic phases were washed three times with saturated sodium chloride solution, dried over sodium sulfate and concentrated via rotary evaporator at a bath temperature of 25° C. The residue was purified via flash-chromatography (Biotage Isolera, SNAP-Ultra silicagel, cyclohexane-ethylacetate gradient). The combined product fractions were concentrated via rotary evaporator at a bath temperature of 25° C. to give the title compound (450 mg, 84% of theory, 93% purity according to NMR, containing some solvent).

LC-MS (Method 7): $R_t$=1.39 min; MS (ESIpos): m/z=304 [M+H]$^+$ $^1$H NMR (600 MHz, DMSO-d$_6$) δ [ppm]: 7.80 (dd, 1H), 7.21-7.16 (m, 1H), 7.13 (dd, 1H), 4.27 (t, 1H), 3.63-3.57 (m, 1H), 3.55-3.46 (m, 1H), 3.02-2.87 (m, 2H), 2.46-2.38 (m, 1H), 1.97-1.89 (m, 1H), 1.05 (t, 3H).

Intermediate 12

Methyl 3-[(5-chlorothiophene-2-carbonyl)amino]-N-{3-[(3S)-3-hydroxy-2-oxopyrrolidin-1-yl]-2-methyl-benzene-1-sulfonyl}-S-alaninate

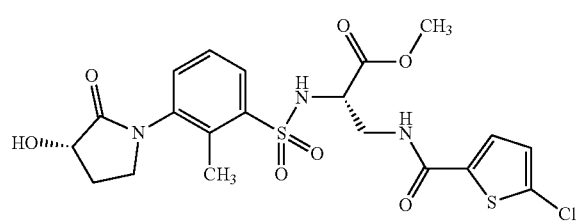 [SMILES: COC(=O)[C@H](CNC(=O)c1ccc(Cl)s1)NS(=O)(=O)c1cccc(N2CC[C@H](O)C2=O)c1C]

To a solution of 3-[(3S)-3-hydroxy-2-oxopyrrolidin-1-yl]-2-methylbenzene-1-sulfonyl chloride (3.69 g, 7.39 mmol, 58% purity, Intermediate 8) in DCM (91 ml) were added triethylamine (4.1 ml, 29.55 mmol) and methyl-3-{[(5-chlor-2-thienyl)carbonyl]amino}-S-alaninate (2.04 g, 7.76 mmol; for preparation see *Journal of Medicinal Chemistry* 2013, 56, 9441-9456, compound 49), and the reaction mixture was stirred at rt for 1.5 h. The mixture was combined with a mixture from a smaller-scale reaction that had been obtained under similar conditions, starting from 250 mg (94% purity) of 3-[(3S)-3-hydroxy-2-oxopyrrolidin-1-yl]-2-methylbenzene-1-sulfonyl chloride. The combined mixtures were diluted with DCM and washed twice with water, followed by reextraction of the combined aqueous phases with DCM. The organic phase was then washed with saturated sodium chloride solution, dried and concentrated. The residue was purified via flash-chromatography (silicagel, DCM/methanol 20:1) to give the title compound (2.25 g, 46% of theory, 87% purity). The yield is based on the combined experiments.

LC-MS (Method 9): $R_t$=0.99 min; MS (ESIneg): m/z=514 [M−H]$^-$.

Intermediate 13

Methyl 3-[(5-chlorothiophene-2-carbonyl)amino]-N-{3-[(3R)-3-hydroxy-2-oxopyrrolidin-1-yl]-2-methyl-benzene-1-sulfonyl}-S-alaninate

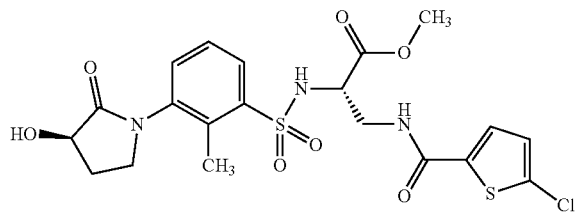 [SMILES: COC(=O)[C@H](CNC(=O)c1ccc(Cl)s1)NS(=O)(=O)c1cccc(N2CC[C@@H](O)C2=O)c1C]

To a solution of 3-[(3R)-3-hydroxy-2-oxopyrrolidin-1-yl]-2-methylbenzene-1-sulfonyl chloride (1.90 g, 54% purity, 3.54 mmol, Intermediate 9) in DCM (44 ml) were added triethylamine (2.0 ml, 14.2 mmol) and methyl-3-{[(5-chlor-2-thienyl)carbonyl]amino}-S-alaninate (0.98 g, 3.72 mmol; for preparation see *Journal of Medicinal Chemistry* 2013, 56, 9441-9456, compound 49), and the reaction mixture was stirred at rt for 1.5 h. The mixture was diluted with DCM and washed twice with water, followed by reextraction of the combined aqueous phases with DCM. The organic phase was then washed with saturated sodium chloride solution, dried and concentrated. The residue was purified via flash-chromatography (silicagel, DCM/methanol gradient) to give the title compound (882 mg, 46% of theory, 96% purity).

LC-MS (Method 9): $R_t$=0.99 min; MS (ESIneg): m/z=514 [M−H]$^-$.

Intermediate 14

Lithium (2S)-3-{[(5-chloro-2-thienyl)carbonyl]amino}-2-({[2-ethyl-3-(2-oxopyrrolidin-1-yl)-phenyl]sulfonyl}amino)propanoate

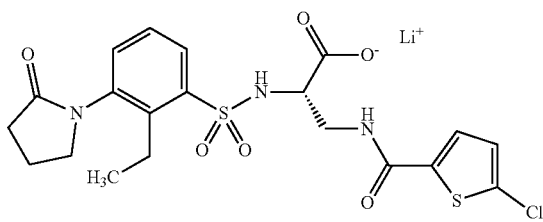 [SMILES: CCc1c(N2CCCC2=O)cccc1S(=O)(=O)N[C@@H](CNC(=O)c1ccc(Cl)s1)C(=O)[O-] ; [Li+]]

To a solution of methyl 3-[(5-chlorothiophene-2-carbonyl)amino]-N-[2-ethyl-3-(2-oxopyrrolidin-1-yl)benzene-1-sulfonyl]-S-alaninate (2.0 g, 3.89 mmol, Reference 5) in THF (30 ml) were added lithium hydroxide monohydrate (816 mg, 19.45 mmol) and the mixture was stirred at rt for 4 h. The mixture was then concentrated and the residue was taken up in water/methanol/acetonitril and purified via preparative HPLC (Method 3). The combined product fractions were concentrated and the residue was dried in vacuo to give the title compound (1.56 g, 80% of theory, 100% purity).

LC-MS (Method 7): $R_t$=1.38 min; MS (ESIpos): m/z=500 [M+H]$^+$ $^1$H NMR (600 MHz, DMSO-d$_6$) δ [ppm]: 8.65 (br s, 1H), 7.91 (d, 1H), 7.47 (d, 1H), 7.43 (d, 1H), 7.36 (t, 1H), 7.15 (d, 1H), 3.65 (br s, 2H), 3.57-3.48 (m, 1H), 3.38-3.27 (obscured, 2H), 2.98-2.88 (m, 1H), 2.88-2.80 (m, 1H), 2.42 (t, 2H), 2.17-2.08 (m, 2H), 1.08 (t, 3H).

Intermediate 15

3-[(5-Chlorothiophene-2-carbonyl)amino]-N-[2-ethyl-3-(2-oxopyrrolidin-1-yl)benzene-1-sulfonyl]-S-alanine

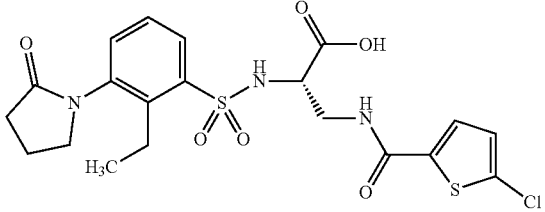 [SMILES: CCc1c(N2CCCC2=O)cccc1S(=O)(=O)N[C@@H](CNC(=O)c1ccc(Cl)s1)C(=O)O]

To a solution of methyl 3-[(5-chlorothiophene-2-carbonyl)amino]-N-[2-ethyl-3-(2-oxopyrrolidin-1-yl)benzene-1-sulfonyl]-S-alaninate (515 mg, 1.00 mmol, Reference 5) in THF (5 ml) was added 1 M lithium hydroxide solution (5.0 ml, 5.0 mmol) and the mixture was stirred at rt for 2 h. Then, the mixture was diluted with water and washed with diethyl ether. The aqueous phase was then treated with 1 M hydrochloric acid (6 ml) and extracted three times with butanol. The combined butanol phases were were concentrated and the residue was taken up in acetonitril/water and lyophilized to give the title compound (482 mg, 90% of theory, 94% purity).

LC-MS (Method 7): $R_t$=1.38 min; MS (ESIpos): m/z=500 [M+H]$^+$ $^1$H NMR (600 MHz, DMSO-d$_6$) δ [ppm]: 12.84 (s, 1H), 8.68 (t, 1H), 8.44 (d, 1H), 7.85 (d, 1H), 7.55 (d, 1H), 7.41 (d, 1H), 7.32 (t, 1H), 7.17 (d, 1H), 4.00 (dd, 1H), 3.66-3.57 (br m, 2H), 3.57-3.50 (m, 1H), 3.43-3.36 (m, 1H), 2.93-2.80 (m, 2H), 2.42 (t, 2H), 2.16-2.09 (m, 2H), 1.08 (t, 3H).

Intermediate 16

3-[(5-Chlorothiophene-2-carbonyl)amino]-N-{3-[(3S)-3-hydroxy-2-oxopyrrolidin-1-yl]-2-methylbenzene-1-sulfonyl}-S-alanine

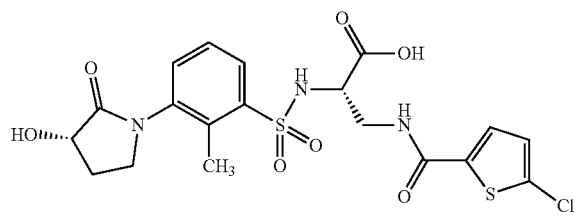 [SMILES: Cc1c(N2CC[C@H](O)C2=O)cccc1S(=O)(=O)N[C@@H](CNC(=O)c1ccc(Cl)s1)C(=O)O]

To a solution of methyl 3-[(5-chlorothiophene-2-carbonyl)amino]-N-{3-[(3S)-3-hydroxy-2-oxopyrrolidin-1-yl]-2-methylbenzene-1-sulfonyl}-S-alaninate (2.25 g, 87% purity, 3.79 mmol, Intermediate 12) in THF (8.1 ml) was added aqueous lithium hydroxide solution (38 ml, 1.0 M, 38 mmol) and the mixture was stirred at rt for 2 h. After evaporation of THF, the aqueous mixture was acidified slowly with 2 M hydrochloric acid until a pH value of 1 was reached. The resulting mixture was extracted twice with ethyl acetate and the combined organic phases were dried over sodium sulfate, concentrated and dried in vacuo to give the title compound (1.96 g, 97% of theory, 94% purity, containing some solvent according to NMR).

LC-MS (Method 9): $R_t$=0.89 min; MS (ESIpos): m/z=502 [M+H]$^+$ $^1$H NMR (600 MHz, DMSO-d$_6$) δ [ppm]: 12.84 (br s, 1H), 8.55 (t, 1H), 8.35 (d, 1H), 7.81 (d, 1H), 7.48 (d, 1H), 7.40 (d, 1H), 7.31 (t, 1H), 7.15 (d, 1H), 5.70 (d, 1H), 4.33-4.28 (m, 1H), 4.02-3.97 (m, 1H), 3.58-3.49 (m, 2H), 3.49-3.41 (m, 1H), 3.38-3.30 (m, 1H, partially obscured), 2.47-2.39 (m, 1H), 2.35 (s, 3H), 1.97-1.89 (m, 1H).

Intermediate 17

3-[(5-Chlorothiophene-2-carbonyl)amino]-N-{3-[(3R)-3-hydroxy-2-oxopyrrolidin-1-yl]-2-methylbenzene-1-sulfonyl}-S-alanine

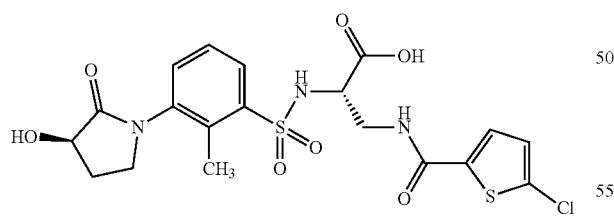

To a solution of methyl 3-[(5-chlorothiophene-2-carbonyl)amino]-N-{3-[(3R)-3-hydroxy-2-oxopyrrolidin-1-yl]-2-methylbenzene-1-sulfonyl}-S-alaninate (882 mg, 1.71 mmol, Intermediate 13) in THF (3.6 ml) was added aqueous lithium hydroxide solution (17 ml, 1.0 M, 17 mmol) and the mixture was stirred at rt for 2 h. After evaporation of THF, the aqueous mixture was acidified slowly with 2 M hydrochloric acid until a pH value of 1 was reached. The resulting mixture was extracted twice with ethyl acetate and the combined organic phases were dried over sodium sulfate, concentrated and dried in vacuo to give the title compound (784 mg, 81% of theory, 89% purity, containing some solvent according to NMR).

LC-MS (Method 9): $R_t$=0.89 min; MS (ESIpos): m/z=502 [M+H]$^+$ $^1$H NMR (600 MHz, DMSO-d$_6$) δ [ppm]: 12.76 (br s, 1H), 8.57 (t, 1H), 8.36 (d, 1H), 7.82 (d, 1H), 7.50 (d, 1H), 7.42 (d, 1H), 7.32 (t, 1H), 7.16 (d, 1H), 5.70 (d, 1H), 4.31 (br t, 1H), 4.02-3.97 (m, 1H), 3.58-3.50 (m, 2H), 3.50-3.44 (m, 1H), 3.39-3.33 (m, 1H), 2.47-2.39 (m, 1H), 2.36 (s, 3H), 1.98-1.92 (m, 1H).

Intermediate 18

Lithium (2S)-3-{[(5-chloro-2-thienyl)carbonyl]amino}-2-[({2-ethyl-3-[(3S)-3-hydroxy-2-oxo-pyrrolidin-1-yl]phenyl}sulfonyl)amino]propanoate

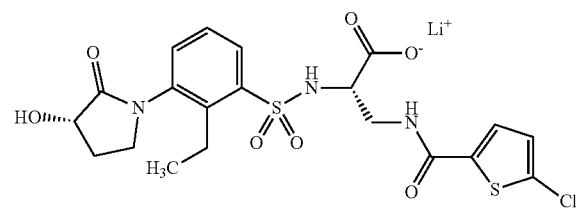 [SMILES: CCc1c(N2CC[C@H](O)C2=O)cccc1S(=O)(=O)N[C@@H](CNC(=O)c1ccc(Cl)s1)C(=O)[O-] ; [Li+]]

To a solution of methyl 3-[(5-chlorothiophene-2-carbonyl)amino]-N-{2-ethyl-3-[(3S)-3-hydroxy-2-oxopyrrolidin-1-yl]benzene-1-sulfonyl}-S-alaninate (200 mg, 0.38 mmol, Reference 6) in THF (2.1 ml) were added lithium hydroxide monohydrate (48 mg, 1.13 mmol) and two drops of water and the mixture was stirred for 1 h at rt. The mixture was then concentrated and the residue was purified via preparative HPLC (Method 1). The combined product fractions were lyophilized to give the title compound (140 mg, 71% of theory, 100% purity).

LC-MS (Method 7): $R_t$=1.23 min; MS (ESIpos): m/z=516 [M+H]$^+$ $^1$H NMR (600 MHz, DMSO-d$_6$) δ [ppm]: 8.70-8.64 (m, 1H), 7.93 (d, 1H), 7.47-7.40 (m, 2H), 7.40-7.34 (m, 1H), 7.16 (d, 1H), 5.75 (br s, 1H), 4.28 (t, 1H), 3.65-3.57 (m, 1H), 3.56-3.47 (m, 2H), 3.38-3.20 (m, 4H, partially obscured), 2.98-2.76 (m, 2H), 2.47-2.38 (m, 1H), 2.00-1.87 (m, 1H), 1.07 (t, 1H).

Intermediate 19

3-[(5-Chlorothiophene-2-carbonyl)amino]-N-{2-ethyl-3-[(3S)-3-hydroxy-2-oxopyrrolidin-1-yl]benzene-1-sulfonyl}-S-alanine

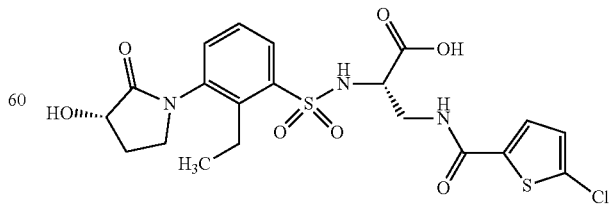

To a solution of methyl 3-[(5-chlorothiophene-2-carbonyl)amino]-N-{2-ethyl-3-[(3S)-3-hydroxy-2-oxopyrrolidin- 1-yl]benzene-1-sulfonyl}-S-alaninate (508 mg, 0.96 mmol, Reference 6) in THF (2.0 ml) was added aqueous lithium hydroxide solution (1 M, 9.6 ml, 9.6 mmol) and the mixture was stirred for 2 h at rt. After evaporation of THF, the aqueous mixture was acidified slowly with 1 M hydrochloric acid until a pH value of 1 was reached. The resulting mixture was extracted twice with ethyl acetate and the combined organic phases were dried over sodium sulfate, concentrated and dried in vacuo to give the title compound (391 mg, 75% of theory, 95% purity), containing some solvent according to HNMR.

LC-MS (Method 8): $R_t$=0.65 min; MS (ESIpos): m/z=516 [M+H]$^+$

Chiral HPLC (Method 10): $R_t$=7.76 min $^1$H NMR (600 MHz, DMSO-d$_6$) δ [ppm]: 12.83 (br s, 1H), 8.60 (t, 1H), 8.40 (d, 1H), 7.86 (dd, 1H), 7.52 (d, 1H), 7.39 (dd, 1H), 7.33 (t, 1H), 7.16 (d, 1H), 5.70 (d, 1H), 4.32-4.26 (m, 1H), 4.05-4.00 (m, 1H), 3.59-3.51 (m, 2H), 3.49-3.36 (m, 2H), 2.91-2.81 (m, 2H), 2.47-2.37 (m, 1H), 1.97-1.87 (m, 1H), 1.06 (t, 3H).

Intermediate 20

3-[(5-Chlorothiophene-2-carbonyl)amino]-N-{2-ethyl-3-[(3R)-3-hydroxy-2-oxopyrrolidin-1-yl]benzene-1-sulfonyl}-S-alanine

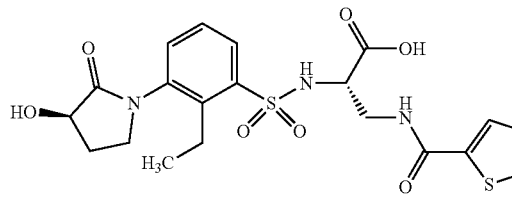

To a solution of methyl 3-[(5-chlorothiophene-2-carbonyl)amino]-N-{2-ethyl-3-[(3R)-3-hydroxy-2-oxopyrrolidin-1-yl]benzene-1-sulfonyl}-S-alaninate (620 mg, 95% purity, 1.11 mmol, Reference 7) in THF (2.4 ml) was added aqueous lithium hydroxide solution (11 ml, 1.0 M, 11 mmol) and the mixture was stirred for 2 h at rt. After evaporation of THF, the aqueous mixture was acidified slowly with 1 M hydrochloric acid until a pH value of 1 was reached. The resulting mixture was extracted twice with ethyl acetate and the combined organic phases were dried over sodium sulfate, concentrated and dried in vacuo to give the title compound (570 mg, 99% of theory, 100% purity, containing some solvent according to NMR).

LC-MS (Method 7): $R_t$=1.21 min; MS (ESIpos): m/z=516 [M+H]$^+$

Chiral HPLC (Method 10): $R_t$=6.31 min $^1$H NMR (600 MHz, DMSO-d$_6$) δ [ppm]: 12.90 (br s, 1H), 8.61 (t, 1H), 8.40 (d, 1H), 7.87 (dd, 1H), 7.54 (d, 1H), 7.40 (d, 1H), 7.33 (t, 1H), 7.17 (d, 1H), 5.71 (br s, 1H), 4.29 (br t, 1H), 4.06-3.99 (m, 1H), 3.61-3.50 (m, 2H), 3.49-3.44 (m, 1H), 3.44-3.37 (m, 1H), 2.94-2.80 (m, 2H), 2.48-2.40 (m, 1H), 1.97-1.91 (m, 1H), 1.07 (t, 3H).

REFERENCE COMPOUNDS

Reference 1

5-Chloro-N-[(2S)-2-({[2-methyl-3-(2-oxopyrrolidin-1-yl)phenyl]sulfonyl}amino)-3-(4-methyl-piperazin-1-yl)-3-oxopropyl]thiophene-2-carboxamide hydrochloride

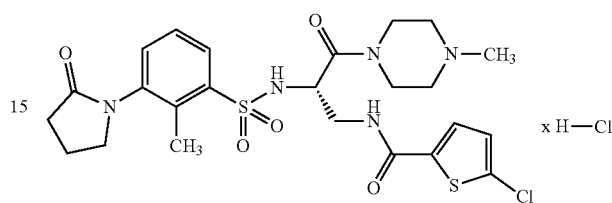

For preparation see *Journal of Medicinal Chemistry* 2013, 56, 9441-9456, compound 15.

Reference 2

2-(Dimethylamino)ethyl 3-{[(5-chloro-2-thienyl)carbonyl]amino}-N-{[2-methyl-3-(2-oxopyrrolidin-1-yl)phenyl]sulfonyl}-S-alaninate hydrochloride

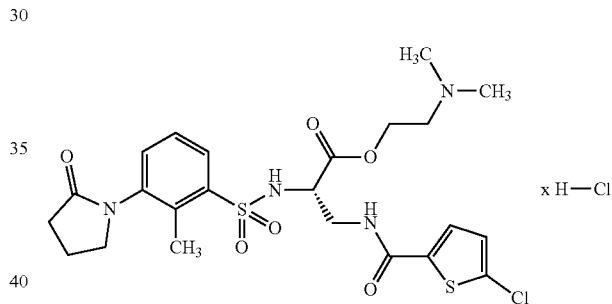

To a solution of 3-{[(5-chloro-2-thienyl)carbonyl]amino}-N-{[2-methyl-3-(2-oxopyrrolidin-1-yl)-phenyl]sulfonyl}-S-alanine (150 mg, 0.31 mmol, for preparation see *Journal of Medicinal Chemistry* 2013, 56, 9441-9456, compound 51) in THF (1.5 ml) were added HBTU (140 mg, 0.37 mmol, CAS-RN 94790-37-1), DIPEA (0.16 ml, 0.93 mmol) and 2-(dimethylamino)ethanol (37 µl, 370 µmol), and the mixture was stirred for 1 h at rt. Then, the mixture was concentrated via rotary evaporator and the residue was taken up in acetonitrile/water and purified via preparative HPLC with TFA added to the mobile phase (Method 5). After lyophilization, a TFA-containing batch was obtained. For generation of the corresponding hydrochloride, the TFA-containing batch was first dissolved in acetonitrile/water and the solution was stirred for 1 h with chloride ion exchanger resin (2.0 g amberlite IRA405 Cl). Afterwards, the solution was purified via preparative HPLC with hydrogen chloride added to the mobile phase (Method 6) to give a first batch of the title compound (96 mg, 52% of theory, 100% purity) and a second batch of the title compound (6 mg, 3% of theory, 94% purity).

LC-MS (Method 7): $R_t$=0.99 min; MS (ESIpos): m/z=557 [M+H]$^+$ $^1$H NMR (600 MHz, DMSO-d$_6$) δ [ppm]: 10.28 (br s, 1H), 8.92 (t, 1H), 8.74 (d, 1H), 7.81 (d, 1H), 7.66 (d, 1H), 7.48 (d, 1H), 7.37 (t, 1H), 7.19 (d, 1H), 4.24-4.18 (m, 1H), 4.16-4.08 (m, 2H), 3.68-5.57 (m, 3H), 3.52-3.45 (m, 1H), 3.23 (m, 2H), 2.75 (d, 3H), 2.73 (d, 3H), 2.45 (t, 2H), 2.39 (s, 3H), 2.18-2.11 (m, 2H).

IC: 6.0 wt % chloride, <1 wt % TFA

Reference 3

1-Methylpiperidin-4-yl 3-{[(5-chloro-2-thienyl)carbonyl]amino}-N-{[2-methyl-3-(2-oxopyrrolidin-1-yl)phenyl]sulfonyl}-S-alaninate hydrochloride

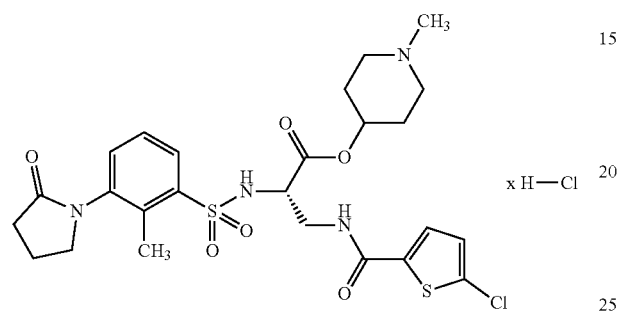

To a solution of 3-{[(5-chloro-2-thienyl)carbonyl]amino}-N-{[2-methyl-3-(2-oxopyrrolidin-1-yl)-phenyl]sulfonyl}-S-alanine (150 mg, 0.31 mmol, for preparation see *Journal of Medicinal Chemistry* 2013, 56, 9441-9456, compound 51) in THF (1.5 ml) were added TBTU (119 mg, 0.37 mmol, CAS-RN 125700-67-6), DIPEA (0.16 ml, 0.93 mmol) and N-methyl-4-piperidinol (44 µl, 370 µmol), and the mixture was stirred overnight at rt. Then, the mixture was purified via preparative HPLC with hydrogen chloride added to the mobile phase (Method 6) to give the title compound (28 mg, 14% of theory, 100% purity).

LC-MS (Method 7): $R_t$=1.00 min; MS (ESIpos): m/z=583 [M+H]$^+$ $^1$H NMR (600 MHz, DMSO-d$_6$) δ [ppm]: 10.28 (br s, 1H), 8.86 and 8.81 (2×t, 1H), 8.75 and 8.74 (2×d, 1H), 7.83 and 7.81 (2×d, 1H), 7.62 and 7.58 (2×d, 1H), 7.49-7.45 (m, 1H), 7.39-7.34 (m, 1H), 7.19-7.17 (m, 1H), 4.83-4.78 and 4.65-4.59 (2×m, 1H), 4.14-4.08 and 4.04-3.98 (2×m, 1H), 3.66-3.13 (3×m, 6H, partially obscured), 3.03-2.89 (m, 2H), 2.69-2.65 (m, 3H), 2.47-2.41 (m, 2H), 2.37 (s, 3H), 2.18-2.11 (m, 2H), 1.97-1.73 (2×m, 2H), 1.67-1.50 (m, 2H).

IC: 5.6 wt % chloride

Reference 4

Methyl 3-{[(5-chloro-2-thienyl)carbonyl]amino}-N-{[2-methyl-3-(2-oxopyrrolidin-1-yl)phenyl]-sulfonyl}-S-alaninate

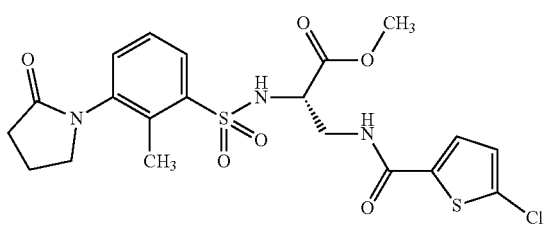 [SMILES: COC(=O)[C@H](CNC(=O)c1ccc(Cl)s1)NS(=O)(=O)c1cccc(N2CCCC2=O)c1C]

For preparation see *Journal of Medicinal Chemistry* 2013, 56, 9441-9456, compound 50.

Reference 5

Methyl 3-[(5-chlorothiophene-2-carbonyl)amino]-N-[2-ethyl-3-(2-oxopyrrolidin-1-yl)benzene-1-sulfonyl]-S-alaninate

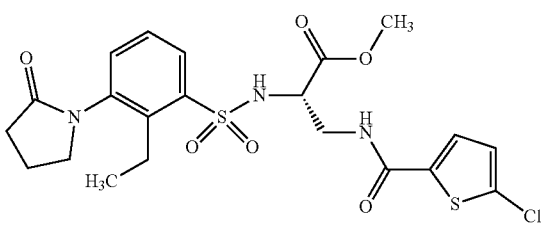 [SMILES: CCc1c(N2CCCC2=O)cccc1S(=O)(=O)N[C@@H](CNC(=O)c1ccc(Cl)s1)C(=O)OC]

To a mixture of 2-ethyl-3-(2-oxopyrrolidin-1-yl)benzene-1-sulfonyl chloride (5.15 g, 17.90 mmol, Intermediate 7) in DCM (215 ml) were added methyl-3-{[(5-chloro-2-thienyl)carbonyl]amino}-S-alaninate hydrochloride (5.89 g, 19.7 mmol, for preparation see *Journal of Medicinal Chemistry* 2013, 56, 9441-9456, compound 49) and triethyl amine (5.0 ml, 35.8 mmol) and the mixture was stirred for 1 h at rt. Then, the mixture was concentrated and the residue was purified via flash chromatography (Biotage Isolera, 100 g SNAP-Ultra silicagel, DCM/methanol gradient). The combined product fractions were concentrated and dried in vacuo to give a first batch of the title compound (8.35 g, 86% of theory, 95% purity) and a second batch of the title compound (830 mg, 9% of theory, 100% purity).

LC-MS (Method 8): $R_t$=0.85 min; MS (ESIpos): m/z=514 [M+H]$^+$ $^1$H NMR (400 MHz, DMSO-d$_6$) δ [ppm]: 8.68 (t, 1H), 8.63 (d, 1H), 7.81 (dd, 1H), 7.54 (d, 1H), 7.45 (dd, 1H), 7.37 (t, 1H), 7.18 (d, 1H), 4.12-4.00 (m, 1H), 3.73-3.49 (m, 3H), 3.46-3.35 (m, 4H), 2.98-2.74 (m, 2H), 2.43 (t, 2H), 2.19-2.08 (m, 2H), 1.08 (t, 3H).

Reference 6

Methyl 3-[(5-chlorothiophene-2-carbonyl)amino]-N-{2-ethyl-3-[(3S)-3-hydroxy-2-oxopyrrolidin-1-yl]benzene-1-sulfonyl}-S-alaninate

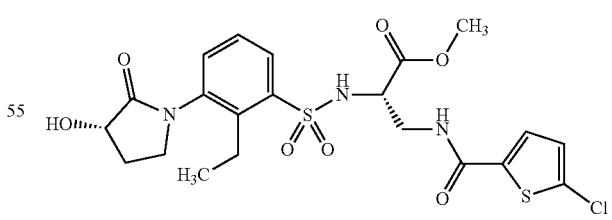

To a mixture of 2-ethyl-3-[(3S)-3-hydroxy-2-oxopyrrolidin-1-yl]benzene-1-sulfonyl chloride (1.11 g, 3.66 mmol, Intermediate 10) in DCM (45 ml) were added methyl-3-{[(5-chloro-2-thienyl)carbonyl]amino}-S-alaninate hydrochloride (1.64 g, 5.50 mmol, for preparation see *Journal of Medicinal Chemistry* 2013, 56, 9441-9456, compound 49) and triethyl amine (1.0 ml, 7.32 mmol) and the mixture was stirred for 2 h at rt. The mixture was then concentrated and the residue was adsorbed on Isolute and purified via flash-chromatography (Biotage Isolera, 50 g SNAP-Ultra silicagel, cyclohexane/ethyl acetate/methanol gradient). The combined product fractions were concentrated and dried in vacuo to give the title compound (892 mg, 44% of theory, 96% purity according to LC-MS).

LC-MS (Method 7): $R_t$=1.42 min; MS (ESIpos): m/z=530 [M+H]$^+$ $^1$H NMR (600 MHz, DMSO-d6) δ[ppm]: 8.71-8.62 (m, 2H), 7.85-7.80 (m, 1H), 7.54 (d, 1H), 7.46-7.42 (m, 1H), 7.40-7.34 (m, 1H), 7.17 (d, 1H), 5.76-5.74 (m, 1H), 4.34-4.27 (m, 1H), 4.11-4.00 (m, 1H), 3.68-3.34 (m, 7H), 2.95-2.77 (m, 2H), 2.48-2.39 (m, 1H), 2.00-1.88 (m, 1H), 1.07 (t, 3H).

Reference 7

Methyl 3-[(5-chlorothiophene-2-carbonyl)amino]-N-{2-ethyl-3-[(3R)-3-hydroxy-2-oxopyrrolidin-1-yl]benzene-1-sulfonyl}-S-alaninate

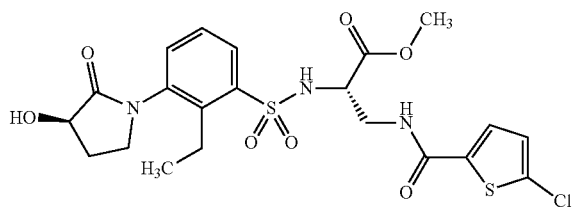 [SMILES: CCc1c(N2CC[C@@H](O)C2=O)cccc1S(=O)(=O)N[C@@H](CNC(=O)c1ccc(Cl)s1)C(=O)OC]

To a mixture of 2-ethyl-3-[(3R)-3-hydroxy-2-oxopyrrolidin-1-yl]benzene-1-sulfonyl chloride (445 mg, 93% purity, 1.36 mmol, Intermediate 11) in DCM (17 ml) were added triethyl amine (0.63 ml, 4.5 mmol) and methyl-3-{[(5-chloro-2-thienyl)carbonyl]amino}-S-alaninate hydrochloride (481 mg, 1.61 mmol, for preparation see *Journal of Medicinal Chemistry* 2013, 56, 9441-9456, compound 49) and the mixture was stirred for 15 min at rt. More methyl-3-{[(5-chloro-2-thienyl)carbonyl]amino}-S-alaninate hydrochloride (45 mg, 0.15 mmol) was added and the mixture was stirred at rt for another 10 minutes. Then, water was added and the phases were separated. The aqueous phase was extracted twice with DCM. The combined organic phases were washed with saturated sodium chloride solution, dried over sodium sulfate and concentrated. The residue was purified via flash-chromatography (silicagel, ethyl acetate/methanol gradient). The combined product fractions concentrated and dried in vacuo to give the title compound (620 mg, 82% of theory, 95% purity according to NMR).

LC-MS (Method 7): $R_t$=1.40 min; MS (ESIpos): m/z=530 [M+H]$^+$ $^1$H NMR (600 MHz, DMSO-d$_6$) δ [ppm]: 8.65 (t, 1H), 8.61 (d, 1H), 7.83 (d, 1H), 7.54 (d, 1H), 7.44 (d, 1H), 7.38 (t, 1H), 7.17 (d, 1H), 5.71 (d, 1H), 4.33-4.27 (m, 1H), 4.10-4.04 (m, 1H), 3.62-3.48 (m, 3H), 3.45-3.38 (m, 4H), 2.95-2.87 (m, 1H), 2.86-2.77 (m, 1H), 2.47-2.40 (m, 1H), 2.00-1.91 (m, 1H), 1.07 (t, 3H).

Reference 8

2-(1-Methyl-1H-imidazol-2-yl)ethyl 3-{[(5-chloro-2-thienyl)carbonyl]amino}-N-{[2-methyl-3-(2-oxopyrrolidin-1-yl)phenyl]sulfonyl}-S-alaninate

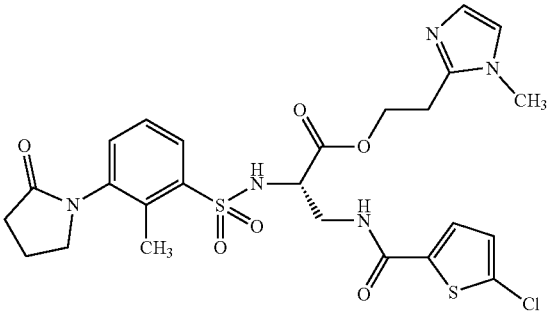 [SMILES: Cc1c(N2CCCC2=O)cccc1S(=O)(=O)N[C@@H](CNC(=O)c1ccc(Cl)s1)C(=O)OCCc1nccn1C]

To a solution of 3-{[(5-chloro-2-thienyl)carbonyl]amino}-N-{[2-methyl-3-(2-oxopyrrolidin-1-yl)-phenyl]sulfonyl}-S-alanine (150 mg, 0.31 mmol, for preparation see *Journal of Medicinal Chemistry* 2013, 56, 9441-9456, compound 51) in THF (3.0 ml) were added HBTU (211 mg, 0.56 mmol, CAS-RN 94790-37-1), DIPEA (108 µl, 0.62 mmol) and 2-(1-methyl-1H-imidazol-2-yl)ethanol (117 mg, 0.93 mmol, CAS-RN 18994-70-2), and the mixture was stirred overnight at rt. Then, the mixture was taken up in water/acetonitrile and purified via preparative HPLC (Method 4). The combined product fractions were concentrated and the residue was lyophilized. The lyophilizate was dissolved in ethyl acetate and the solution was washed several times with saturated sodium hydrogencarbonate solution, dried over sodium sulfate and concentrated. The resulting residue was dried in vacuo to give the title compound (31 mg, 17% of theory, purity 100%).

LC-MS (Method 7): $R_t$=1.08 min; MS (ESIpos): m/z=594 [M+H]$^+$ $^1$H NMR (600 MHz, DMSO-d$_6$) δ [ppm]: 13.94 (br s, 1H), 8.65 (t, 1H), 8.59 (d, 1H), 7.75 (dd, 1H), 7.58 (d, 1H), 7.54 (d, 1H), 7.48 (d, 1H), 7.44 (dd, 1H), 7.32 (t, 1H), 7.18 (d, 1H), 4.25-4.15 (m, 2H), 4.06-3.99 (m, 1H), 3.74 (s, 3H), 3.66-3.55 (m, 2H), 3.53-3.44 (m, 1H), 3.40-3.30 (1H, obscured), 3.17 (t, 2H), 2.44 (t, 2H), 2.34 (s, 3H), 2.18-2.10 (m, 2H).

Reference 9

2-(1-Methyl-1H-imidazol-5-yl)ethyl 3-[(5-chlorothiophene-2-carbonyl)amino]-N-[2-ethyl-3-(2-oxopyrrolidin-1-yl)benzene-1-sulfonyl]-S-alaninate hydrochloride

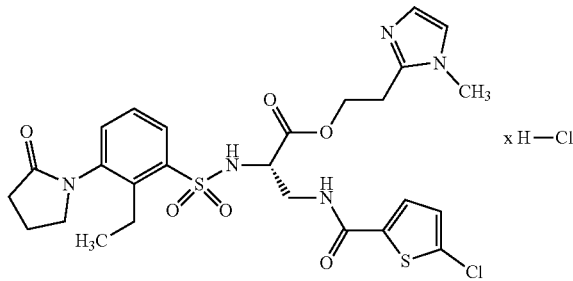

To a solution of 3-[(5-chlorothiophene-2-carbonyl)amino]-N-[2-ethyl-3-(2-oxopyrrolidin-1-yl)-benzene-1-sulfonyl]-S-alanine (60 mg, 120 µmol, Intermediate 15) in THF (2.3 ml) were added HBTU (82 mg, 216 µmol, CAS-RN 94790-37-1), DIPEA (63 µl, 360 µmol) and 2-(1-methyl-1H-imidazol-5-yl)ethanol (19 mg, 150 µmol, CAS-RN 802027-25-4), and the mixture was stirred overnight at rt. Then, the mixture was concentrated via rotary evaporator at a water bath temperature of 30° C. and the residue was taken up in acetonitrile/TFA/water and purified via preparative HPLC (Method 2). After lyophilization, a TFA-containing batch was obtained. For generation of the corresponding hydrochloride, the TFA-containing batch was dissolved in acetonitrile/water and the solution was passed ten times through a chloride ion exchanger (1.0 g amberlite IRA405 Cl resin, conditioned with deionized water) via force of gravity. The resin was then rinsed with deionized water/acetone and the solution was lyophilized to give the title compound (64 mg, 81% of theory, 98% purity).

LC-MS (Method 7): $R_t$=1.11 min; MS (ESIpos): m/z=608 [M+H]$^+$ $^1$H NMR (600 MHz, DMSO-$d_6$) δ [ppm]: 14.26 (br s, 1H), 8.99 (s, 1H), 8.84 (t, 1H), 8.70 (d, 1H), 7.81 (dd, 1H), 7.60 (d, 1H), 7.45 (dd, 1H), 7.42 (s, 1H), 7.34 (t, 1H), 7.18 (d, 1H), 4.15 (t, 2H), 4.08-4.03 (m, 1H), 3.74 (s, 3H), 3.69-3.57 (m, 2H), 3.57-3.50 (m, 1H), 3.47-3.40 (m, 1H), 2.93-2.78 (m, 4H), 2.43 (t, 2H), 2.17-2.10 (m, 2H), 1.08 (t, 3H).

Reference 10

2-(1-Methyl-1H-imidazol-2-yl)ethyl 3-{[(5-chloro-2-thienyl)carbonyl]amino}-N-{[2-ethyl-3-(2-oxopyrrolidin-1-yl)phenyl]sulfonyl}-S-alaninate hydrochloride

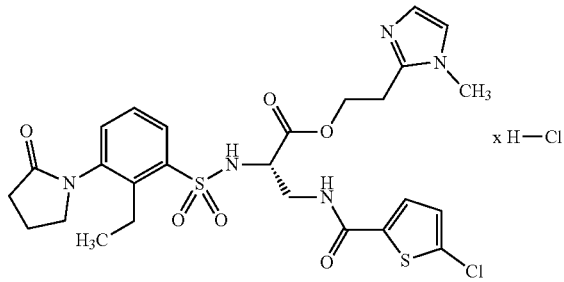

To a solution of 3-[(5-chlorothiophene-2-carbonyl)amino]-N-[2-ethyl-3-(2-oxopyrrolidin-1-yl)-benzene-1-sulfonyl]-S-alanine (350 mg, 0.70 mmol, Intermediate 15) in THF (13.6 ml) were added HBTU (478 mg, 1.26 mmol, CAS-RN 94790-37-1), DIPEA (0.37 ml, 2.10 mmol) and 2-(1-methyl-1H-imidazol-2-yl)ethanol (116 mg, 0.88 mmol, 95% purity, CAS-RN 18994-70-2), and the mixture was stirred for 4 h at rt. Then, the mixture was concentrated via rotary evaporator at a water bath temperature of 30° C. and the residue was taken up in acetonitrile/TFA/water and purified via preparative HPLC (Method 2). After lyophilization, a TFA-containing batch was obtained. For generation of the corresponding hydrochloride, the TFA-containing batch was dissolved in acetonitrile/water and the solution was passed ten times through a chloride ion exchanger (4.67 g amberlite IRA405 Cl resin, conditioned with deionized water) via force of gravity. The resin was then rinsed with deionized water/acetone and the solution was lyophilized to give the title compound (321 mg, 90% of theory, 99% purity).

LC-MS (Method 8): $R_t$=0.63 min; MS (ESIpos): m/z=608 [M+H]$^+$ $^1$H NMR (400 MHz, DMSO-$d_6$) δ [ppm]: 14.43 (br s, 1H), 9.00-8.93 (m, 1H), 8.70 (d, 1H), 7.80 (dd, 1H), 7.70-7.66 (m, 1H), 7.58 (d, 1H), 7.53 (d, 1H), 7.44 (d, 1H), 7.32 (t, 1H), 7.18 (d, 1H), 4.28-4.20 (m, 2H), 4.08-4.03 (m, 1H), 3.76 (s, 3H), 3.70-3.57 (m, 2H), 3.54-3.47 (m, 1H), 3.46-3.39 (m, 1H), 3.23 (t, 2H), 2.91-2.83 (m, 1H), 2.83-2.74 (m, 1H), 2.42 (t, 2H), 2.17-2.09 (m, 2H), 1.06 (t, 3H).

Reference 11

3-(1-Methyl-1H-imidazol-2-yl)propyl 3-[(5-chloro-thiophene-2-carbonyl)amino]-N-[2-ethyl-3-(2-oxopyrrolidin-1-yl)benzene-1-sulfonyl]-S-alaninate hydrochloride

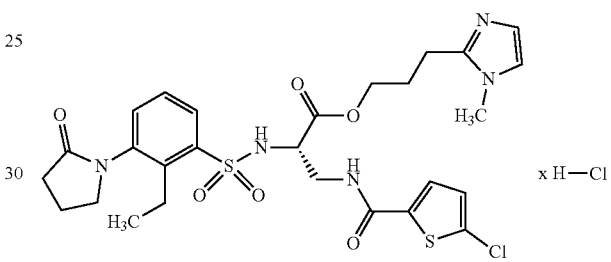

To a solution of 3-[(5-chlorothiophene-2-carbonyl)amino]-N-[2-ethyl-3-(2-oxopyrrolidin-1-yl)-benzene-1-sulfonyl]-S-alanine (50.0 mg, 100 µmol, Intermediate 15) in THF (1.9 ml) were added HBTU (68 mg, 180 µmol, CAS-RN 94790-37-1), DIPEA (52 µl, 300 µmol) and 3-(1-methyl-1H-imidazol-2-yl)propan-1-ol (18 mg, 95% purity, 125 µmol, CAS-RN 136609-58-0), and the mixture was stirred for 2 h at rt. Then, the mixture was concentrated via rotary evaporator at a water bath temperature of 30° C. and the residue was taken up in acetonitrile/TFA/water and purified via preparative HPLC (Method 2). After lyophilization, a TFA-containing batch was obtained. For generation of the corresponding hydrochloride, the TFA-containing batch was dissolved in acetonitrile/water and the solution was passed ten times through a chloride ion exchanger (400 mg amberlite IRA405 Cl resin, conditioned with deionized water) via force of gravity. The resin was then rinsed with deionized water/acetone and the solution was lyophilized to give the title compound (33 mg, 49% of theory, 97% purity).

LC-MS (Method 7): $R_t$=1.16 min; MS (ESIpos): m/z=622 [M+H]$^+$ $^1$H NMR (500 MHz, DMSO-$d_6$) δ [ppm]: 14.25 (br s, 1H), 8.92 (t, 1H), 8.74 (d, 1H), 7.84 (dd, 1H), 7.65 (d, 1H), 7.58 (d, 1H), 7.54 (d, 1H), 7.45 (dd, 1H), 7.35 (t, 1H), 7.16 (d, 1H), 4.10-4.02 (m, 1H), 3.98-3.92 (m, 2H), 3.72 (s, 3H), 3.69-3.51 (m, 3H), 3.50-3.40 (m, 1H), 2.95-2.79 (m, 4H), 2.42 (t, 2H), 2.17-2.09 (m, 2H), 1.92-1.83 (m, 2H), 1.08 (t, 3H).

Reference 12

2-(1-Methyl-1H-imidazol-2-yl)ethyl 3-[(5-chlorothiophene-2-carbonyl)amino]-N-{3-[(3S)-3-hydroxy-2-oxopyrrolidin-1-yl]-2-methylbenzene-1-sulfonyl}-S-alaninate hydrochloride

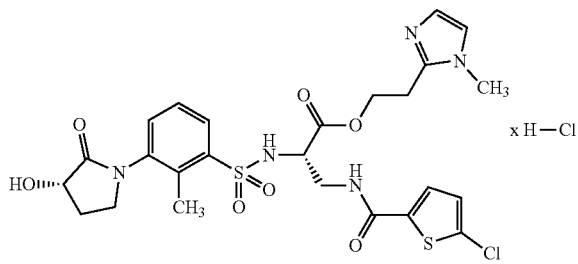

To a solution of 3-[(5-chlorothiophene-2-carbonyl)amino]-N-{3-[(3S)-3-hydroxy-2-oxopyrrolidin-1-yl]-2-methylbenzene-1-sulfonyl}-S-alanine (60 mg, 94% purity, 0.11 mmol, Intermediate 16) in THF (2.2 ml) were added HBTU (77 mg, 0.20 mmol, CAS-RN 94790-37-1), DIPEA (0.10 ml, 0.56 mmol) and 2-(1-methyl-1H-imidazol-2-yl)ethanol (18 mg, 0.14 mmol, CAS-RN 18994-70-2), and the mixture was stirred overnight at rt. Then, the mixture was concentrated via rotary evaporator at a water bath temperature of 30° C. and the residue was taken up in acetonitrile/TFA/water and purified via preparative HPLC (Method 2). After lyophilization, a TFA-containing batch was obtained. For generation of the corresponding hydrochloride, the TFA-containing batch was dissolved in acetonitrile/water and the solution was passed ten times through a chloride ion exchanger (400 mg amberlite IRA405 Cl resin, conditioned with deionized water) via force of gravity. The resin was then rinsed with deionized water and the solution was lyophilized to give the title compound (33 mg, 45% of theory, 98% purity).

LC-MS (Method 7): $R_t$=0.96 min; MS (ESIpos): m/z=610 [M−HCl+H]$^+$ $^1$H NMR (600 MHz, DMSO-$d_6$) δ [ppm]: 14.27 (br s, 1H), 8.82 (t, 1H), 8.64 (d, 1H), 7.76 (d, 1H), 7.59 (d, 2H), 7.57 (d, 1H), 7.52 (d, 1H), 7.42 (d, 1H), 7.32 (t, 1H), 7.17 (d, 1H), 5.73 (br s, 1H), 4.32 (t, 1H), 4.29-4.17 (m, 2H), 4.06-4.01 (m, 1H), 3.76 (s, 3H), 3.57-3.44 (m, 3H), 3.41-3.35 (m, 1H), 3.20 (t, 2H), 2.47-2.38 (m, 1H), 2.34 (s, 3H), 2.02-1.91 (m, 1H).

Reference 13

2-(1-Methyl-1H-imidazol-2-yl)ethyl 3-[(5-chlorothiophene-2-carbonyl)amino]-N-{3-[(3R)-3-hydroxy-2-oxopyrrolidin-1-yl]-2-methylbenzene-1-sulfonyl}-S-alaninate hydrochloride

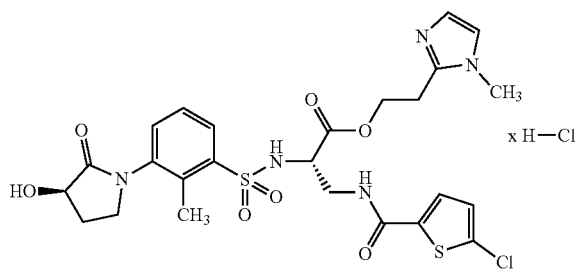

To a solution of 3-[(5-chlorothiophene-2-carbonyl)amino]-N-{3-[(3R)-3-hydroxy-2-oxopyrrolidin-1-yl]-2-methylbenzene-1-sulfonyl}-S-alanine (60 mg, 89% purity, 0.11 mmol, Intermediate 17) in THF (2.1 ml) were added HBTU (73 mg, 0.19 mmol, CAS-RN 94790-37-1), DIPEA (0.09 ml, 0.53 mmol) and 2-(1-methyl-1H-imidazol-2-yl)ethanol (17 mg, 0.13 mmol, CAS-RN 18994-70-2), and the mixture was stirred overnight at rt. Then, the mixture was concentrated via rotary evaporator at a water bath temperature of 30° C. and the residue was taken up in acetonitrile/TFA/water and purified via preparative HPLC (Method 2). After lyophilization, a TFA-containing batch was obtained. For generation of the corresponding hydrochloride, the TFA-containing batch was dissolved in acetonitrile/water and the solution was passed ten times through a chloride ion exchanger (600 mg amberlite IRA405 Cl resin, conditioned with deionized water) via force of gravity. The resin was then rinsed with deionized water and the solution was lyophilized to give the title compound (45 mg, 62% of theory, 95% purity).

LC-MS (Method 7): $R_t$=0.96 min; MS (ESIpos): m/z=610 [M−HCl+H]$^+$ $^1$H NMR (600 MHz, DMSO-$d_6$) δ [ppm]: 14.35 (br s, 1H), 8.87 (t, 1H), 8.66 (d, 1H), 7.77 (d, 1H), 7.62 (d, 1H), 7.58 (d, 1H), 7.53 (d, 1H), 7.44 (d, 1H), 7.33 (t, 1H), 7.17 (d, 1H), 5.71 (br s, 1H), 4.32 (t, 1H), 4.26-4.17 (m, 2H), 4.09-4.03 (m, 1H), 3.76 (s, 3H), 3.58-3.46 (m, 3H), 3.43-3.38 (m, 1H), 3.21 (t, 2H), 2.48-2.40 (m, 1H), 2.33 (s, 3H), 2.02-1.93 (m, 1H).

Reference 14

2-(1-Methyl-1H-imidazol-2-yl)ethyl 3-[(5-chlorothiophene-2-carbonyl)amino]-N-{2-ethyl-3-[(3R)-3-hydroxy-2-oxopyrrolidin-1-yl]benzene-1-sulfonyl}-S-alaninate hydrochloride

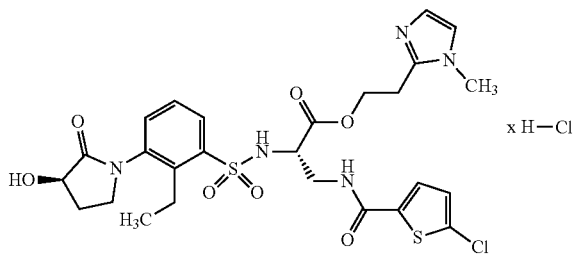

To a solution of 3-[(5-chlorothiophene-2-carbonyl)amino]-N-{2-ethyl-3-[(3R)-3-hydroxy-2-oxopyrrolidin-1-yl]benzene-1-sulfonyl}-S-alanine (120 mg, 0.23 mmol, Intermediate 20) in THF (4.5 ml) were added HBTU (159 mg, 0.42 mmol, CAS-RN 94790-37-1), DIPEA (0.12 ml, 0.70 mmol) and 2-(1-methyl-1H-imidazol-2-yl)ethanol (37 mg, 0.29 mmol, CAS-RN 18994-70-2), and the mixture was stirred overnight at rt. Then, the mixture was concentrated via rotary evaporator at a water bath temperature of 30° C. and the residue was taken up in acetonitrile/TFA/water and purified via preparative HPLC (Method 2). After lyophilization, a TFA-containing product was obtained. For generation of the hydrochloride, the TFA-containing product was dissolved in acetonitrile/water and the solution was eluted ten times through a chloride ion exchanger (1.5 g amberlite IRA405 Cl resin, conditioned with deionized water). The resin was then rinsed with deionized water and the solution was lyophilized to give the title compound (95 mg, 61% of theory, 99% purity).

LC-MS (Method 7): $R_t$=1.02 min; MS (ESIpos): m/z=624 [M+H]$^+$ $^1$H NMR (600 MHz, DMSO-d$_6$) δ [ppm]: 14.20 (s, 1H), 8.81 (br s, 1H), 8.66 (d, 1H), 7.81 (d, 1H), 7.60 (d, 1H), 7.58 (d, 1H), 7.54 (d, 1H), 7.43 (d, 1H), 7.34 (t, 1H), 7.18 (d, 1H), 4.30 (t, 1H), 4.27-4.21 (m, 2H), 4.06 (dd, 1H), 3.76 (s, 3H), 3.63-3.56 (m, 1H), 3.55-3.47 (m, 2H), 3.46-3.39 (m, 1H), 3.22 (t, 2H), 2.92-2.84 (m, 1H), 2.83-2.75 (m, 1H), 2.48-2.40 (m, 1H), 2.00-1.91 (m, 1H), 1.06 (m, 3H)

Reference 15

3-(1-Methyl-1H-imidazol-2-yl)propyl 3-[(5-chloro-thiophene-2-carbonyl)amino]-N-{2-ethyl-3-[(3S)-3-hydroxy-2-oxopyrrolidin-1-yl]benzene-1-sulfonyl}-S-alaninate hydrochloride

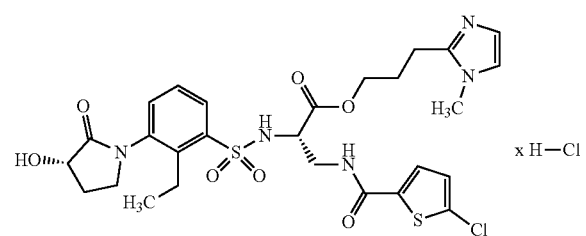

To a solution of 3-[(5-chlorothiophene-2-carbonyl)amino]-N-{2-ethyl-3-[(3S)-3-hydroxy-2-oxopyrrolidin-1-yl]benzene-1-sulfonyl}-S-alanine (60 mg, 0.12 mmol, Intermediate 19) in THF (2.3 ml) were added HBTU (79 mg, 0.21 mmol, CAS-RN 94790-37-1), DIPEA (0.08 ml, 0.47 mmol) and 3-(1-methyl-1H-imidazol-2-yl)propan-1-ol (24.5 mg, 0.17 mmol, CAS-RN 136609-58-0), and the mixture was stirred for 2 h at rt. The mixture was then taken up in acetonitrile/TFA/water and purified via preparative HPLC (Method 2). After lyophilization, a TFA-containing batch was obtained. For generation of the corresponding hydrochloride, the TFA-containing batch was dissolved in acetonitrile/water and the solution was passed ten times through a chloride ion exchanger (880 mg amberlite IRA405 Cl resin, conditioned with deionized water) via force of gravity. The resin was then rinsed with deionized water and the solution was lyophilized to give the title compound (19 mg, 22% of theory, 90% purity).

LC-MS (Method 9): $R_t$=0.83 min; MS (ESIpos): m/z=638 [M−HCl+H]$^+$ $^1$H NMR (400 MHz, DMSO-d$_6$) δ [ppm]: 14.06 (br s, 1H), 8.80 (t, 1H), 8.72 (d, 1H), 7.85 (dd, 1H), 7.60-7.57 (m, 2H), 7.54 (d, 1H), 7.43 (dd, 1H), 7.37 (t, 1H), 7.16 (d, 1H), 5.75 (br s, 1H), 4.31 (t, 1H), 4.12-4.02 (m, 1H), 3.97 (t, 2H), 3.72 (s, 3H), 3.65-3.53 (m, 2H), 3.51-3.42 (m, 2H), 2.96-2.84 (m, 4H), 2.47-2.40 (m, 1H), 1.99-1.80 (m, 3H), 1.07 (t, 3H).

Reference 16

3-(1-Methyl-1H-imidazol-2-yl)propyl 3-[(5-chloro-thiophene-2-carbonyl)amino]-N-{2-ethyl-3-[(3R)-3-hydroxy-2-oxopyrrolidin-1-yl]benzene-1-sulfonyl}-S-alaninate hydrochloride

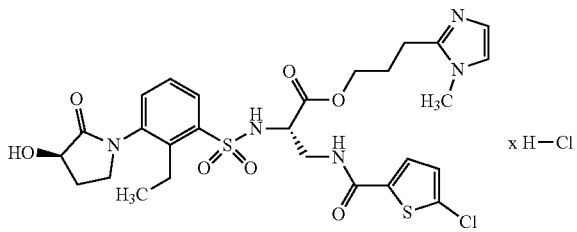

To a solution of 3-[(5-chlorothiophene-2-carbonyl)amino]-N-{2-ethyl-3-[(3R)-3-hydroxy-2-oxopyrrolidin-1-yl]benzene-1-sulfonyl}-S-alanine (60 mg, 0.12 mmol, Intermediate 20) in THF (2.3 ml) were added HBTU (79 mg, 0.21 mmol, CAS-RN 94790-37-1), DIPEA (0.08 ml, 0.47 mmol) and 3-(1-methyl-1H-imidazol-2-yl)propan-1-ol (24.5 mg, 0.17 mmol, CAS-RN 136609-58-0), and the mixture was stirred for 2 h at rt. The mixture was then taken up in acetonitrile/TFA/water and purified via preparative HPLC (Method 2). After lyophilization, a TFA-containing batch was obtained. For generation of the corresponding hydrochloride, the TFA-containing batch was dissolved in acetonitrile/water and the solution was passed ten times through a chloride ion exchanger (500 mg amberlite IRA405 Cl resin, conditioned with deionized water) via force of gravity. The resin was then rinsed with deionized water and the solution was lyophilized to give the title compound (43 mg, 49% of theory, 90% purity).

LC-MS (Method 9): $R_t$=0.83 min; MS (ESIpos): m/z=638 [M−HCl+H]$^+$ $^1$H NMR (400 MHz, DMSO-d$_6$) δ [ppm]: 14.10 (br s, 1H), 8.84 (br s, 1H), 8.72 (d, 1H), 7.86 (dd, 1H), 7.62-7.57 (m, 2H), 7.55 (d, 1H), 7.44 (d, 1H), 7.37 (t, 1H), 7.16 (d, 1H), 5.75 (br s, 1H), 4.31 (t, 1H), 4.11-4.02 (m, 1H), 4.00-3.91 (m, 2H), 3.72 (s, 3H), 3.63-3.40 (m, 4H), 2.96-2.77 (m, 4H), 2.47-2.40 (m, 1H), 1.99-1.82 (m, 3H), 1.07 (t, 3H).

WORKING EXAMPLES

Example 1

2-(1-Methyl-1H-imidazol-2-yl)ethyl 3-[(5-chlorothiophene-2-carbonyl)amino]-N-{2-ethyl-3-[(3S)-3-hydroxy-2-oxopyrrolidin-1-yl]benzene-1-sulfonyl}-S-alaninate

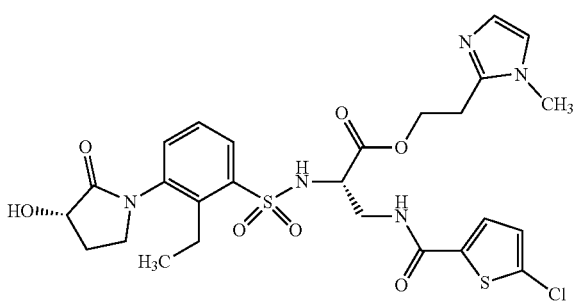 [SMILES: CCc1c(N2CC[C@H](O)C2=O)cccc1S(=O)(=O)N[C@@H](CNC(=O)c1ccc(Cl)s1)C(=O)OCCc1nccn1C]

To a solution of 3-[(5-chlorothiophene-2-carbonyl)amino]-N-{2-ethyl-3-[(3S)-3-hydroxy-2-oxopyrrolidin-1-yl]benzene-1-sulfonyl}-S-alanine (2.0 g, 3.88 mmol, Intermediate 19) in DCM (20 ml) and DMF (4 ml) was added 2-(1-methyl-1H-imidazol-2-yl)ethanol (978 mg, 7.75 mmol, CAS-RN 18994-70-2), and the solution was cooled to 0° C. Then, Oxyma (661 mg, 4.65 mmol, CAS-RN 3849-21-6) was added portionwise, followed by EDCI (892 mg, 4.65 mmol, CAS-RN 25952-53-8), and the mixture was stirred for 1.5 h at 0° C. The mixture was washed with ice-cold water (20 ml) and after phase separation, the organic phase was washed three times with ice-cold water. While washing for the third time, DCM (10 ml) and 10% aqueous sodium chloride solution (10 ml) were added for improving phase separation. The organic phase was then dried over sodium sulfate and concentrated. After drying in vacuo, the residue was purified via flash chromatography using a basic silicagel phase (Isolera, KP-NH 28 g, DCM/acetone gradient 9:1→1:9). The combined product fractions were concentrated and the residue was dried in vacuo to give the title compound (1.51 g, 62% of theory, 100% purity).

LC-MS (Method 7): $R_t$=1.02 min; MS (ESIpos): m/z=624 [M+H]$^+$ $^1$H NMR (600 MHz, DMSO-d$_6$) δ [ppm]: 9.09 (t, 1H), 8.65 (d, 1H), 7.82 (dd, 1H), 7.57 (d, 1H), 7.44 (dd, 1H), 7.38 (t, 1H), 7.17 (d, 1H), 7.03 (d, 1H), 6.74 (d, 1H), 5.75 (d, 1H), 4.34-4.01 (m, 4H), 3.66-3.56 (m, 1H), 3.51 (s, 3H), 3.50-3.39 (m, 3H), 2.94-2.70 (m, 4H), 2.48-2.38 (m, 1H), 2.01-1.87 (m, 1H), 1.06 (t, 3H).

IR: See FIG. 1

Example 2

2-(1-Methyl-1H-imidazol-2-yl)ethyl 3-[(5-chlorothiophene-2-carbonyl)amino]-N-{2-ethyl-3-[(3S)-3-hydroxy-2-oxopyrrolidin-1-yl]benzene-1-sulfonyl}-S-alaninate hydrochloride

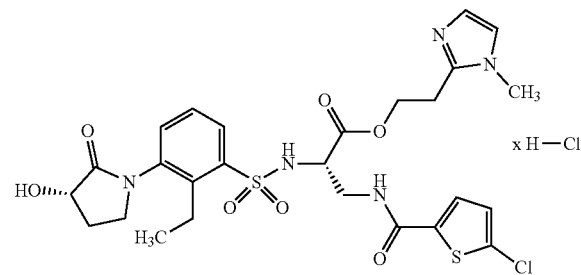

Alternative Synthesis A

To a solution of 3-[(5-chlorothiophene-2-carbonyl)amino]-N-{2-ethyl-3-[(3S)-3-hydroxy-2-oxopyrrolidin-1-yl]benzene-1-sulfonyl}-S-alanine (190 mg, 0.37 mmol, Intermediate 19) in THF (7.2 ml) were added HBTU (251 mg, 0.66 mmol, CAS-RN 94790-37-1), DIPEA (0.19 ml, 1.11 mmol) and 2-(1-methyl-1H-imidazol-2-yl)ethanol (93 mg, 0.74 mmol, CAS-RN 18994-70-2), and the mixture was stirred for 2 h at rt. Then, the mixture was concentrated via rotary evaporator at a water bath temperature of 30° C. and the residue was taken up in acetonitrile/TFA/water and purified via preparative HPLC (Method 2). After lyophilization, a TFA-containing batch was obtained. For generation of the corresponding hydrochloride, the TFA-containing batch was dissolved in acetonitrile/water and the solution was passed ten times through a chloride ion exchanger (2.66 g amberlite IRA405 Cl resin, conditioned with deionized water) via force of gravity. The resin was then rinsed with deionized water and the solution was lyophilized to give the title compound (122 mg, 49% of theory, 98% purity).

LC-MS (Method 7): $R_t$=1.01 min; MS (ESIpos): m/z=624 [M+H]$^+$ $^1$H NMR (600 MHz, DMSO-d$_6$) δ [ppm]: 14.30 (br s, 1H), 8.88 (t, 1H), 8.69 (d, 1H), 7.81 (d, 1H), 7.63 (d, 1H), 7.57 (d, 1H), 7.53 (d, 1H), 7.43 (d, 1H), 7.33 (t, 1H), 7.18 (d, 1H), 5.74 (br s, 1H), 4.30 (t, 1H), 4.29-4.19 (m, 2H), 4.05 (dd, 1H), 3.77 (s, 3H), 3.63-3.56 (m, 1H), 3.54-3.39 (m, 3H), 3.22 (t, 2H), 2.90-2.76 (m, 2H), 2.48-2.40 (m, 1H), 2.00-1.87 (m, 1H), 1.05 (t, 3H).

IC: 4.6 wt % chloride, <1 wt % TFA

Alternative Synthesis B

To a solution of 2-(1-methyl-1H-imidazol-2-yl)ethyl 3-[(5-chlorothiophene-2-carbonyl)amino]-N-{2-ethyl-3-[(3S)-3-hydroxy-2-oxopyrrolidin-1-yl]benzene-1-sulfonyl}-S-alaninate (2.31 g, 3.70 mmol, Example 1) in DCM (3.5 ml) was added dropwise—while vigorously stirring and cooling with an ice bath—a solution of 1M hydrogen chloride in diethyl ether (4.07 ml, 4.07 mmol), followed by more diethyl ether (70 ml) for improving stirability. After stirring for 10 min under cooling and 15 min at rt, the precipitate was filtered off and washed with diethyl ether (100 ml). Then, the precipitate was dissolved again in ice-cold water (20 ml) by aid of brief ultrasound treatment and the solution was lyophilized. To remove traces of diethyl ether, the lyophilization was repeated to give the title compound (2.06 g, 84% of theory, 99% purity).

LC-MS (Method 7): $R_t$=0.99 min; MS (ESIpos): m/z=624 [M+H]$^+$

Chiral HPLC (Method 11): $R_t$=9.10 min $^1$H NMR (500 MHz, DMSO-d$_6$) δ [ppm]: 14.42 (br s, 1H), 8.98 (t, 1H), 8.75 (d, 1H), 7.80 (dd, 1H), 7.68 (d, 1H), 7.58 (d, 1H), 7.54 (d, 1H), 7.43 (d, 1H), 7.33 (t, 1H), 7.19 (d, 1H), 5.80 (br s, 1H), 4.31 (t, 1H), 4.29-4.19 (m, 2H), 4.08-4.01 (m, 1H), 3.77 (s, 3H), 3.63-3.56 (m, 1H), 3.54-3.39 (m, 3H), 3.23 (t, 2H), 2.90-2.73 (m, 2H), 2.48-2.40 (m, 1H), 2.00-1.87 (m, 1H), 1.05 (t, 3H).

IC: 4.7 wt % chloride

Alternative Synthesis C

To ethyl acetate (2.0 ml) at 60° C. was added 2-(1-methyl-1H-imidazol-2-yl)ethyl 3-[(5-chlorothiophene-2-carbonyl)amino]-N-{2-ethyl-3-[(3S)-3-hydroxy-2-oxopyrrolidin-1-yl]benzene-1-sulfonyl}-S-alaninate (30 mg, 48.1 mmol, Example 1) while stirring. The solution was cooled to rt, 1 M hydrochloric acid (50.2 mg, 49.22 mmol) was added and the mixture was stirred for 2 d at rt in a capped glass vial. Then, the cap was replaced with a Parafilm tape, 2-5 holes were punched into the tape with a needle and the mixture was gently stirred for another 10 d at rt, allowing the solvent to slowly evaporate. The title compound was obtained as a solid.

LC-MS (Method 7): $R_t$=1.03 min; MS (ESIpos): m/z=624 [M+H]$^+$ $^1$H NMR (500 MHz, DMSO-d$_6$) δ [ppm]: 14.40 (br s, 1H), 8.97 (t, 1H), 8.74 (d, 1H), 7.80 (d, 1H), 7.67 (d, 1H), 7.58 (d, 1H), 7.54 (d, 1H), 7.43 (d, 1H), 7.33 (t, 1H), 7.19 (d, 1H), 5.75 (br s, 1H), 4.31 (t, 1H), 4.28-4.19 (m, 2H), 4.08-4.00 (m, 1H), 3.77 (s, 3H), 3.63-3.56 (m, 1H), 3.54-3.39 (m, 3H), 3.23 (t, 2H), 2.90-2.74 (m, 2H), 2.48-2.41 (m, 1H), 1.98-1.92 (m, 1H), 1.05 (t, 3H).

Figure 2:
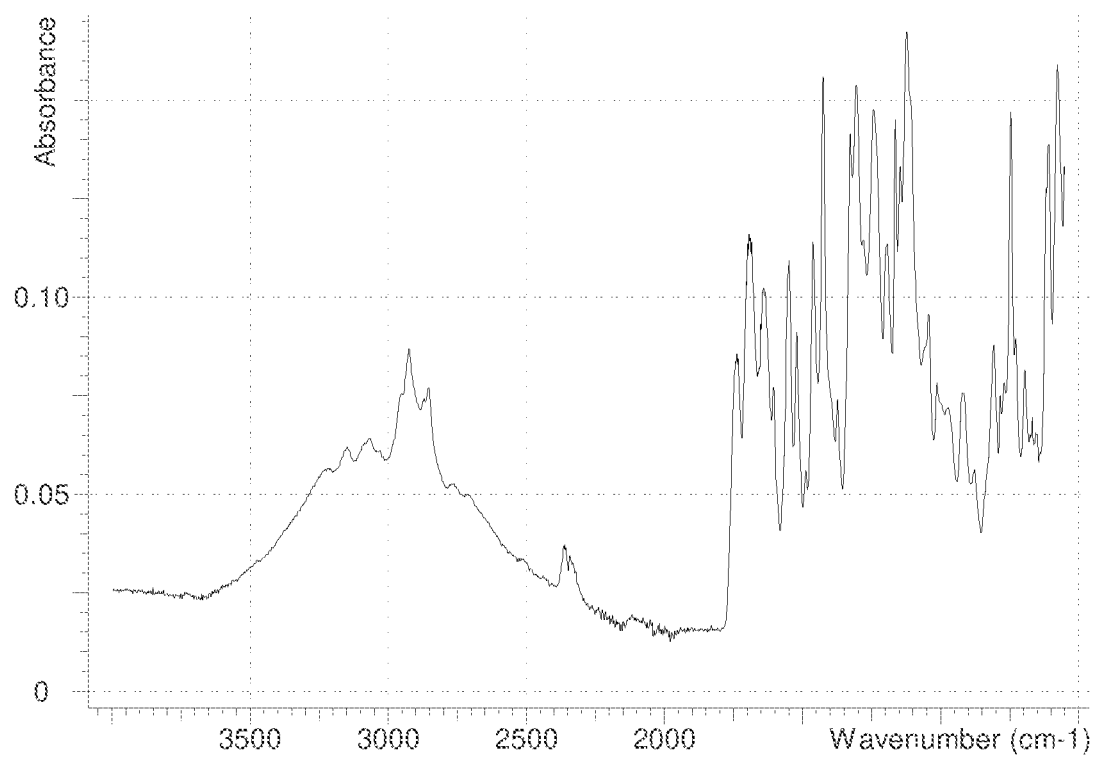
FIG. 2: Infrared spectrum of Example 2

XRPD: amorphous; IR: See FIG. 2

Example 3

2-(1-Methyl-1H-imidazol-2-yl)ethyl 3-{[(5-chloro-2-thienyl)carbonyl]amino}-N-({2-ethyl-3-[(3S)-3-hydroxy-2-oxopyrrolidin-1-yl]phenyl}sulfonyl)-S-alaninate sulfate

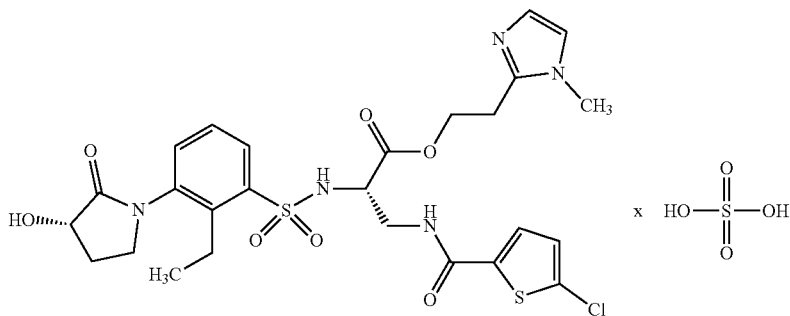

To ethyl acetate (2.0 ml) at 60° C. was added 2-(1-methyl-1H-imidazol-2-yl)ethyl 3-[(5-chlorothiophene-2-carbonyl)amino]-N-{2-ethyl-3-[(3S)-3-hydroxy-2-oxopyrrolidin-1-yl]benzene-1-sulfonyl}-S-alaninate (30 mg, 48.1 mmol, Example 1) while stirring. The solution was cooled to rt, 0.5 M sulfuric acid (100.6 mg, 47.90 mmol) was added and the mixture was stirred for 2 d at rt in a capped glass vial. Then, the cap was replaced with a Parafilm tape, 2-5 holes were punched into the tape with a needle and the mixture was gently stirred for another 10 d at rt, allowing the solvent to slowly evaporate. The title compound was obtained as a solid.

LC-MS (Method 7): $R_t$=1.03 min; MS (ESIpos): m/z=624 [M+H]$^+$ $^1$H NMR (500 MHz, DMSO-d$_6$) δ [ppm]: 13.94 (br s, 1H), 8.70 (t, 1H), 8.64 (d, 1H), 7.80 (d, 1H), 7.62-7.56 (m, 1H), 7.55 (d, 1H), 7.52 (d, 1H), 7.43 (d, 1H), 7.34 (t, 1H), 7.21-7.17 (m, 1H), 4.36-4.27 (m, 1H), 4.27-4.17 (m, 2H), 4.11-3.97 (m, 1H), 3.76 (s, 3H), 3.64-3.55 (m, 1H), 3.55-3.34 (m, 3H), 3.21 (t, 2H), 2.91-2.75 (m, 2H), 2.49-2.41 (m, 1H), 2.01-1.92 (m, 1H), 1.06 (t, 3H).

Figure 3:
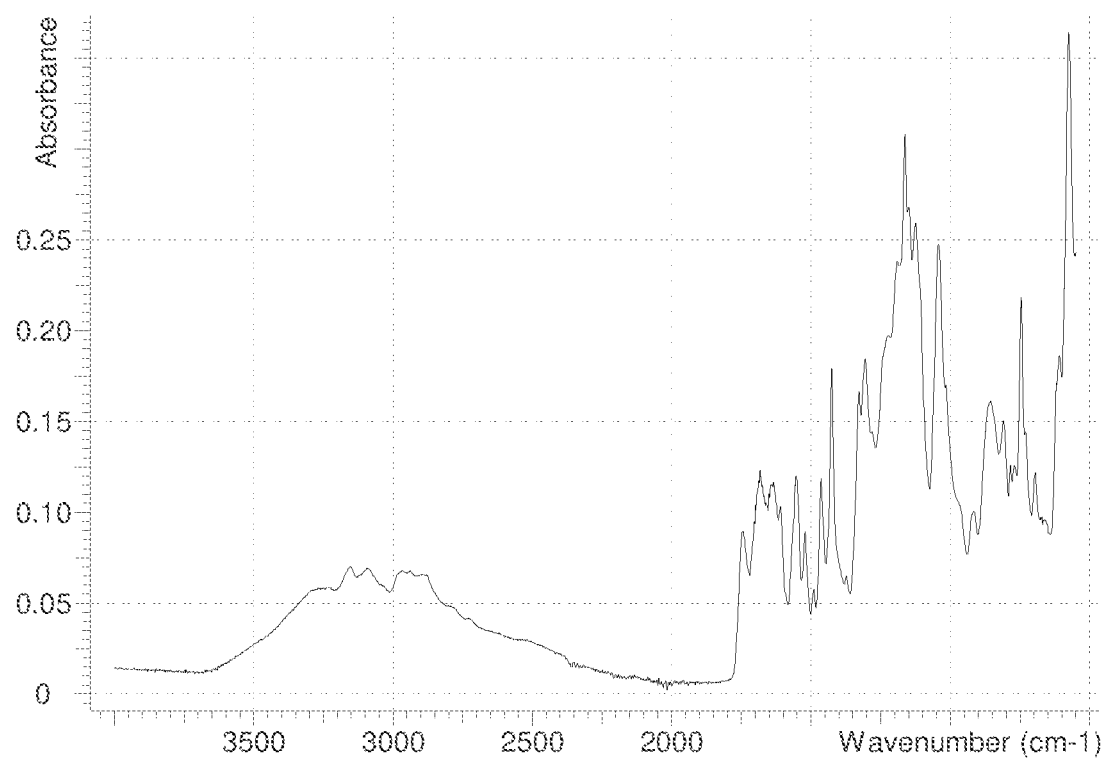
FIG. 3: Infrared spectrum of Example 3

XRPD: amorphous; IR: See FIG. 3

Example 4

2-(1-Methyl-1H-imidazol-2-yl)ethyl 3-{[(5-chloro-2-thienyl)carbonyl]amino}-N-({2-ethyl-3-[(3S)-3-hydroxy-2-oxopyrrolidin-1-yl]phenyl}sulfonyl)-S-alaninate methanesulfonate To ethyl acetate (2.0 ml) at 60° C. was added 2-(1-methyl-1H-imidazol-2-yl)ethyl 3-[(5-chlorothiophene-2-carbonyl)amino]-N-{2-ethyl-3-[(3S)-3-hydroxy-2-oxopyrrolidin-1-yl]benzene-1-sulfonyl}-S-alaninate (30 mg, 48.1 mmol, Example 1) while stirring. The solution was cooled to rt, methanesulfonic acid (4.9 mg, 51.0 mmol) was added and the mixture was stirred for 2 d at rt in a capped glass vial. Then, the cap was replaced with a Parafilm tape, 2-5 holes were punched into the tape with a needle and the mixture was gently stirred for another 10 d at rt, allowing the solvent to slowly evaporate. The title compound was obtained as a solid.

LC-MS (Method 7): $R_t$=1.02 min; MS (ESIpos): m/z=624 [M+H]$^+$ $^1$H NMR (500 MHz, DMSO-d$_6$) δ [ppm]: 13.97 (br s, 1H), 8.72 (t, 1H), 8.65 (d, 1H), 7.80 (d, 1H), 7.59 (s, 1H), 7.55 (d, 1H), 7.53 (d, 1H), 7.43 (d, 1H), 7.34 (t, 1H), 7.19 (d, 1H), 5.75 (br s, 1H), 4.31 (t, 1H), 4.27-4.18 (m, 2H), 4.09-3.98 (m, 1H), 3.76 (s, 3H), 3.63-3.57 (m, 1H), 3.55-3.36 (m, 3H), 3.21 (br t, 2H), 2.91-2.74 (m, 2H), 2.48-2.41 (m, 1H), 2.34 (s, 3H), 1.98-1.88 (m, 1H), 1.06 (t, 3H).

Figure 4:
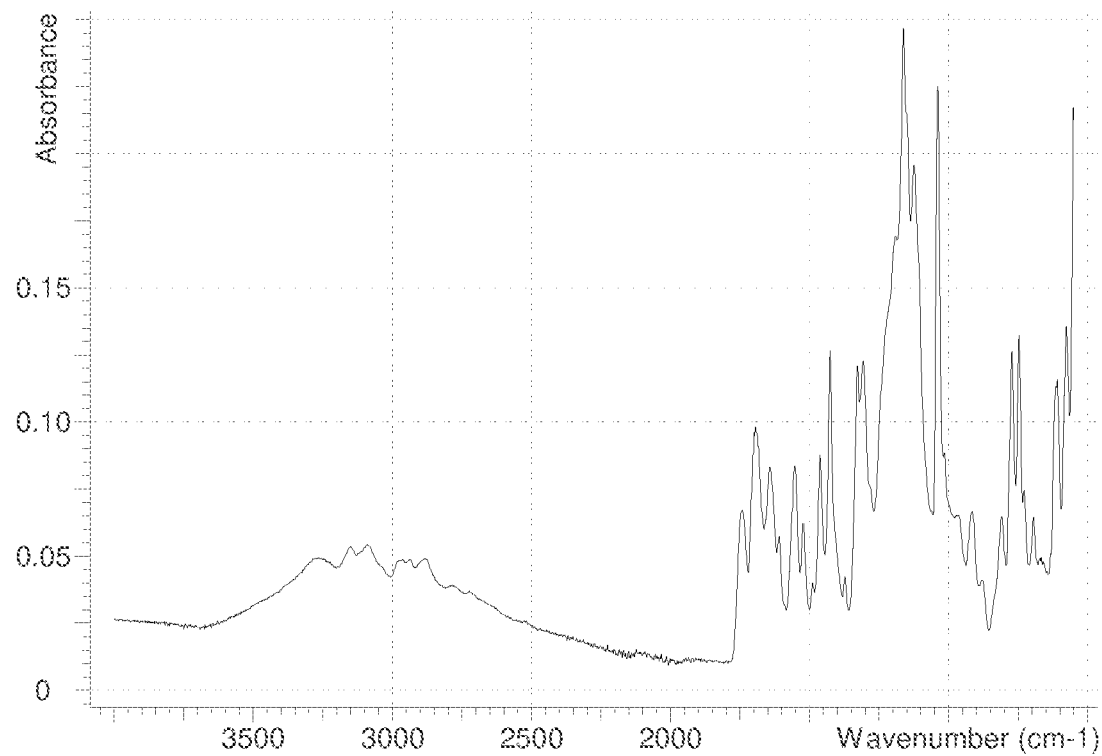
FIG. 4: Infrared spectrum of Example 4

XRPD: amorphous; IR: See FIG. 4

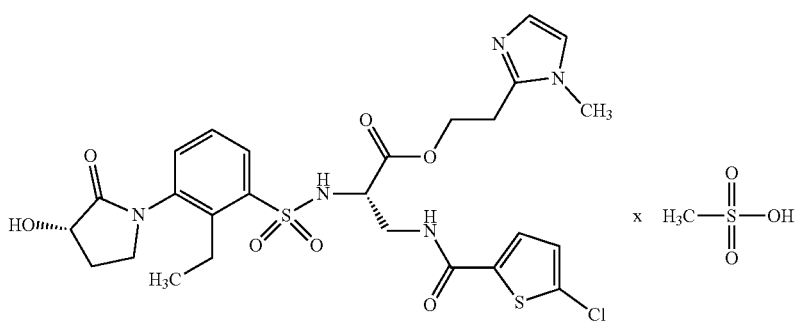

Example 5

2-(1-Methyl-1H-imidazol-2-yl)ethyl 3-{[(5-chloro-2-thienyl)carbonyl]amino}-N-({2-ethyl-3-[(3S)-3-hydroxy-2-oxopyrrolidin-1-yl]phenyl}sulfonyl)-S-alaninate 4-methylbenzenesulfonate

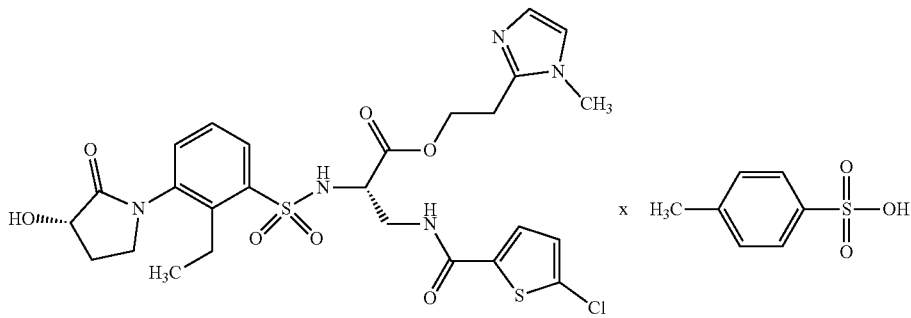

To ethyl acetate (2.0 ml) at 60° C. was added 2-(1-methyl-1H-imidazol-2-yl)ethyl 3-[(5-chlorothiophene-2-carbonyl)amino]-N-{2-ethyl-3-[(3S)-3-hydroxy-2-oxopyrrolidin-1-yl]benzene-1-sulfonyl}-S-alaninate (30 mg, 48.1 mmol, Example 1) while stirring. The solution was cooled to rt, 4-toluenesulfonic acid (9.6 mg, 55.7 mmol) was added and the mixture was stirred for 2 d at rt in a capped glass vial. Then, the cap was replaced with a Parafilm tape, 2-5 holes were punched into the tape with a needle and the mixture was gently stirred for another 10 d at rt, allowing the solvent to slowly evaporate. The title compound was obtained as a solid.

LC-MS (Method 7): $R_t$=1.02 min; MS (ESIpos): m/z=624 [M+H]$^+$ and $R_t$=0.57 min, MS (ESIneg): m/z=171 [M−H]$^-$ $^1$H NMR (500 MHz, DMSO-d$_6$) δ [ppm]: 13.92 (br s, 1H), 8.69 (br t, 1H), 8.64 (d, 1H), 7.80 (d, 1H), 7.60-7.56 (m, 1H), 7.55 (d, 1H), 7.52 (d, 1H), 7.48 (d, 2H), 7.43 (d, 1H), 7.36-7.31 (m, 1H), 7.21-7.16 (m, 1H), 7.11 (d, 2H), 4.35-4.28 (m, 1H), 4.27-4.17 (m, 2H), 4.07-4.00 (m, 1H), 3.76 (s, 3H), 3.63-3.56 (m, 1H), 3.54-3.36 (m, 3H), 3.20 (br t, 2H), 2.91-2.75 (m, 2H), 2.48-2.41 (m, 1H), 2.29 (s, 3H), 2.02-1.92 (m, 1H), 1.09-1.03 (m, 3H).

Figure 5:
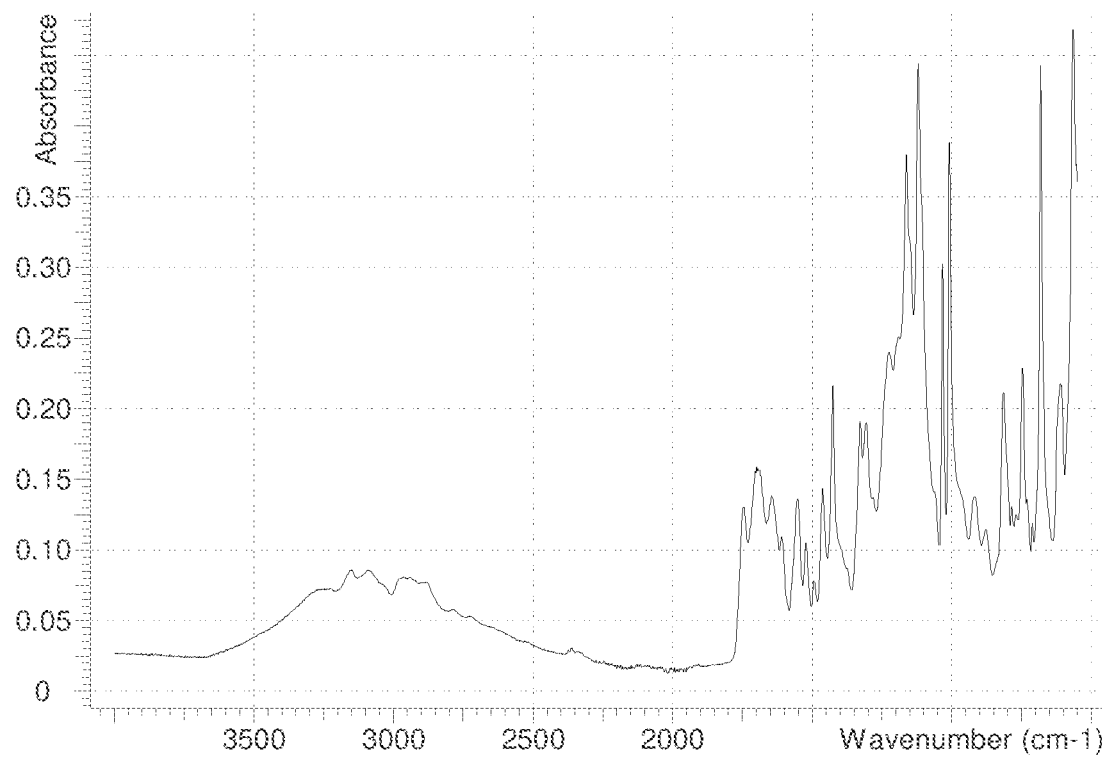
FIG. 5: Infrared spectrum of Example 5

XRPD: amorphous; IR: See FIG. 5

Example 6

2-(1-Methyl-1H-imidazol-2-yl)ethyl 3-{[(5-chloro-2-thienyl)carbonyl]amino}-N-({2-ethyl-3-[(3S)-3-hydroxy-2-oxopyrrolidin-1-yl]phenyl}sulfonyl)-S-alaninate maleate

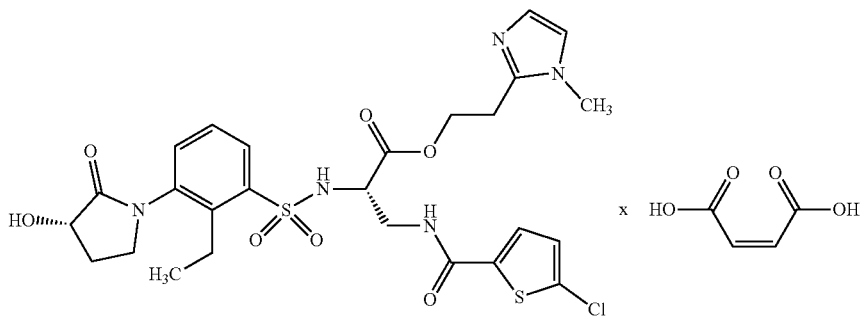

To ethyl acetate (2.0 ml) at 60° C. was added 2-(1-methyl-1H-imidazol-2-yl)ethyl 3-[(5-chlorothiophene-2-carbonyl)amino]-N-{2-ethyl-3-[(3S)-3-hydroxy-2-oxopyrrolidin-1-yl]benzene-1-sulfonyl}-S-alaninate (30 mg, 48.1 mmol, Example 1) while stirring. The solution was cooled to rt, maleic acid (5.8 mg, 50.0 mmol) was added and the mixture was stirred for 2 d at rt in a capped glass vial. Then, the cap was replaced with a Parafilm tape, 2-5 holes were punched into the tape with a needle and the mixture was gently stirred for another 10 d at rt, allowing the solvent to slowly evaporate. The title compound was obtained as a solid.

LC-MS (Method 7): $R_t$=1.03 min; MS (ESIpos): m/z=624 [M+H]$^+$ $^1$H NMR (500 MHz, DMSO-d$_6$) δ [ppm]: 8.75 (br t, 1H), 8.65 (br d, 1H), 7.80 (d, 1H), 7.52 (d, 1H), 7.50 (d, 1H), 7.45-7.40 (m, 2H), 7.38-7.32 (m, 1H), 7.19 (d, 1H), 6.07 (s, 2H), 5.76 (br s, 1H), 4.31 (t, 1H), 4.23 (br t, 2H), 4.09-3.99 (m, 1H), 3.72 (s, 3H), 3.65-3.56 (m, 1H), 3.52-3.37 (m, 3H), 3.13 (br t, 2H), 2.91-2.75 (m, 2H), 2.48-2.41 (m, 1H), 1.97-1.90 (m, 1H), 1.06 (t, 3H).

Figure 6:
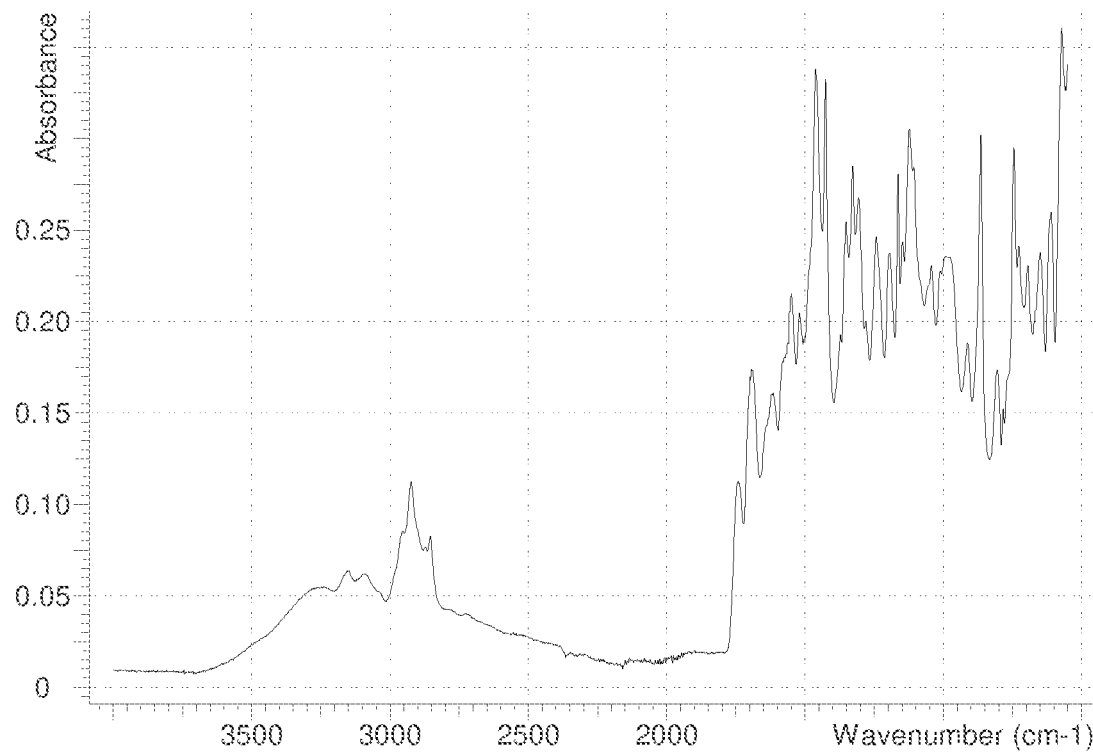
FIG. 6: Infrared spectrum of Example 6

XRPD: amorphous; IR: See FIG. 6

Example 7

2-(1-Methyl-1H-imidazol-2-yl)ethyl 3-{[(5-chloro-2-thienyl)carbonyl]amino}-N-({2-ethyl-3-[(3S)-3-hydroxy-2-oxopyrrolidin-1-yl]phenyl}sulfonyl)-S-alaninate phosphate

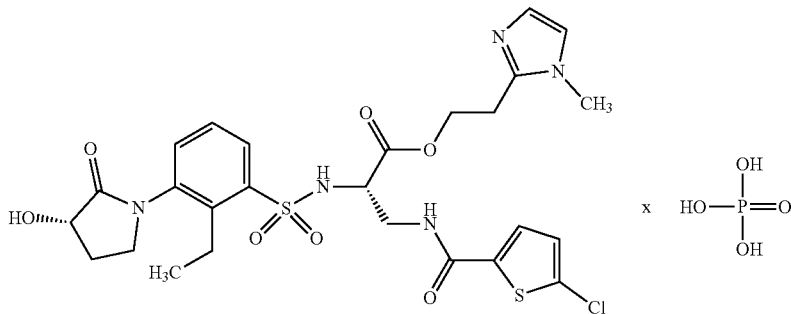

To ethyl acetate (2.0 ml) at 60° C. was added 2-(1-methyl-1H-imidazol-2-yl)ethyl 3-[(5-chlorothiophene-2-carbonyl)amino]-N-{2-ethyl-3-[(3S)-3-hydroxy-2-oxopyrrolidin-1-yl]benzene-1-sulfonyl}-S-alaninate (30 mg, 48.1 mmol, Example 1) while stirring. The solution was cooled to rt, 1 M phosphoric acid (48.7 mg, 46.38 mmol) was added and the mixture was stirred for 2 d at rt in a capped glass vial. Then, the cap was replaced with a Parafilm tape, 2-5 holes were punched into the tape with a needle and the mixture was gently stirred for another 10 d at rt, allowing the solvent to slowly evaporate. The title compound was obtained as a solid.

LC-MS (Method 7): $R_t$=1.03 min; MS (ESIpos): m/z=624 [M+H]$^+$ $^1$H NMR (500 MHz, DMSO-d$_6$) δ [ppm]: 9.10 (t, 1H), 8.79-8.58 (br m, 1H), 7.82 (d, 1H), 7.57 (d, 1H), 7.47-7.40 (m, 1H), 7.40-7.35 (m, 1H), 7.17 (d, 1H), 7.08 (s, 1H), 6.82 (s, 1H), 4.30 (t, 1H), 4.25-4.11 (m, 2H), 4.09-4.04 (m, 1H), 3.65-3.57 (m, 1H), 3.54 (s, 3H), 3.51-3.37 (m, 3H), 2.93-2.77 (m, 4H), 2.47-2.39 (m, 1H), 1.97-1.90 (m, 1H), 1.06 (t, 3H).

Figure 7:
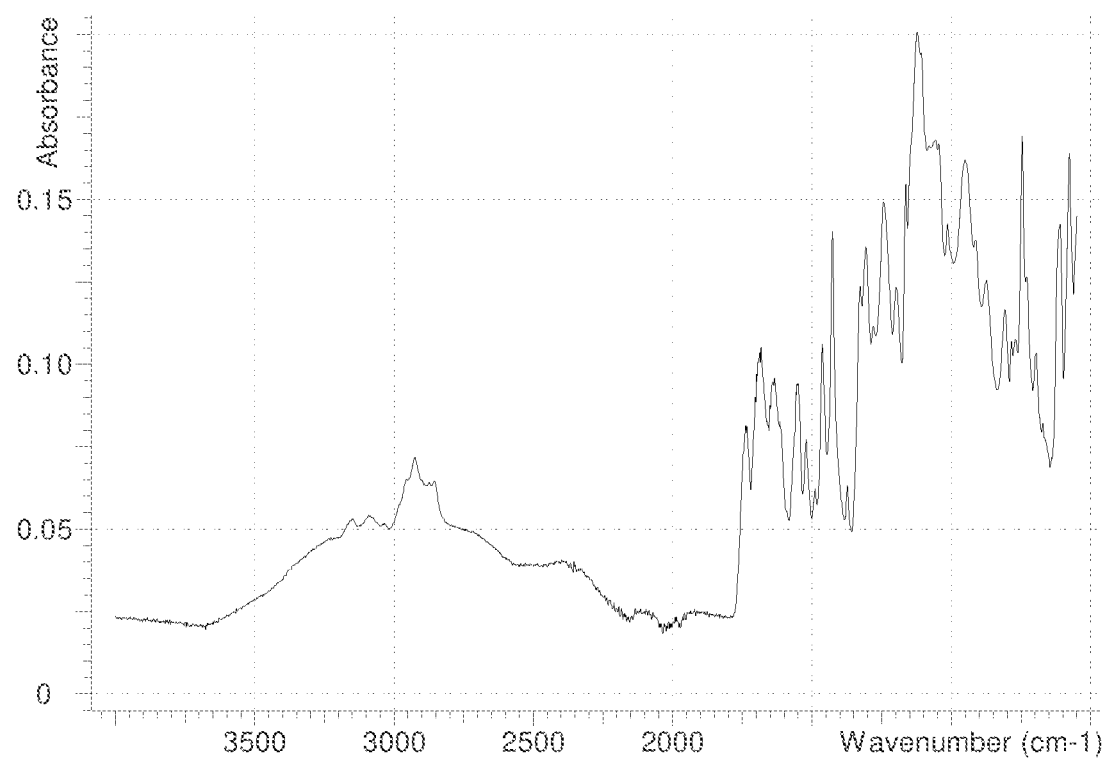
FIG. 7: Infrared spectrum of Example 7

XRPD: amorphous; IR: See FIG. 7

Example 8

2-(1-Methyl-1H-imidazol-2-yl)ethyl 3-{[(5-chloro-2-thienyl)carbonyl]amino}-N-({2-ethyl-3-[(3S)-3-hydroxy-2-oxopyrrolidin-1-yl]phenyl}sulfonyl)-S-alaninate (2R,3R)-tartrate To ethyl acetate (2.0 ml) at 60° C. was added 2-(1-methyl-1H-imidazol-2-yl)ethyl 3-[(5-chlorothiophene-2-carbonyl)amino]-N-{2-ethyl-3-[(3S)-3-hydroxy-2-oxopyrrolidin-1-yl]benzene-1-sulfonyl}-S-alaninate (30 mg, 48.1 mmol, Example 1) while stirring. The solution was cooled to rt, (2R,3R)-tartaric acid (7.4 mg, 49.3 mmol) was added and the mixture was stirred for 2 d at rt in a capped glass vial. Then, the cap was replaced with a Parafilm tape, 2-5 holes were punched into the tape with a needle and the mixture was gently stirred for another 10 d at rt, allowing the solvent to slowly evaporate. The title compound was obtained as a solid.

LC-MS (Method 7): $R_t$=1.03 min; MS (ESIpos): m/z=624 [M+H]$^+$ $^1$H NMR (500 MHz, DMSO-d$_6$) δ [ppm]: 9.09 (br t, 1H), 8.67 (br s, 1H), 7.82 (d, 1H), 7.57 (d, 1H), 7.44 (d, 1H), 7.38 (t, 1H), 7.17 (d, 1H), 7.06 (s, 1H), 6.78 (s, 1H), 4.30 (t, 1H), 4.25-4.22 (m, 2H), 4.22-4.10 (m, 2H), 4.06-4.00 (m, 1H), 3.53 (s, 3H), 3.50-3.38 (m, 3H), 2.92-2.74 (m, 4H), 2.47-2.40 (m, 1H), 1.98-1.90 (m, 1H), 1.06 (t, 3H).

Figure 8:
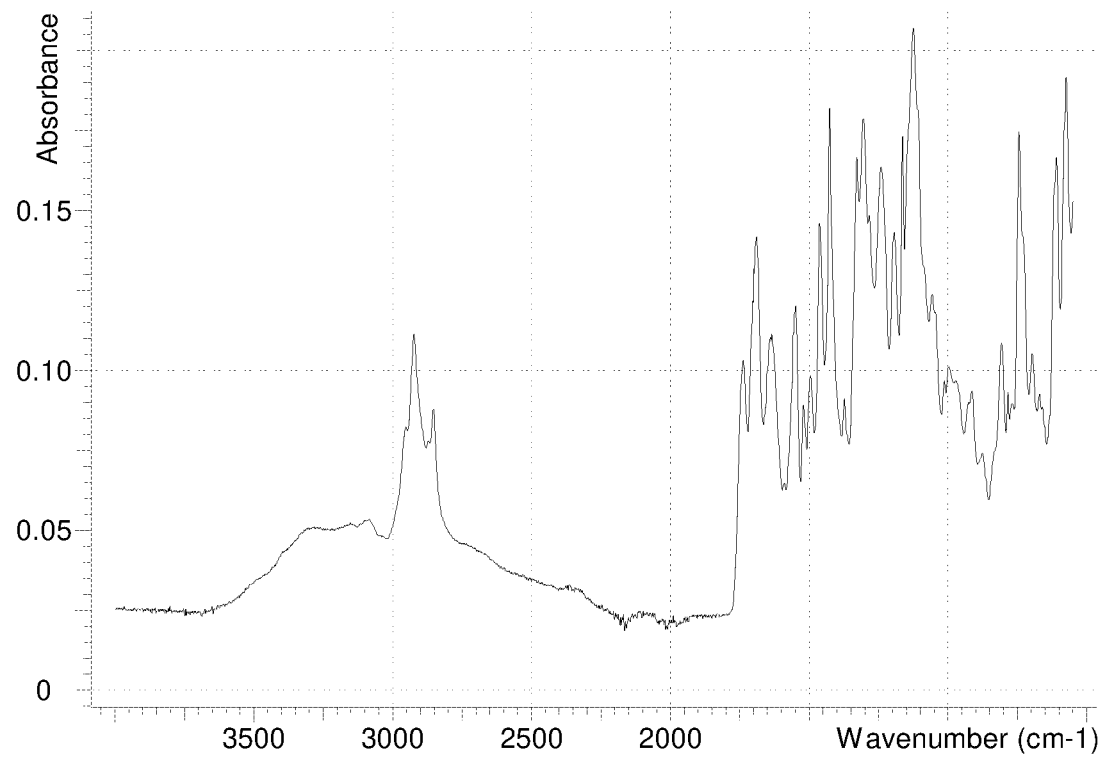
FIG. 8: Infrared spectrum of Example 8

XRPD: amorphous; IR: See FIG. 8

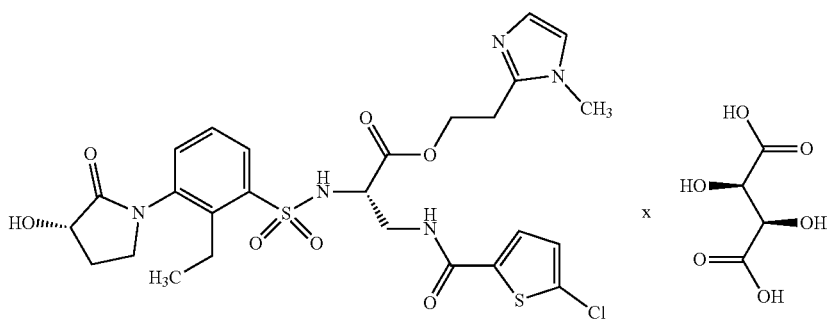

Example 9

2-(1-Methyl-1H-imidazol-2-yl)ethyl 3-{[(5-chloro-2-thienyl)carbonyl]amino}-N-({2-ethyl-3-[(3S)-3-hydroxy-2-oxopyrrolidin-1-yl]phenyl}sulfonyl)-S-alaninate citrate

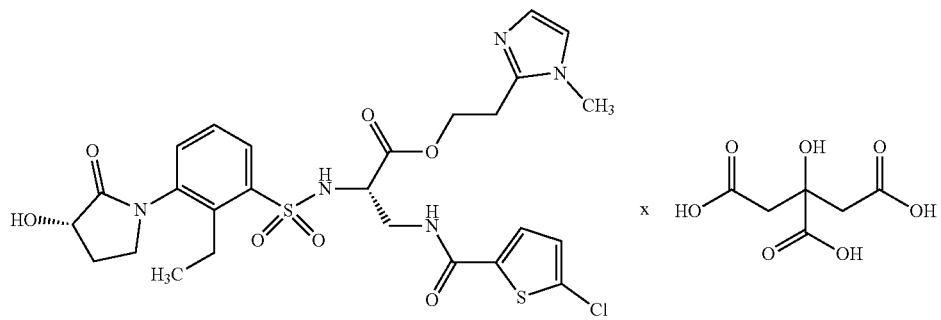

To ethyl acetate (10.0 ml) at 60° C. was added 2-(1-methyl-1H-imidazol-2-yl)ethyl 3-[(5-chlorothiophene-2-carbonyl)amino]-N-{2-ethyl-3-[(3S)-3-hydroxy-2-oxopyrrolidin-1-yl]benzene-1-sulfonyl}-S-alaninate (100 mg, 160.2 mmol, Example 1) while stirring. The solution was cooled to rt and solution of citric acid (31 mg, 161.4 mmol) in ethyl acetate (8 ml) was added at rt, resulting in precipitation of a white solid. The mixture was stirred for 5 d at rt in a capped glass vial, after which the precipitate was filtered off and dried at the air to give the title compound as a solid.

LC-MS (Method 7): $R_t$=1.02 min; MS (ESIpos): m/z=624 [M+H]$^{30}$ $^1$H NMR (500 MHz, DMSO-d$_6$) δ [ppm]: 9.01 (t, 1H), 8.66 (d, 1H), 7.82 (dd, 1H), 7.56 (d, 1H), 7.44 (dd, 1H), 7.37 (t, 1H), 7.17 (d, 1H), 7.15 (d, 1H), 6.91 (s, 1H), 4.30 (t, 1H), 4.25-4.11 (m, 2H), 4.07-4.01 (m, 1H), 3.65-3.58 (m, 1H), 3.57 (s, 3H), 3.50-3.40 (m, 3H), 2.92-2.79 (m, 4H), 2.70 (d, 2H), 2.61 (d, 2H), 2.48-2.40 (m, 1H), 1.98-1.90 (m, 1H), 1.06 (t, 3H).

Figure 9:
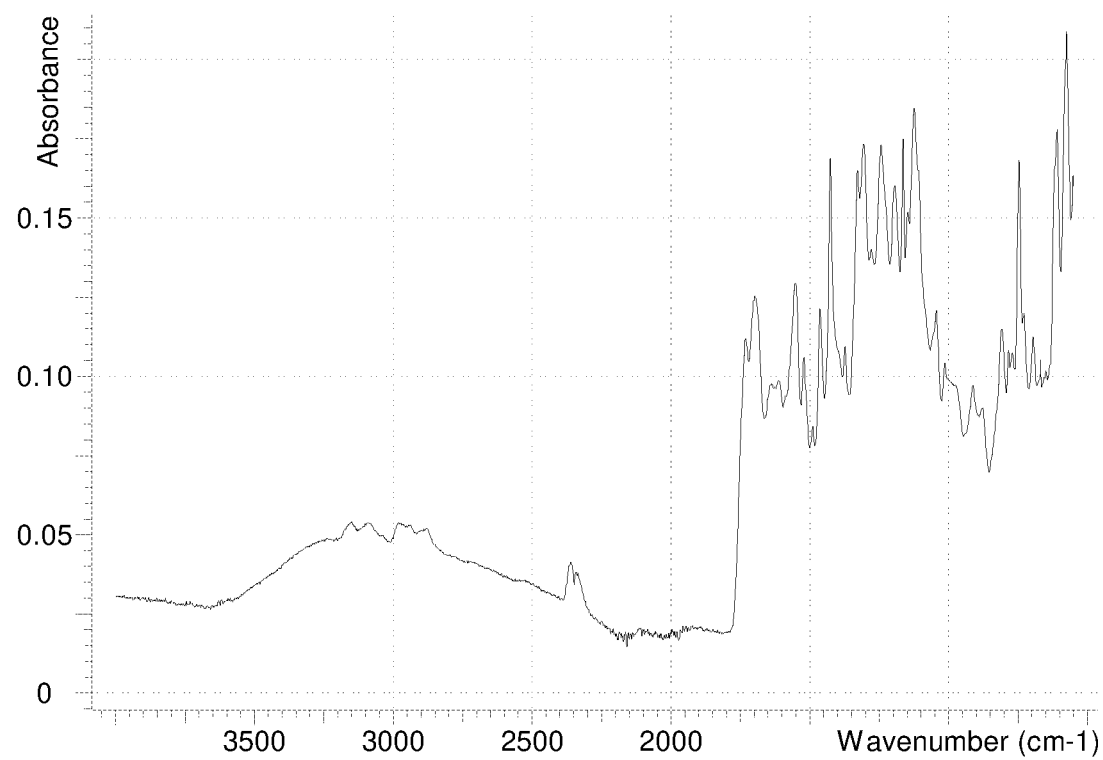
FIG. 9: Infrared spectrum of Example 9

XRPD: amorphous; IR: See FIG. 9

TABLE 1

Infrared spectroscopy of Example 1 and the salt forms (Example 2 to 9)
Band maxima (cm$^{-1}$)

| Example 1 | Example 2 Hydrochloride Salt | Example 3 Sulfate Salt | Example 4 Mesylate Salt | Example 5 Tosylate Salt | Example 6 Maleate Salt | Example 7 Phosphate Salt | Example 8 Tartrate Salt | Example 9 Citrate Salt |
|---|---|---|---|---|---|---|---|---|
| 552 | 552 | 575 | 552 | 566 | 572 | 575 | 574 | 576 |
| 577 | 577 | 608 | 576 | 610 | 610 | 609 | 610 | 609 |
| 609 | 609 | 694 | 609 | 680 | 650 | 671 | 660 | 651 |
| 618 | 618 | 730 | 694 | 711 | 694 | 695 | 670 | 668 |
| 655 | 655 | 745 | 728 | 730 | 727 | 730 | 697 | 695 |
| 668 | 668 | 770 | 746 | 746 | 745 | 745 | 744 | 728 |
| 694 | 694 | 784 | 772 | 769 | 784 | 769 | 768 | 746 |
| 728 | 728 | 809 | 809 | 784 | 806 | 784 | 784 | 770 |
| 745 | 745 | 856 | 879 | 815 | 864 | 807 | 807 | 784 |
| 770 | 770 | 915 | 915 | 877 | 912 | 874 | 876 | 808 |
| 784 | 784 | 1016 | 964 | 919 | 978 | 912 | 914 | 877 |
| 808 | 808 | 1042 | 1016 | 1009 | 993 | 950 | 926 | 913 |
| 878 | 878 | 1125 | 1039 | 1032 | 1012 | 1013 | 973 | 1014 |
| 922 | 922 | 1148 | 1124 | 1120 | 1043 | 1044 | 997 | 1043 |
| 973 | 973 | 1163 | 1163 | 1163 | 1106 | 1058 | 1013 | 1110 |
| 1013 | 1013 | 1190 | 1190 | 1190 | 1123 | 1080 | 1045 | 1124 |
| 1043 | 1043 | 1224 | 1306 | 1224 | 1147 | 1107 | 1056 | 1147 |
| 1122 | 1122 | 1281 | 1328 | 1282 | 1164 | 1123 | 1125 | 1164 |
| 1146 | 1146 | 1305 | 1373 | 1306 | 1194 | 1163 | 1164 | 1193 |
| 1164 | 1164 | 1328 | 1427 | 1328 | 1242 | 1198 | 1193 | 1243 |
| 1194 | 1194 | 1373 | 1463 | 1374 | 1280 | 1243 | 1241 | 1279 |
| 1242 | 1242 | 1426 | 1489 | 1426 | 1306 | 1279 | 1284 | 1306 |
| 1280 | 1280 | 1463 | 1524 | 1463 | 1328 | 1306 | 1304 | 1328 |
| 1304 | 1304 | 1489 | 1553 | 1494 | 1352 | 1327 | 1328 | 1373 |
| 1327 | 1327 | 1520 | 1609 | 1521 | 1373 | 1373 | 1373 | 1426 |
| 1373 | 1373 | 1553 | 1644 | 1552 | 1426 | 1426 | 1426 | 1463 |
| 1426 | 1426 | 1609 | 1695 | 1608 | 1461 | 1463 | 1461 | 1489 |
| 1462 | 1462 | 1635 | 1742 | 1645 | 1520 | 1489 | 1495 | 1520 |
| 1488 | 1488 | 1683 | | 1699 | 1549 | 1520 | 1520 | 1552 |
| 1520 | 1520 | 1743 | | 1745 | 1580 | 1549 | 1549 | 1587 |
| 1549 | 1549 | | | | 1615 | 1635 | 1635 | 1611 |
| 1605 | 1605 | | | | 1694 | 1683 | 1688 | 1637 |

TABLE 1-continued

Infrared spectroscopy of Example 1 and the salt forms (Example 2 to 9)
Band maxima (cm$^{-1}$)

| Example 1 | Example 2 Hydrochloride Salt | Example 3 Sulfate Salt | Example 4 Mesylate Salt | Example 5 Tosylate Salt | Example 6 Maleate Salt | Example 7 Phosphate Salt | Example 8 Tartrate Salt | Example 9 Citrate Salt |
|---|---|---|---|---|---|---|---|---|
| 1641 | 1641 | | | | 1742 | 1738 | 1699 | 1699 |
| 1652 | 1652 | | | | | | 1738 | 1730 |
| 1695 | 1695 | | | | | | | |
| 1699 | 1699 | | | | | | | |
| 1738 | 1738 | | | | | | | |

B) Assessment of Physiological Efficacy

The suitability of the compounds according to the invention for treating thromboembolic disorders can be demonstrated in the following assay systems:

a) Test Descriptions (In Vitro)

a.1) Measurement of the Factor Xa Inhibition in Buffer

To determine the factor Xa inhibition of the substances listed above, a biological test system is constructed in which the conversion of a factor Xa substrate is used for determining the enzymatic activity of human factor Xa. Here, factor Xa cleaves aminomethylcoumarin, which is measured fluorescently, from the peptidic substrate. The determinations are carried out in microtitre plates.

Substances to be tested are dissolved in various concentrations in dimethyl sulphoxide and incubated for 30 min with human factor Xa (1.3 nmol/l dissolved in 50 mmol/l of Tris buffer [C,C,C-tris(hydroxymethyl)aminomethane], 100 mmol/l of sodium chloride, 5 mmol/l of calcium chloride, 0.1% BSA [bovine serum albumin], pH 7.4) at 22° C. The substrate (5 μmol/l Boc-Ile-Glu-Gly-Arg-AMC from Bachem) is then added. After 30 min of incubation, the sample is excited at a wavelength of 360 nm and the emission is measured at 460 nm. The measured emissions of the test batches with test substance are compared to the control batches without test substance (only dimethyl sulphoxide instead of test substance in dimethyl sulphoxide) and the IC$_{50}$ values are calculated from the concentration/activity relationships. Representative activity data from this test are listed in Table 2a and 2b below.

a.2) Measurement of Thrombin Inhibition in Buffer

To determine the thrombin inhibition of the substances listed above, a biological test system is constructed in which the conversion of a thrombin substrate is used for determining the enzymatic activity of human thrombin. Here, thrombin cleaves aminomethylcoumarin, which is measured fluorescently, from the peptidic substrate. The determinations are carried out in microtitre plates.

Substances to be tested are dissolved in various concentrations in dimethyl sulphoxide and incubated for 15 min with human thrombin (0.06 nmol/l dissolved in 50 mmol/l of Tris buffer [C,C,C-tris(hydroxymethyl)aminomethane], 100 mmol/l of sodium chloride, 0.1% BSA [bovine serum albumin], pH 7.4) at 22° C. The substrate (5 μmol/l Boc-Asp (OBzl)-Pro-Arg-AMC from Bachem) is then added. After 30 min of incubation, the sample is excited at a wavelength of 360 nm and the emission is measured at 460 nm. The measured emissions of the test batches with test substance are compared to the control batches without test substance (only dimethyl sulphoxide instead of test substance in dimethyl sulphoxide) and the IC$_{50}$ values are calculated from the concentration/activity relationships. Representative activity data from this test are listed in Table 2a and 2b below.

a.3) Determination of the Selectivity

To demonstrate the selectivity of the substances with respect to thrombin and factor Xa inhibition, the test substances are examined for their inhibition of other human serine proteases, such as factor factor XIa, trypsin, plasmin, tissue plasminogen activator (TPA), and plasma kallikrein. The determinations are carried out in microtitre plates. To determine the enzymatic activity of factor XIa (0.15 nmol/l from Kordia), trypsin (42 mU/ml from Sigma), plasmin (0.1 μg/ml from Kordia), TPA (1 nmol/l from Kordia) and plasma kallikrein (0.2 nmol/l from Loxo), these enzymes are dissolved (50 mmol/l of Tris buffer [C,C,C-tris(hydroxymethyl)aminomethane], 100 mmol/l of sodium chloride, 0.1% BSA [bovine serum albumin], 5 mmol/l of calcium chloride, pH 7.4) and incubated for 15 min with test substance in various concentrations in dimethyl sulphoxide and also with dimethyl sulphoxide without test substance. The enzymatic reaction is then started by addition of the appropriate substrates (5 μmol/l of Boc-Glu(OBzl)-Ala-Arg-AMC from Bachem for factor XIa, 5 μmol/l of Boc-Ile-Glu-Gly-Arg-AMC from Bachem for Trypsin, 50 μmol/l of MeOSuc-Ala-Phe-Lys-AMC from Bachem for plasmin, 5 μmol/l of CH3SO2-D-Phe-Gly-Arg-AMC from Pentapharm for TPA and 5 μmol/l of H-Pro-Phe-Arg-AMC from Bachem for plasma kallikrein). After an incubation time of 30 min at 22° C., fluorescence is measured (excitation: 360 nm, emission: 460 nm). The measured emissions of the test batches with test substance are compared to the control batches without test substance (only dimethyl sulphoxide instead of test substance in dimethyl sulphoxide), and the IC$_{50}$ values are calculated from the concentration/activity relationships. Representative activity data from this test are listed in Table 2a and 2b below.

TABLE 2a

| Reference No. | FXa IC$_{50}$ [nM] | FIIa IC$_{50}$ [nM] | FXIa IC$_{50}$ [nM] | Trypsin IC$_{50}$ [nM] | Plasmin IC$_{50}$ [nM] | TPA IC$_{50}$ [nM] | Kallikrein IC$_{50}$ [nM] |
|---|---|---|---|---|---|---|---|
| Reference 1 | 0.43 | 0.19 | >49000 | 2700 | 22000 | 2300 | 2600 |
| Reference 2 | 1.1 | 15 | >50000 | 32000 | >50000 | 16000 | 11000 |
| Reference 3 | 2.3 | 300 | >50000 | 14000 | >50000 | 23000 | 7600 |
| Reference 4 | 0.49 | 26 | >50000 | 41000 | >50000 | 1200 | 5700 |

TABLE 2a-continued

| Reference No. | FXa IC$_{50}$ [nM] | FIIa IC$_{50}$ [nM] | FXIa IC$_{50}$ [nM] | Trypsin IC$_{50}$ [nM] | Plasmin IC$_{50}$ [nM] | TPA IC$_{50}$ [nM] | Kallikrein IC$_{50}$ [nM] |
|---|---|---|---|---|---|---|---|
| Reference 5 | 0.54 | 9.7 | >50000 | 30000 | >50000 | 960 | 1200 |
| Reference 6 | 0.68 | 70 | >50000 | 20000 | >50000 | 3100 | 2300 |
| Reference 7 | 0.76 | 52 | 47000 | 15000 | >50000 | 790 | 1400 |
| Reference 8 | 0.45 | 1.7 | 17000 | 3200 | 9100 | 2300 | 650 |
| Reference 9 | 0.89 | 0.83 | 7200 | 1500 | 15000 | 7900 | 260 |
| Reference 10 | 0.63 | 0.74 | 9300 | 2600 | 13000 | 2500 | 230 |
| Reference 11 | 0.48 | 1.8 | 8300 | 3000 | 4900 | 1300 | 33 |
| Reference 12 | 0.61 | 16 | >50000 | 2000 | 19000 | 1100 | 1600 |
| Reference 13 | 1.1 | 35 | 33000 | 3500 | 21000 | 4000 | 2300 |
| Reference 14 | 0.68 | 4.9 | 7500 | 1400 | 13000 | 1800 | 520 |
| Reference 15 | 0.93 | 18 | 18000 | 2900 | 8300 | >4000 | 99 |
| Reference 16 | 0.79 | 10 | 8100 | 1300 | 4200 | 780 | 62 |

Values are rounded to two significant digits.

TABLE 2b

| Example No. | FXa IC$_{50}$ [nM] | FIIa IC$_{50}$ [nM] | FXIa IC$_{50}$ [nM] | Trypsin IC$_{50}$ [nM] | Plasmin IC$_{50}$ [nM] | TPA IC$_{50}$ [nM] | Kallikrein IC$_{50}$ [nM] |
|---|---|---|---|---|---|---|---|
| Example 1 | 0.71 | 5.3 | 36000 | 3200 | 16000 | 7400 | 420 |
| Example 2 | 0.66 | 4.9 | 31000 | 2700 | 15000 | 6500 | 380 |
| Example 3 | 0.78 | 5.9 | n.d. | n.d. | n.d. | n.d. | n.d. |
| Example 4 | 0.52 | 4.0 | n.d. | n.d. | n.d. | n.d. | n.d. |
| Example 5 | 0.78 | 5.8 | n.d. | n.d. | n.d. | n.d. | n.d. |
| Example 6 | 0.51 | 4.5 | n.d. | n.d. | n.d. | n.d. | n.d. |
| Example 7 | 0.56 | 5.2 | n.d. | n.d. | n.d. | n.d. | n.d. |
| Example 8 | 0.85 | 6.0 | n.d. | n.d. | n.d. | n.d. | n.d. |
| Example 9 | 0.49 | 4.6 | n.d. | n.d. | n.d. | n.d. | n.d. | n.d.: not determined
Values are rounded to two significant digits.

a.4) Determination of the Factor Xa-Inhibitory Activity of the Potential Inhibitors in Plasma Samples To determine the inhibition of factor Xa in plasma samples, the factor X present in plasma is activated by a protease from rattlesnake toxin. The factor Xa activity or its inhibition by potential inhibitors is then measured by addition of a chromogenic substrate.

Various concentrations of the substances to be tested are dissolved in dimethyl sulphoxide and mixed with an aqueous refludan solution (10 µg/ml). In clear 96-well plates having a flat bottom, 30 µl of citrate plasma (Octapharma) are mixed with 10 µl of the substance dilution. Then, either 20 µl of a solution of a rattlesnake toxin (Russel viper venom (RVV); RVV reagent: Pentapharm 121-06, final concentration 0.6 mU) in an aqueous calcium chloride solution buffer (final concentration of calcium chloride 0.05 M) or 20 µl of the aqueous calcium chloride solution (final concentration of calcium chloride 0.05 M) without RVV reagent (as reference for an unstimulated sample) are added. After addition of 20 µl of ChromozymX substrate (final concentration 1.6 mmol/l, Bachem L-1565, diluted in water) the samples are measured in a SpectraFluor Reader using a measurement filter of 405 nm each minute over a period of 20 minutes. The IC$_{50}$ value is determined when about 70% of the maximum signal is reached (about 12 min). Representative activity data from these tests are listed in Tables 3a and 3b below.

a.5) Determination of the Thrombin-Inhibitory Activity of the Potential Inhibitors in Plasma Samples Various concentrations of the substances to be tested are dissolved in dimethyl sulphoxide and diluted with water. In white 96-well plates having a flat bottom, 20 µl of substance dilution are mixed with 20 µl of ecarin solution (ecarin reagent, from Sigma E-0504, final concentration 20 mU per batch) in Ca buffer (200 mM Hepes+560 mM sodium chloride+10 mM calcium chloride+0.4% PEG) or with 20 µl of Ca buffer (as unstimulated control). Furthermore, 20 µl of fluorogenic thrombin substrate (from Bachem I-1120, final concentration 50 µmol/l) and 20 µl of citrate plasma (from Octapharma) are added and homogenized thoroughly. The plate is measured in a SpectraFluorplus Reader using an excitation filter of 360 nm and an emission filter of 465 nm each minute over a period of 20 minutes. The IC$_{50}$ value is determined when about 70% of the maximum signal is reached (about 12 min). Representative activity data from these tests are listed in Tables 3a and 3b below.

TABLE 3a

| Reference No. | FXa IC$_{50}$ [nM] in plasma | FIIa IC$_{50}$ [nM] in plasma | Ratio FIIa IC$_{50}$/FXa IC$_{50}$ |
|---|---|---|---|
| Reference 1 | 3.3 | 16 | 4.8 |
| Reference 2 | 6.1 | 86 | 14 |
| Reference 3 | 19 | 140 | 7.4 |
| Reference 4 | 12 | 430 | 36 |
| Reference 5 | 16 | 190 | 12 |
| Reference 6 | 17 | 610 | 36 |
| Reference 7 | 13 | 510 | 39 |
| Reference 8 | 26 | 16 | 0.62 |
| Reference 9 | 3.4 | 2.9 | 0.85 |
| Reference 10 | 4.1 | 8.5 | 2.1 |
| Reference 11 | 10 | 21 | 2.1 |
| Reference 12 | 1.1 | 79 | 72 |
| Reference 13 | 9.0 | 160 | 18 |
| Reference 14 | 6.6 | 22 | 3.3 |
| Reference 15 | 42 | 63 | 1.5 |
| Reference 16 | 7.2 | 60 | 8.3 |

Values are rounded to two significant digits.

TABLE 3b

| Example No. | FXa IC$_{50}$ [nM] in plasma | FIIa IC$_{50}$ [nM] in plasma | Ratio FIIa IC$_{50}$/FIIa IC$_{50}$ |
| --- | --- | --- | --- |
| Example 1 | 4.1 | 26 | 6.3 |
| Example 2 | 9.2 | 22 | 2.4 |
| Example 3 | 5.8 | 56 | 9.7 |
| Example 4 | 4.1 | 27 | 6.6 |
| Example 5 | 6.4 | 100 | 16 |
| Example 6 | 5.1 | 22 | 4.3 |
| Example 7 | 0.96 | 28 | 29 |
| Example 8 | 2.1 | 31 | 15 |
| Example 9 | 7.1 | 44 | 6.2 |

Values are rounded to two significant digits.

a.6) Thrombin Generation Assay (Thrombogram)

The effect of the test substances on the thrombogram (thrombin generation assay according to Hemker) is determined in vitro in human plasma (Octaplas® from Octapharma). In the thrombin generation assay according to Hemker, the activity of thrombin in coagulating plasma is determined by measuring the fluorescent cleavage products of the substrate I-1140 (Z-Gly-Gly-Arg-AMC, Bachem). Reagents from Thrombinoscope (PPP reagent: 30 pM recombinant tissue factor, 24 μM phospholipids in HEPES) are used to start the coagulation reaction. The reaction is carried out in the presence of varying concentrations of test substance or the corresponding solvent. Moreover, a thrombin calibrator from Thrombinoscope is used whose amidolytic activity is required for calculating the thrombin activity in a plasma sample.

The test is carried out according to the specifications of the manufacturer (Thrombinoscope BV): 4 μl of the test substance or of the solvent, 76 μl of plasma and 20 μl of PPP reagent or thrombin calibrator are incubated at 37° C. for 5 min. After addition of 20 μl of 2.5 mM thrombin substrate in 20 mM Hepes, 60 mg/ml of BSA, 102 mM calcium chloride, the thrombin generation is measured every 20 s over a period of 120 min. Measurement is carried out using a fluorometer (Fluoroskan Ascent) from Thermo Electron fitted with a 390/460 nm filter pair and a dispenser. Using the Thrombinoscope software, the thrombogram is calculated and presented graphically. What is calculated are the following parameters: lag time, time to peak, peak, ETP (endogenous thrombin potential) and start tail.

a.7) Determination of the Anticoagulatory Activity

The anticoagulatory activity of the test substances is determined in vitro in human plasma, rabbit plasma and rat plasma. To this end, blood is drawn off in a mixing ratio of sodium citrate/blood of 1/9 using a 0.11 molar sodium citrate solution as receiver. Immediately after the blood has been drawn off, it is mixed thoroughly and centrifuged at about 4000 g for 15 minutes. The supernatant is pipetted off.

The prothrombin time (PT, synonyms: thromboplastin time, quick test) is determined in the presence of varying concentrations of test substance or the corresponding solvent using a commercial test kit (Neoplastin® from Boehringer Mannheim or Hemoliance® RecombiPlastin from Instrumentation Laboratory). The test compounds are incubated with the plasma at 37° C. for 3 minutes. Coagulation is then started by addition of thromboplastin, and the time when coagulation occurs is determined. The concentration of test substance which effected a doubling of the prothrombin time is determined.

The thrombin time (TT) is determined in the presence of varying concentrations of test substance or the corresponding solvent using a commercial test kit (thrombin reagent from Roche). The test compounds are incubated with the plasma at 37° C. for 3 minutes. Coagulation is then started by addition of the thrombin reagent, and the time when coagulation occurs is determined. The concentration of test substance which effects a doubling of the thrombin time is determined.

The activated partial thromboplastin time (APTT) is determined in the presence of varying concentrations of test substance or the corresponding solvent using a commercial test kit (PTT reagent from Roche). The test compounds are incubated with the plasma and the PTT reagent (cephalin, kaolin) at 37° C. for 3 minutes. Coagulation is then started by addition of 25 mM calcium chloride, and the time when coagulation occurs is determined. The concentration of test substance which effects a doubling of the APTT is determined.

a.8) Thromboelastography (Thromboelastogram)

The thromboelastography is carried out with the aid of the thromboelastograph ROTEM from Pentapharm and its accessories, cup and pin. The measurement is carried out in whole blood drawn off beforehand into sodium citrate monovettes from Sarstedt. The blood in the monovettes is kept in motion using a shaker and preincubated at 37° C. for 30 min. A 2 molar stock solution of calcium chloride in water is prepared. This is diluted 1:10 with an aqueous 0.9% strength sodium chloride solution. For the measurement, 20 μl of this 200 mM calcium chloride solution are initially charged into the cups (final concentration of calcium chloride 12.5 mM). 3.2 μl of substance or solvent are added. The measurement is started by addition of 300 μl of whole blood. After the addition, using the tip of the pipette, the mixture is briefly drawn into the pipette and released again without generating air bubbles. The measurement is carried out over a period of 2.5 hours or is stopped when fibrinolysis sets in. For evaluation, the following parameters are determined: CT (clotting time/[sec.]), CFT (clotting formation time/[sec.]), MCF (maximum clot firmness/[mm]) and the alpha angle [°]. The measurement points are determined every 3 seconds and represented graphically, with the y axis for MCF [mm] and the x axis for time [sec.].

a.9) Inhibition of Ongoing Coagulation

The test compounds are dissolved as 10 mM stock solution in DMSO and a serial dilution between 0.018 and 600 μM is prepared with DMSO.

Into a white 384-well plate (Lumitrac 200, Greiner) 20 μl Octaplas (Octapharm), 10 μL destilled water, 10 μl Pefabloc FG (DSM, 24 mM) and 10 μl fluorogenic thrombinsubstrate (BACHEM, I-1560, 300 μM) are added. To initiate coagulation, 10 μl mix of Tissue Factor (Instrumentation Laboratory, Recombiplastin 2G, 0.06%) and CaCl$_2$ (40 mM) are added. The fluorescence signal generated by cleavage of the substrate is measured with the Tecan infinite M1000 Pro every 30 s for 20 min at 37° C. and 340 nm excitation and 460 nm emission wavelength. After doubling of the fluorescence signal, 1 μl of the compound solution in DMSO are added to each well and the measurement is continued. Whether a test compound can inhibit the ongoing coagulation is determined by the slope of the fluorescence signal after compound addition.

a.10) Inhibition of Tissue Factor-Initiated Platelet Aggregation

Whole blood is collected by venipuncture from healthy male and female humans. Samples are placed into vacutainer tubes containing 1/10 volume of 3.12% trisodium citrate, and platelet-rich plasma (PRP) is obtained by immediate centrifugation of the blood at 140 g for 20 minutes at 20° C.

To adjust the platelet count, PRP is diluted with platelet-poor plasma to 300000-350000 platelets/μl. Platelet-poor plasma is obtained by centrifugation of PRP at 1000 g for 20 minutes at 20° C. Pefabloc FG (Pentapharm, Basel, Switzerland) is dissolved in demineralized water (2 mg/ml; final concentration) and added to prevent fibrin polymerization. After the addition of $CaCl_2$ (7 mmol/l, final concentration), aliquots (178 µl) are immediately placed in the aggregometer (Apact 4, DiaSys Greiner, Flacht, Germany). The samples are spiked with 2 µl of increasing concentrations of test compound (plasma concentrations 0.3-10 µmol/l) or vehicle and are incubated for 3 minutes at 37° C. Platelet aggregation is induced by the addition of 20 ml of tissue factor (RecombiPlasTin 2G; Instrumentation Laboratory), dissolved in an aqueous solution of 10 mmol/l $CaCl_2$ (as per the manufacturer's instructions). Individual tissue factor concentrations (dilution 1:10-1:2500 with 10 mmol/l $CaCl_2$ solution) are used to achieve the minimum tissue factor concentration for each experiment, resulting in maximal aggregation. Aggregation is measured turbidimetrically and recorded over 10 minutes and the aggregation response is evaluated as the area under the concentration-time curve. The $IC_{50}$ values are calculated using the Boltzmann test (GraphPad Prism).

a.11) Inhibition of LPS- or Heat-Inactivated *Staphylococcus aureus*-Induced Coagulation in Whole Blood $10^{10}$ cells of Heat-killed *Staphylococcus aureus* (Invivo-Gen) are dissolved in 1 ml water and solutions containing $10^9$ to $10^6$ cells are prepared by dilution in aqueous 0.9% NaCl solution. Lipopolysaccharide (LPS, Sigma) is dissolved in in aqueous 0.9% NaCl solution to yield a 0.005 mg/ml solution.

Fresh whole blood is collected by venipuncture from healthy male and female humans into vacutainer tubes containing 1/10 volume of 3.12% trisodium citrate. 10 µl of a solution of the test compound (0-20 µM, final concentration) in DMSO and 10 µl of the trigger solutions containing Heat-killed *Staphylococcus aureus* or LPS are added to 980 µl of the citrated whole blood, gently mixed and incubated for 4 h at 37° C.

150 µl of the mixture and 20 µl of an 0.1 M solution of calcium chloride are added into cuvettes to start the clotting time measurement (Apact 4, DiaSys Greiner, Flacht, Germany). Clotting times of control samples and compound samples at various concentrations are compared to calculate the concentration needed for doubling of the clotting time using GraphPad Prism.

a.12) Impact on the Integrity of an Endothelial Layer in the Presence of Thrombin 50 µl of endothelial cell basal medium-2 (EBM-2) supplemented with human recombinant epidermal growth factor (hEGF), human fibroblast growth factor-basic with heparin (hFGF-B), vascular endothelial growth factor (VEGF), ascorbic acid, hydrocortisone, human recombinant insulin-like growth factor (long R3-IGF-1), heparin, GA-1000 and 2% fetal bovine serum (FBS) are filled into each well of an E-Plate 96 (OLS Omni Life, Germany), which is then placed on an ACEA—Xcelligence RTCA instrument (Agilent, USA) to measure the background impedance of the media.

Cryopreserved Pooled Human Umbilical Vein Endothelial Cells (HUVEC; Lonza, Germany; C2519a) are propagated and maintained in endothelial cell basal medium-2 (EBM-2) supplemented with human recombinant epidermal growth factor (hEGF), human fibroblast growth factor-basic with heparin (hFGF-B), vascular endothelial growth factor (VEGF), ascorbic acid, hydrocortisone, human recombinant insulin-like growth factor (long R3-IGF-1), heparin, GA-1000 and 2% fetal bovine serum (FBS). The cells are cultured at 37° C. in humidified air containing 5% $CO_2$.

50 µl of media containing 20000 cells at passage 3 are added into each well. The plate is kept at 37° C. and 5% $CO_2$ for 24 h in the incubator of the Xcelligence RTCA instrument. Then, 10 µl of a solution of the test compound in DMSO or DMSO alone are added to each well and the impedance is measured every 5 min over 30 min. Subsequently, 40 µl of a solution of thrombin (final concentration 0.1 U/ml) are added and the impedance is measured again every 5 min for 190 min.

The strength of cell adhesion is represented by the RTCA software as the Cell Index and compared between the different compound concentration with the blank experiments using Graphpad Prism.

b) Determination of Antithrombotic Activity (In Vivo)

b.1) Arteriovenous Shunt and Bleeding Model (Combination Model Rabbit)

Male rabbits (New Zealand White Rabbit; Crl:KBL (NZW) with a weight of 2700-3500 g are anaesthetized with 2% Xylazin (Rompun, Bayer Vital) and 100 mg/ml Ketamine (Ketaset, Zoetis). Thrombos formation is initiated in an arterviovenous shunt according to the method described by Christopher N. Berry et al., Br. J. Pharmacol. (1994), 113, 1209-1214. To this end, the left Vena facialis and the right Arteria carotis are dissected. An extracorporal shunt of 10 cm polyethylene tube is used to connect both vessels. This tube is placed in another 4 cm long polyethylene tube (PE 240), which contains a 6 cm nylon thread (0.14 mm diameter), which has been roughened with sandpaper and has been folded to form a loop of 3 cm. This thread provides a thrombogenic surface necessary to induce coagulation. The extracorporal circulation is maintained for 15 min before the shunt is removed and the nylon thread is weighed together with the thrombus. The tare weight of the nylon thread is determined prior to the experiment. In order to determine the bleeding time, a 0.5 cm cut is performed next to the peripheral ear vein with a sterile scalpel. Every 30 s, blood is swabbed with a filter paper until the bleeding has ceased. The test compounds are given as a continuous intravenous infusion 30 min prior to opening the arteriovenous shunt via the Vena femoralis.

b.2) Determination of the Efficacy in Endotoxinemia Models (In Vivo)

b.2.1) LPS-Induced Endotoxinemia Rabbit Model

The experiment is performed in anesthetized male rabbits (New Zealand White rabbits). Anesthesia is induced by an intramuscular injection of 5 mg/kg of 2% Xylazine (Rompun, Bayer Vital) and 40 mg/kg of 100 mg/ml Ketamine (Ketavet, Pfizer) followed by a continuous infusion of 2% Xylazine (Rompun, Bayer Vital) and 100 mg/ml Ketamine (Ketavet, Pfizer).

To induce endotoxinemia, 100 µg/kg/h Lipopolysaccharide from *E. coli* (LPS 055:B5; Sigma-Aldrich; LOT 025M4040V) are continuously infused via the left Vena femoralis for 8 h. The test compounds are continuously infused via the right Vena femoralis. For continuous measurement of hemodynamic parameters, such as the heart rate and arterial blood pressure, a micro-tip pressure catheter (SPR-595; Millar Instruments) is implanted into the left Arteria femoralis. Arterial blood samples are collected once per hour via the right Arteria femoralis for 8 h. Readout parameters obtained from the whole blood samples include blood cell counts (thrombocytes, leukocytes, erythrocytes), coagulation parameters (PT, aPTT), and rotational thromboelastography (ROTEM). Plasma is produced from a part of the whole blood to determine markers of inflammation (IL-6, TNF-alpha), fibrinogen levels and biomarkers of end-organ damage, such as serum creatinine or liver enzymes such as ALT and AST.

b.2.2) Baboon Model of Sepsis Induced by Infusion of Heat-Inactivated Staph. aureus Animals are fasted for 12 h before the procedure and given water ad libitum. Each animal is identified by its unique tattoo number. Animals are weighed prior to the experiment to calculate the proper dose of anesthetic and bacteremia challenge.

Animals are first sedated with ketamine hydrochloride (14-20 mg/kg/IM) then anesthetized with sodium pentobarbital (25 mg/kg/IV) given every 30 min or as deemed necessary to maintain anesthesia, by monitoring the eyelid and toe pinch reflexes. The anesthetized animals are continuously monitored and appropriate levels of anesthetic and life support are available for the duration of the procedure. During anesthesia, the animals are turned from side to side half way through the 8-10 h anesthesia to prevent lung hypostatic congestion. An intravenous catheter is placed to provide access for fluids and medication. Saline is infused at the rate of ~5 ml/kg/hr. during the 8-10 hr. anesthesia to minimize the effects of anesthesia on hydration and to replace loss of blood volume due to blood sampling. Oral intubation is performed under anesthesia using a King vision Video laryngoscope to prevent aspiration pneumonia and allow assisted respiration if required.

Guided by ultrasound, a 18-20 gauge venocath (short line catheter) is implanted in the brachial vein for the bacterial infusion and a 18-20 gauge intracath (long line catheter) is implanted in the saphenous vein for infusion of the test compounds.

To prevent hypothermia, animals are placed on a recirculating water heated pad (37° C.) and all extremities are covered with sleeves/socks to keep the animal warm.

Heat-inactivated S. aureus, (strain B17266 Rosenbach; ATCC 49496) are infused at $3 \times 10^{10}$ bacteria/kg in 1.5 ml/kg sterile saline solution intravenously as a slow continuous infusion for 2 hours. Blood draws are performed. While under anesthesia, blood samples are collected at T0, 2, 4, 6, and 8 hours post bacterial challenge. For all experiments, blood is also drawn after 24, and 48 hrs., prior to euthanasia. 5-10 mL blood samples are taken from an indwelling saphenous vein catheter or by venipuncture. Blood samples are analyzed for the presence of inflammatory and blood clotting markers.

c) Determination of the Pharmacokinetic Properties of the Test Compounds c.1) Pharmacokinetic/Pharmacodynamic Studies in Minipigs Male or female Göttingen minipigs (Ellegard) are anesthetized by an intramuscular injection of 20 mg/kg Ketamine (Ketaset, Zoetis), 8 mg/kg Azaperon (Stresnil, Elanco) and 0.03 mg/kg Atropinsulfate (Atropin, B. Braun). Anesthesia is maintained by a bolus injection of 3 mg/kg Ketamine and 0.5 mg/kg Midazolam (Dormicum, Cheplapharm) into the peripheral ear vein followed by a continuous infusion of 22 mg/kg/h Ketamine and 3.4 mg/kg/h Midazolam. A tracheal tubus (Super Safety Clear, I.D. 4 mm; Rdsch) is implanted to allow mechanical ventilation (Avance CS²; GE Healthcare). Prior to intubation a bolus injection of 0.03 mg/kg Pancuronium (Inresa) is given via the peripheral ear vein to induce muscle relaxation. To maintain muscle relaxation, a continuous intravenous infusion of 0.3 mg/kg/h Pancuronium is given. Ringer-Lactate solution is given intravenously to maintain hydration of the animals.

Test compounds are continuously infused via the right Vena femoralis for up to 180 min. Arterial blood is collected to determine whole-blood coagulation (PT, aPTT) and for pharmacokinetic analysis after precipitation with 3 parts of acetonitrile. After infusion of the test compound has been stopped, additional blood draws are performed to monitor the pharmacological and pharmacokinetic half-lives of the test compounds.

c.2) Pharmacokinetic/Pharmacodynamic Studies in Rabbits

Male rabbits (New Zealand White) are anaesthetized with an intramuscular injection of 5 mg/kg Xylazine (Rompun, Bayer Vital) and 40 mg/kg Ketamine (Ketavet, Zoetis). Anesthesia is maintained with a continuous intravenous infusion of Xylazine and Ketamine via the right peripheral ear vein. The test compounds are continuously infused via the right Vena femoralis for up to 120 min. Arterial blood is collected via the Arteria carotis for determining coagulation parameters (PT, aPTT) and for pharmacokinetic analysis after precipitation with 3 parts of acetonitrile. After infusion of the test compound has been stopped, additional blood draws are performed to monitor the pharmacological and pharmacokinetic half-lives of the test compounds.

d) Stability d.1) Hydrolytic Stability 0.15 mg of the test compound are dissolved in 0.1 ml DMSO and 0.4 ml acetonitrile. For complete dissolution, the HPLC vial with the sample solution is shaken and sonicated. Then, 1.0 ml of the respective buffer solution (e.g. citrate buffer pH 4, citrate buffer pH 5, phosphate-buffered saline pH 6.5, phosphate-buffered saline 7.4) is added and the sample is vortexed. The sample solution is analyzed by HPLC to determine the amount of the test compound and up to two byproducts at a particular time over a period of 24 h at 37° C. t(0) values result from a sample immediately taken after vortexing with buffer at rt. The peak areas (in percentage) are used for quantification. HPLC, LC/MS analysis: The starting material is analyzed for purity by HPLC. The 24 h sample is additionally analyzed by LC/MS.

HPLC conditions: Column: Nucleodur 100 C18ec 3 μm 50×2 mm; temperature: 37° C.; Different gradient systems with 1 ml TFA/l water and 1 ml TFA/l acetonitrile.

Representative hydrolytic stability data from this test in citrate buffer pH 4 are listed in Tables 4a and 4b below:

TABLE 4a

| Reference No. | Recovery [%] 1 h | Recovery [%] 2 h | Recovery [%] 4 h | Recovery [%] 24 h |
|---|---|---|---|---|
| Reference 1 | 100 | 100 | 100 | 100 |
| Reference 4 | 100 | 100 | 100 | 100 |
| Reference 14 | 100 | 100 | 99 | 97 |
| Reference 15 | 100 | 100 | 100 | 100 |

TABLE 4b

| Example No. | Recovery [%] 1 h | Recovery [%] 2 h | Recovery [%] 4 h | Recovery [%] 24 h |
|---|---|---|---|---|
| Example 1 | 101 | 100 | 100 | 98 |
| Example 2 | 100 | 100 | 99 | 97 |

Representative hydrolytic stability data from this test in PBS buffer pH 7.4 are listed in Tables 5a and 5b below:

TABLE 5a

| Reference No. | Recovery [%] 1 h | Recovery [%] 2 h | Recovery [%] 4 h | Recovery [%] 24 h |
|---|---|---|---|---|
| Reference 1 | 97 | 98 | 99 | 99 |
| Reference 4 | 99 | 98 | 96 | 82 |

TABLE 5b

| Example No. | Recovery [%] 1 h | Recovery [%] 2 h | Recovery [%] 4 h | Recovery [%] 24 h |
|---|---|---|---|---|
| Example 1 | 93 | 83 | 69 | 9 |
| Example 2 | 90 | 84 | 69 | 10 | d.2) Hydrolytic Stability

Different aqueous solutions (water, 0.1 M HCl, buffer pH 10 and buffer pH 7) of the drug substance (0.25 mg/ml drug substance in 50% aqueous solution and 50% tetrahydrofuran, acetonitrile, methanol or citrate buffer pH 4 to improve solubility) are stored for 24 h at 70° C. and one week at room temperature. Additionally, blank solutions are prepared for each stress solution, to unambiguously identify degradation peaks by comparison of the respective chromatograms. The solutions before and after storage are directly injected into the HPLC without further workup. For data evaluation, the respective chromatograms are integrated and compared to each other. Depending on the formed amount of organic impurities (<2%, 2-5% or >5%), the stability is described with the descriptors "stable", "slightly unstable" or "unstable".

d.3) Plasma Stability

The plasma stability sample preparation is performed manually or via a Hamilton robot system Assay description with manually sample preparation:

1 mg of the test compound is dissolved in 0.5 ml acetonitrile/DMSO (different ratios possible). For complete dissolution, the HPLC vial is shaken and sonicated. 20 µl of this solution containing the test compound are added to 1 ml of plasma which is kept at a temperature of 37° C. and the mixture is directly vortexed. After 0.17, 0.5, 1, 1.5, 2 and 4 hours, the enzymatic reaction is stopped by adding 100 µl of the compound plasma solution to a vial containing 300 µl acetonitrile/citrate buffer pH 3 (80:20) or acetonitrile at rt or at 10° C. The mixture is centrifuged at 5000 rpm for 10 minutes. The supernatant is analyzed by HPLC to determine the amount of the test compound and up to two byproducts. t(0) values result from a processed sample immediately taken after vortexing with plasma at rt. The peak areas (in percentage) are used for quantification. HPLC, LC/MS analysis: The starting material is analyzed for purity by HPLC. The 4 h sample is additionally analyzed by LC/MS.

Assay Description with Automated Sample Preparation (Hamilton Starlet and H-Motion-System):

1 mg of the test compound is manually dissolved in 0.5 ml acetonitrile/DMSO (different ratios possible). For complete dissolution the HPLC vial is manually shaken and sonicated. Then, automated pipetting steps are performed via robot as follows: 20 µl of this solution containing the test compound are added to 1 ml of plasma which is kept at a temperature of 37° C. and mixed with a pipette. After 0.17, 0.5, 1, 1.5, 2 and 4 hours, the enzymatic reaction is stopped by adding 100 µl of the compound plasma solution to a vial containing 300 µl acetonitrile/citrate buffer pH 3 (80:20) or acetonitrile at 10° C. The mixture is centrifuged at 5000 rpm for 10 minutes at 10° C. The supernatant is analyzed by HPLC to determine the amount of the test compound and up to two byproducts. t(0) values result from a processed sample immediately taken after vortexing with plasma at rt. The peak areas (in percentage) are used for quantification. HPLC, LC/MS analysis: The starting material is analyzed for purity by HPLC. The 4 h sample is additionally analyzed by LC/MS.

HPLC conditions: Column: Nucleodur 100 C18ec 3 µm 50×2 mm; temperature: 37° C.; Different gradient systems with 1 ml TFA/l water and 1 ml TFA/l acetonitrile.

Representative human plasma stability data from this test are listed in Tables 6a and 6b below:

TABLE 6a

| Reference No. | Recovery [%] 0.17 h | Recovery [%] 0.50 h | Recovery [%] 1.0 h | Recovery [%] 1.5 h | Recovery [%] 2.0 h | Recovery [%] 4.0 h |
|---|---|---|---|---|---|---|
| Reference 1 | 99 | 100 | 98 | 99 | 98 | 99 |
| Reference 4 | 100 | 98 | 96 | 93 | 90 | 79 |
| Reference 9 | 100 | 98 | 91 | 88 | 84 | 68 |
| Reference 10 | 98 | 91 | 82 | 72 | 62 | 39 |
| Reference 14 | 97 | 90 | 82 | 73 | 66 | 43 |
| Reference 15 | 100 | 99 | 95 | 94 | 90 | 78 |

TABLE 6b

| Example No. | Recovery [%] 0.17 h | Recovery [%] 0.50 h | Recovery [%] 1.0 h | Recovery [%] 1.5 h | Recovery [%] 2.0 h | Recovery [%] 4.0 h |
|---|---|---|---|---|---|---|
| Example 1 | 95 | 88 | 76 | 65 | 55 | 27 |
| Example 2 | 97 | 90 | 79 | 68 | 59 | 32 | d.4) Plasma and Blood Stability

The plasma and blood stability are investigated in mouse, rat, dog, rabbit, minipig, monkey, and human using 1 ml lithium heparinized plasma or blood with a nominal test concentration of 1000 µg/l at 37° C. for 5 h. At time point 0 h, 0.083 h, 0.25 h, 0.5 h, 1 h, 2 h, 3 h, and 5 h an aliquot of 50 µl is precipitated with 150 µl acetonitrile+1% formic acid, which is supplemented with two internal standards. After vortexing and centrifugation for 10 min. at 1300 g an aliquot of 50 gi supernatant is diluted 1/10 with 10 mM ammonium acetate buffer at pH 3 and measured by LC-MS/

MS. A concentration—time profile is described in Excel and the respective half-life calculation using $t_{1/2}=\ln 2/k$ is done.

d.5) Per-Oxidative Stability

The drug substance is stored under per-oxidative conditions (0.25 mg/ml drug substance in 50% citrate buffer pH 4 containing 3% $H_2O_2$ and 50% tetrahydrofuran, acetonitrile, methanol or citrate buffer pH 4 to improve solubility) at room temperature for 24 h. In addition the same solutions without $H_2O_2$ are prepared and stored at room temperature for 24 h. Additionally, blank solutions are prepared for each stress solution, to unambiguously identify degradation peaks by comparison of the respective chromatograms. After storage, the $H_2O_2$ solutions are quenched with platinum to stop the $H_2O_2$ from further reactions. The solutions before and after storage (including quenching) are directly injected into the HPLC without further workup. For data evaluation, the respective chromatograms are integrated and compared to each other. Depending on the formed amount of organic impurities (<2%, 2-5% or >5%), the stability is described with the descriptors "stable", "slightly unstable" or "unstable".

d.6) Formaldehyde Stability

The drug substance is stored under per-oxidative conditions (0.25 mg/ml drug substance in 50% citrate buffer pH 4 containing 3% $CH_2O$ and 50% tetrahydrofuran, acetonitrile, methanol or citrate buffer pH 4 to improve solubility) at room temperature for 24 h. In addition the same solutions without $CH_2O$ are prepared and stored at room temperature for 24 h. Additionally, blank solutions are prepared for each stress solution, to unambiguously identify degradation peaks by comparison of the respective chromatograms. The solutions before and after storage are directly injected into the HPLC without further workup. For data evaluation, the respective chromatograms are integrated and compared to each other. Depending on the formed amount of organic impurities (<2%, 2-5% or >5%), the stability is described with the descriptors "stable", "slightly unstable" or "unstable".

d.7.) Thermal Stability

The drug substance is stored as a solid at 90° C. for one day and one week and at 60° C. for one week. After storage, the samples are dissolved in tetrahydrofuran with a concentration of 0.25 mg/ml. These solutions are injected into the HPLC. For data evaluation, the respective chromatograms are integrated and compared to each other. Depending on the formed amount of organic impurities (<2%, 2-5% or >5%), the stability is described with the descriptors "stable", "slightly unstable" or "unstable".

e.1.) Solubility

Suspensions of the drug substance up to 12.5 mg/ml are stirred in water, 0.1M HCl, Buffer pH 2, Buffer pH 3, Buffer pH 4, Buffer pH 4.5, Buffer pH 5, Buffer pH 6, Buffer pH 7, Buffer pH 8, Acetonitrile and 0.9% NaCl Solution at 25° C. for 24 h±4 h prior filtration and analysis via HPLC, except the fully dissolved samples, which are indicated with a solubility of ">12500 µg/ml".

For the HPLC analysis, the samples are diluted 1:10 and 1:100 in the solvent, to fit the calibration. Moreover, three standard solutions for the calibration curve are prepared, which have a concentration of 500 µg/ml (5 mg/10 ml), 50 µg/ml (1 mg/20 ml) and 1 µg/ml (0.4 ml of the 50 µg/ml standard/20 ml). All sample and standard solutions are injected into the HPLC in a specific order. The solubility is determined by comparison of the total area of the substance peak in the sample with a calibration curve (external standard).

Also an SST (system suitability test) is performed with the standard solutions, that has to achieve the following requirements:

Min. 6 injections of the same standard must have a variation coefficient of <=2.0%.

Min. 4 injections of the calibration standards must have a precision of <=5.0%.

The intercept of the non linear calibration curve must be <=3.0%.

The calibration curve for the calculation must go through zero.

The calculations of the solubility are performed using the least diluted sample that is within the calibration points.

| The following buffers are used: | | |
|---|---|---|
| pH 2.0 | 30 mM (Citrate) | Fluka 31045 (6.43 g citric acid + 3.58 g NaCl + 0.30 g HCl in 1l water) |
| pH 3.0 | 40 mM (Citrate) | Fluka 31046 (8.47 g citric acid + 3.49 g NaCl + 0.82 g NaOH in 1l water) |
| pH 4.0 | 50 mM (Citrate) | 9.61 g citric acid + 6.00 g NaCl + 62.5 ml 1N NaOH in 1l water |
| pH 4.5 | 50 mM (Acetate) | 2.9 g $NACH_3COO \times 3\ H_2O$ + 1.66 ml glacial acetic acid in 1l water |
| pH 5.0 | 50 mM (Citrate) | 9.61 g citric acid + 6.00 g NaCl + 105 ml 1N NaOH in 1l water |
| pH 6.0 | 50 mM (Citrate) | 9.61 g citric acid + 6.00 g NaCl + 140 ml 1N NaOH in 1l water |
| PH 7.0 | 67 mM (Phosphate) | 3.52 g $KH_2PO_4$ + 7.26 g $Na_2HPO_4 \times 2\ H_2O$ in 1l water |
| pH 8.0 | 67 mM (Phosphate) | 0.34 g $KH_2PO_4$ + 11.43 + 11.43 g $Na_2HPO_4 \times H_2O$ in 1l water |
| 0.9% NaCl | 0.9% NaCl | 9.0 g (NaCl) in 1l water |

Solubility/Stability in Citrate Buffer pH 4

The solubility of the drug substance is visually determined by dissolving 4 mg substance in 50 µl Citrate Buffer pH 4. Then, drug substance is subsequently added until either a concentration of 400 mg/ml is reached or a suspension is created. The solution is observed for seven days to detect potential precipitation. After the seven days the solution is diluted to 10 mg/ml and the stability is investigated.

The stability of the drug substance is tested via HPLC and LC/MS. The assay and degradation are investigated with an external standard. For the test, the sample is diluted to 0.1 mg/ml and two standard solutions are prepared (120 µg/ml and 50 µg/ml). All sample and standard solutions are injected into the HPLC in a specific order. The assay is determined by comparison of the total area of the substance peak to a calibration curve (external standard). The amount of degradation is reported as area % of the whole chromatogram of the sample. Additionally, the sample is measured by LC/MS to determine the degradation products.

e.2.) Solubility 25 mg compound are placed in 2 ml solvent. Depending on the solubility of the compound in the solvent (higher or lower than 12.5 mg/ml), a solution or suspension is formed. This solution or suspension is stirred at 25° C. for 24 h±4 h. Thereafter, the solution or suspension is filtered and the remaining solution is analyzed via HPLC. The solubility is determined by comparison of the total area of the substance peak to a calibration curve (external standard). The amount of degradation is reported as area % of the whole chromatogram of the sample and is used as a descriptor for ester hydrolysis. Solvents tested in the solubility assessment are aqueous buffers (pH range 1 to 8), isotonic saline solution and acetonitrile.

Example 2: 440 mg of the compound of example 2 were placed in 0.5 ml Citrate Buffer. The resulting solution had a volume of approx. 0.9 ml and was stirred at 25° C. for 24 h±4 h. Thereafter, the solution was centrifuged and analyzed via HPLC. The solubility was determined by comparison of the total area of the substance peak to a calibration curve (external standard). The measurements were conducted in triplicates. The solubility of the compound of example 2 in Citrate Buffer pH 4 is >500 mg/ml.

f) CYP Inhibition

The potential of test compounds to inhibit human CYP1A2, CYP2C8, CYP2C9, CYP2D6 and CYP3A4 will be investigated with pooled human liver microsomes as enzyme source and respective standard substrates. Inhibitory effects are determined at 6 concentrations (0.625, 1.25, 2.5, 5, 10, 20 µM) of the test compound and compared with the extent of metabolite formation in the absence of a potential inhibitor. Finally, $IC_{50}$-values are calculated. A standard inhibitor, specifically inhibiting a single CYP isoform, is always included to make sure that results are comparable between series of experiments. Assay Procedure: Incubation of phenacetin, amodiaquine, diclofenac, dextromethorphan, and midazolam with human liver microsomes in the presence of six concentrations of the potential inhibitor. Standard incubation mixtures contained 1 mM NADP, 1 mM EDTA, 5 mM glucose 6-phosphate, 1.5 U/ml glucose 6-phosphate dehydrogenase and 50 mM phosphate buffer (pH 7.4) in a total volume of 200 µl. Test compounds are dissolved in acetonitrile. The 96-well plates are incubated for an appropriate time period at 37° C. and reactions are stopped by addition of 100 µl acetonitrile containing the respective internal standard. Precipitated proteins are removed by centrifugation of the well plate (3000 rpm, 10 min). Supernatants are combined and analyses are performed by LC-MS/MS or RapidFire-MS/MS.

Representative CYP inhibition data from this test are listed in Tables 7a and 7b below:

TABLE 7a

| Reference No. | CYP3A4 IC50 [µM] | CYP1A2 IC50 [µM] | CYP2C8 IC50 [µM] | CYP2C9 IC50 [µM] | CYP2D6 IC50 [µM] |
|---|---|---|---|---|---|
| Reference 9 | 0.37 | >20 | 0.34 | 2.32 | 1.66 |
| Reference 10 | 4.07 | >20 | >20 | >20 | >20 |
| Reference 11 | 6.90 | >20 | >20 | >20 | >20 |
| Reference 14 | >20 | >20 | >20 | >20 | >20 |
| Reference 15 | >20 | >20 | >20 | >20 | >20 |

TABLE 7b

| Example No. | CYP3A4 IC50 [µM] | CYP1A2 IC50 [µM] | CYP2C8 IC50 [µM] | CYP2C9 IC50 [µM] | CYP2D6 IC50 [µM] |
|---|---|---|---|---|---|
| Example 1 | 14.93 | >20 | >20 | >20 | >20 |
| Example 2 | 18.49 | >20 | >20 | >20 | >20 | g) CYP Induction

Human hepatocytes are seeded at a density of ~10 000 cells/384-well in 3D and cultured for one day before compound treatment. Cells are treated with a 1:3 serial dilution of 8 concentrations for two consecutive days with media change every day. After 48 h of compound treatment, cells are lysed and mRNA is prepared by state of the art magnetic beads technique. Following mRNA isolation, cDNA is transcribed directly from the mRNA coated beads and further processed for qPCR. CYP relative expression levels are determined via TaqMan probes by multiplexing of CYP3A4, CYP1A2, Actin and Tubulin. CYP induction is calculated based on the ΔΔCt method and expressed as fold induction over vehicle treated control.

h) Metabolic Stability in Hepatocytes

Metabolic stabilities in hepatocytes are determined by incubating the compounds at 1 µM and at low cell numbers of $1*10^6$ cells/ml to ensure linear kinetics. To minimize the influence of organic solvents in the incubation mixture their content is limited to max. 1% for acetonitrile or max. 0.2% for DMSO. Seven timepoints from the incubation mixture are withdrawn for analysis to define the half-life of the compound from the slope value $t_{1/2}=-0.693/k$. The conversion of the in vitro $t_{1/2}$ (in 10 min.) into intrinsic clearance ($CL'_{intr,hep}$, in L/h/kg) is calculated with the following equation:

$$CL'_{intr,hep} = kV/N \times scaling\ factor$$

$CL'_{intr,hep}$: Intrinsic clearance of the liver to remove drug in the absence of flow limitations and binding to cells or proteins in the blood V=incubation volume (0.25 ml)

N=number of hepatocytes per well ($0.25 \times 10^6$ cells)

The intrinsic clearance is converted into the predicted hepatic clearance ($CL'_{blood,hep,ws}$, in L/h/kg) with the following equation in accordance of the well stirred model:

$$CL'_{blood,hep,ws} = Q_H * CL'_{intr,hep}/(Q_H + CL'_{intr,hep})$$

$Q_H$=hepatic blood flow $CL'_{blood,hep,ws}$: Calculation of hepatic clearance based on the well stirred model. The "well-stirred" model assumes that the liver is a single well-stirred compartment and that the concentration of unbound drug in the emergent blood is in equilibrium with the unbound drug within the liver. The Fmax value ((maximal possible bioavailability) is calculated using the equation:

$$F_{max}\ well\text{-}stirred[\%] = (1-(CL_{blood}\ well\text{-}stirred/Q_H))*100$$

Scaling factors for in vivo intrinsic clearance prediction using different species of hepatocytes are listed below:

| Species | Liver Weight (g liver/kg body weight) | Hepatocyte Concentration ($10^6$ cells/g liver) | Hepatic blood flow ($Q_H$, L/(h · kg)) | Scaling Factor |
|---|---|---|---|---|
| Human | 21 | 110 | 1.32 | 2310.0 |
| Minipig | 24.4 | 124 | 2.6 | 3025.6 |
| Dog | 39 | 110 | 2.1 | 4290.0 |
| Rat | 32 | 110 | 4.2 | 3520.0 |
| Rabbit | 26 | 110 | 2.9 | 2860.0 | i) Protein Binding

For the determination of the protein binding with ultrafiltration, the Centrifree® micropartition system containing filter membranes of 30 kDa pore size are used to separate plasma and protein free ultrafiltrate. The driving force for filtration is applied by centrifugation. Prior to the protein binding studies, the adsorption (recovery) of the test compound to the ultrafiltration device and the ability of the test compound to pass the filter membrane is checked by filtration of the test compound dissolved in plasma and buffer at one concentration. The amount of organic solvent added to the plasma may not exceed 1% of the total incubation volume. After the compound is incubated in potassium EDTA plasma at 2000 µg/l for 15 min., 37° C., and 7% $CO_2$, the Centrifree® micropartition system is centrifuged for 12 min. at 1800 g. The yielded filtrates are precipitated with acetonitrile and diluted for LC-MS/MS measurement. The fraction unbound is calculated in the following way:

$$f_u = \frac{C_u}{C} \cdot 100[\%]$$

where $C$ = total concentration in plasma (or buffer)

$C_u$ = unbound concentration (concentration in the ultrafiltrate)

j) Evaluation of (In Vivo) Pharmacokinetics

To evaluate the pharmacokinetics of test substances in vivo, the substances are dissolved in appropriate formulation vehicles (plasma, mixtures of ethanol, dimethyl sulfoxide, PEG400; physiological based formulation). The test substances are then continuously infused for 10 min. to rats and dogs at low doses of 0.1-2 mg/kg/h. 50 µl blood are drawn at appropriate time points up to 24 h via a catheter (rat) or Vena saphena of the right or left leg (dog) and collected into tubes containing K3-EDTA anticoagulant and 150 µl acetonitrile, which is supplemented with an internal standard, to directly precipitate the blood sample. After centrifugation for 10 min. at 1300 g an aliquot of 50 µl supernatant is diluted 1/10 with 10 mM ammonium acetate buffer at pH 3 and measured by LC-MS/MS. The evaluation of the plasma concentration—time profiles is evaluated with a validated pharmacokinetics evaluation program. Furthermore, it is possible to also retrieve organ-, tissue- and urine samples.

C) Working Examples of Pharmaceutical Compositions

The substances according to the invention can be converted to pharmaceutical preparations as follows:

i.v. Solution:

The compound according to the invention is dissolved at a concentration below saturation solubility in a physiologically acceptable solvent (for example isotonic sodium chloride solution, glucose solution 5% and/or PEG 400 solution 30%). The solution is sterilized by filtration and filled into sterile and pyrogen-free injection containers.

The invention claimed is:

1. 2-(1-Methyl-1H-imidazol-2-yl)ethyl 3-[(5-chlorothiophene-2-carbonyl)amino]-N-{2-ethyl-3-[(3S)-3-hydroxy-2-oxopyrrolidin-1-yl]benzene-1-sulfonyl}-S-alaninate of formula (I)

(I)

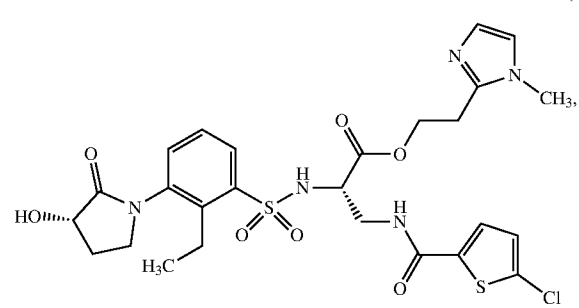

or a salt thereof, a solvate thereof or a solvate of the salt thereof.

2. 2-(1-Methyl-1H-imidazol-2-yl)ethyl 3-[(5-chlorothiophene-2-carbonyl)amino]-N-{2-ethyl-3-[(3S)-3-hydroxy-2-oxopyrrolidin-1-yl]benzene-1-sulfonyl}-S-alaninate according to claim 1 of the formula (I)

(I)

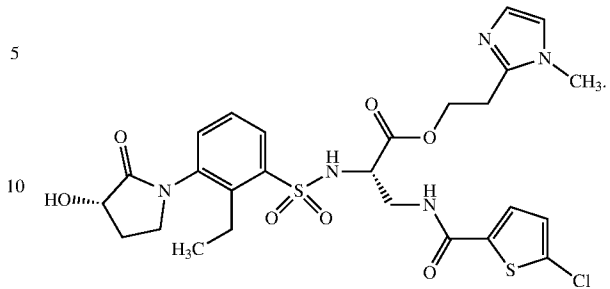

3. The salt of the compound of formula (I) according to claim 1, wherein the salt is a physiologically acceptable salt of the compound of the formula (I).

4. The physiologically acceptable salt of the compound of the formula (I) according to claim 3 selected from the group consisting of:

2-(1-methyl-1H-imidazol-2-yl)ethyl 3-[(5-chlorothiophene-2-carbonyl)amino]-N-{2-ethyl-3-[(3S)-3-hydroxy-2-oxopyrrolidin-1-yl]benzene-1-sulfonyl}-S-alaninate hydrochloride, 2-(1-methyl-1H-imidazol-2-yl)ethyl 3-{[(5-chloro-2-thienyl)carbonyl]amino}-N-({2-ethyl-3-[(3S)-3-hydroxy-2-oxopyrrolidin-1-yl]phenyl}sulfonyl)-S-alaninate sulfate, 2-(1-methyl-1H-imidazol-2-yl)ethyl 3-{[(5-chloro-2-thienyl)carbonyl]amino}-N-({2-ethyl-3-[(3S)-3-hydroxy-2-oxopyrrolidin-1-yl]phenyl}sulfonyl)-S-alaninate methanesulfonate, 2-(1-methyl-1H-imidazol-2-yl)ethyl 3-{[(5-chloro-2-thienyl)carbonyl]amino}-N-({2-ethyl-3-[(3S)-3-hydroxy-2-oxopyrrolidin-1-yl]phenyl}sulfonyl)-S-alaninate 4-methylbenzene-sulfonate, 2-(1-methyl-1H-imidazol-2-yl)ethyl 3-{[(5-chloro-2-thienyl)carbonyl]amino}-N-({2-ethyl-3-[(3S)-3-hydroxy-2-oxopyrrolidin-1-yl]phenyl}sulfonyl)-S-alaninate maleate, 2-(1-methyl-1H-imidazol-2-yl)ethyl 3-{[(5-chloro-2-thienyl)carbonyl]amino}-N-({2-ethyl-3-[(3S)-3-hydroxy-2-oxopyrrolidin-1-yl]phenyl}sulfonyl)-S-alaninate phosphate, 2-(1-methyl-1H-imidazol-2-yl)ethyl 3-{[(5-chloro-2-thienyl)carbonyl]amino}-N-({2-ethyl-3-[(3S)-3-hydroxy-2-oxopyrrolidin-1-yl]phenyl}sulfonyl)-S-alaninate (2R,3R)-tartrate, and 2-(1-methyl-1H-imidazol-2-yl)ethyl 3-{[(5-chloro-2-thienyl)carbonyl]amino}-N-({2-ethyl-3-[(3S)-3-hydroxy-2-oxopyrrolidin-1-yl]phenyl}sulfonyl)-S-alaninate citrate.

5. A process for preparing the compound of the formula (I) or a salt thereof, a solvates thereof or a solvate of the salt thereof according to claim 1, wherein a compound of the formula

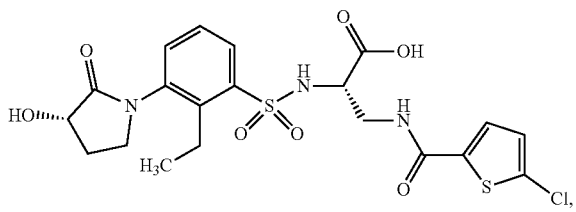

is reacted with a compound of the formula

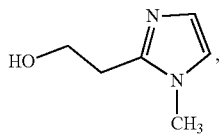

in the presence of a dehydrating agent to give the compound of the formula (I), and the compound of formula (I) is optionally converted with the corresponding (i) solvents and/or (ii) bases or acids into solvates, salts and/or solvates of the salts of the compound of formula (I).

6. A method for the treatment and/or prophylaxis of thrombotic or thromboembolic disorders and/or thrombotic or thromboembolic complications, and/or inflammatory disorders, comprising administering a therapeutic amount of compound of claim 1 to a subject in need thereof.

7. A pharmaceutical formulation comprising the compound of claim 1 and a pharmaceutically suitable excipient.

8. The method of 6, wherein the subject is an animal or a human.

9. The compound of claim 1, wherein the salt is 2-(1-methyl-1H-imidazol-2-yl)ethyl 3-[(5-chlorothiophene-2-carbonyl)amino]-N-{2-ethyl-3-[(3S)-3-hydroxy-2-oxopyrrolidin-1-yl]benzene-1-sulfonyl}-S-alaninate hydrochloride.

10. The compound of claim 1, wherein the salt is 2-(1-methyl-1H-imidazol-2-yl)ethyl 3-{[(5-chloro-2-thienyl)carbonyl]amino}-N-({2-ethyl-3-[(3S)-3-hydroxy-2-oxopyrrolidin-1-yl]phenyl}sulfonyl)-S-alaninate sulfate.

11. The compound of claim 1, wherein the salt is 2-(1-methyl-1H-imidazol-2-yl)ethyl 3-{[(5-chloro-2-thienyl)carbonyl]amino}-N-({2-ethyl-3-[(3S)-3-hydroxy-2-oxopyrrolidin-1-yl]phenyl}sulfonyl)-S-alaninate methanesulfonate.

12. The compound of claim 1, wherein the salt is 2-(1-methyl-1H-imidazol-2-yl)ethyl 3-{[(5-chloro-2-thienyl)carbonyl]amino}-N-({2-ethyl-3-[(3S)-3-hydroxy-2-oxopyrrolidin-1-yl]phenyl}sulfonyl)-S-alaninate 4-methylbenzenesulfonate.

13. The compound of claim 1, wherein the salt is 2-(1-methyl-1H-imidazol-2-yl)ethyl 3-{[(5-chloro-2-thienyl)carbonyl]amino}-N-({2-ethyl-3-[(3S)-3-hydroxy-2-oxopyrrolidin-1-yl]phenyl}sulfonyl)-S-alaninate maleate.

14. The compound of claim 1, wherein the salt is 2-(1-methyl-1H-imidazol-2-yl)ethyl 3-{[(5-chloro-2-thienyl)carbonyl]amino}-N-({2-ethyl-3-[(3S)-3-hydroxy-2-oxopyrrolidin-1-yl]phenyl}sulfonyl)-S-alaninate phosphate.

15. The compound of claim 1, wherein the salt is 2-(1-methyl-1H-imidazol-2-yl)ethyl 3-{[(5-chloro-2-thienyl)carbonyl]amino}-N-({2-ethyl-3-[(3S)-3-hydroxy-2-oxopyrrolidin-1-yl]phenyl}sulfonyl)-S-alaninate (2R,3R)-tartrate.

16. The compound of claim 1, wherein the salt is 2-(1-methyl-1H-imidazol-2-yl)ethyl 3-{[(5-chloro-2-thienyl)carbonyl]amino}-N-({2-ethyl-3-[(3S)-3-hydroxy-2-oxopyrrolidin-1-yl]phenyl}sulfonyl)-S-alaninate citrate.

17. The method of claim 6, wherein the thromboembolic complications is disseminated intravascular coagulation.

* * * * *

UNITED STATES PATENT AND TRADEMARK OFFICE
CERTIFICATE OF CORRECTION

PATENT NO. : 11,912,692 B2
APPLICATION NO. : 18/233031
DATED : February 27, 2024
INVENTOR(S) : Beck et al.

It is certified that error appears in the above-identified patent and that said Letters Patent is hereby corrected as shown below:

In the Specification

In Column 8, Lines 35-36, delete "diisopropylethylamin," and insert -- diisopropylethylamine, --, therefor.
In Column 10, Lines 63-64, delete "systemic inflammatory syndrome (SIRS)," and insert -- systemic inflammatory response syndrome (SIRS), --, therefor.
In Column 12, Line 18, delete "Particular" and insert -- Particularly --, therefor.
In Column 12, Line 30, delete "thromboemboli" and insert -- thromboembolisms --, therefor.
In Column 12, Line 48, delete "therapeutics/vasodilatators," and insert -- therapeutics/vasodilators, --, therefor.
In Column 12, Line 54, delete "temisartan," and insert -- telmisartan, --, therefor.
In Column 12, Line 64, delete "nifedipin" and insert -- nifedipine --, therefor.
In Column 13, Lines 15-16, delete "heparin (UFH), low-molecular-weight heparins (LMW)," and insert -- unfractionated heparin (UFH), low-molecular-weight heparins (LMWHs), --, therefor.
In Column 13, Line 48, delete "thrombomudulin;" and insert -- thrombomodulin; --, therefor.
In Column 15, Line 65, delete "trifluoro acetic acid" and insert -- trifluoroacetic acid --, therefor.
In Column 16, Line 39, delete "bei" and insert -- at --, therefor.
In Column 17, Line 22, delete ""x Na+"" and insert -- "x Na$^+$" --, therefor.
In Column 17, Line 49, delete "multipletts," and insert -- multiplets, --, therefor.
In Column 17, Line 60, delete "02θ" and insert -- °2θ --, therefor.
In Column 18, Line 43, delete "copper(I)iodide" and insert -- copper(I) iodide --, therefor.
In Column 18, Line 67, delete "3H)" and insert -- 3H). --, therefor.
In Column 21, Line 49, delete "([tert" and insert -- {[tert --, therefor.
In Column 21, Line 50, delete "oxy pyrrolidin-2-one" and insert -- oxy}pyrrolidin-2-one --, therefor.
In Column 22, Line 32, delete "sulfurylchoride" and insert -- sulfuryl chloride --, therefor.
In Column 23, Line 61, delete "aqeuous" and insert -- aqueous --, therefor.
In Column 26, Line 55, delete "were were" and insert -- were --, therefor.
In Column 29, Line 11, delete "HNMR." and insert -- $^1$H NMR. --, therefor.
In Column 33, Line 56, delete "fractions" and insert -- fractions were --, therefor.

Signed and Sealed this
Eleventh Day of June, 2024

*Katherine Kelly Vidal*
*Director of the United States Patent and Trademark Office*

CERTIFICATE OF CORRECTION (continued)
U.S. Pat. No. 11,912,692 B2

In Column 39, Line 13, delete "3H)" and insert -- 3H). --, therefor.
In Column 45, Line 34, delete "R," and insert -- $R_t$ --, therefor.
In Column 50, Line 24, delete "[M+H]$^{30}$" and insert -- [M+H]$^+$ --, therefor.
In Columns 49 & 50, in TABLE 1, Line 1, delete "(Example" and insert -- (Examples --, therefor.
In Columns 51 & 52, in TABLE 1-continued, Line 1, delete "(Example" and insert -- (Examples --, therefor.
In Column 51, Line 43, delete "Table" and insert -- Tables --, therefor.
In Column 52, Line 23, delete "Table" and insert -- Tables --, therefor.
In Column 52, Line 28, delete "factor factor" and insert -- factor --, therefor.
In Column 52, Line 56, delete "Table" and insert -- Tables --, therefor.
In Column 56, Line 45, delete "(Octapharm), 10 µL destilled" and insert -- (Octapharma), 10 µL distilled --, therefor.
In Column 56, Line 46, delete "thrombinsubstrate" and insert -- thrombin substrate --, therefor.
In Column 57, Line 29, delete "in in" and insert -- in --, therefor.
In Column 57, Line 46, delete "Laver" and insert -- Layer --, therefor.
In Column 57, Line 56, delete "Xcelligence" and insert -- xCELLigence --, therefor.
In Column 58, Line 3, delete "Xcelligence" and insert -- xCELLigence --, therefor.
In Column 58, Line 19, delete "(NZW)" and insert -- (NZW)) --, therefor.
In Column 58, Line 20, delete "Xylazin" and insert -- Xylazine --, therefor.
In Column 58, Line 21, delete "Thrombos" and insert -- Thrombus --, therefor.
In Column 58, Line 22, delete "arterviovenous" and insert -- arteriovenous --, therefor.
In Column 58, Line 25, delete "extracorporal" and insert -- extracorporeal --, therefor.
In Column 58, Line 32, delete "extracorporal" and insert -- extracorporeal --, therefor.
In Column 59, Line 53, delete "Atropinsulfate (Atropin," and insert -- Atropine sulfate (Atropine, --, therefor.
In Column 59, Line 58, delete "tubus" and insert -- tube --, therefor.
In Column 59, Line 58, delete "Rdsch)" and insert -- Rüsch) --, therefor.
In Column 61, Line 35, delete "system" and insert -- system. --, therefor.
In Column 61, Line 57, delete "manually" and insert -- manual --, therefor.
In Column 62, Line 63, delete "acetonitrile+1%" and insert -- acetonitrile +1% --, therefor.
In Column 62, Line 66, delete "50 gi" and insert -- 50 µl --, therefor.
In Column 64, in Table, Line 9, delete "NACH$_3$OO" and insert -- NaCH$_3$OO --, therefor.
In Column 64, in Table, Line 15, delete "PH" and insert -- pH --, therefor.
In Column 64, in Table, Line 17, delete "11.43 + 11.43 g" and insert -- 11.43 g --, therefor.
In Column 65, Lines 41-42, delete "CYP3A4 IC50 [µM]" and insert -- CYP3A4 IC$_{50}$ [µM] --, therefor.
In Column 65, Lines 41-42, delete "CYP1A2 IC50 [µM]" and insert -- CYP1A2 IC$_{50}$ [µM] --, therefor.
In Column 65, Lines 41-42, delete "CYP2C8 IC50 [µM]" and insert -- CYP2C8 IC$_{50}$ [µM] --, therefor.
In Column 65, Lines 41-42, delete "CYP2C9 IC50 [µM]" and insert -- CYP2C9 IC$_{50}$ [µM] --, therefor.
In Column 65, Lines 41-42, delete "CYP2D6 IC50 [µM]" and insert -- CYP2D6 IC$_{50}$ [µM] --, therefor.
In Column 65, Lines 51-52, delete "CYP3A4 IC50 [µM]" and insert -- CYP3A4 IC$_{50}$ [µM] --, therefor.
In Column 65, Lines 51-52, delete "CYP1A2 IC50 [µM]" and insert -- CYP1A2 IC$_{50}$ [µM] --, therefor.
In Column 65, Lines 51-52, delete "CYP2C8 IC50 [µM]" and insert -- CYP2C8 IC$_{50}$ [µM] --, therefor.
In Column 65, Lines 51-52, delete "CYP2C9 IC50 [µM]" and insert -- CYP2C9 IC$_{50}$ [µM] --, therefor.
In Column 65, Lines 51-52, delete "CYP2D6 IC50 [µM]" and insert -- CYP2D6 IC$_{50}$ [µM] --, therefor.
In Column 66, Line 35, delete "((maximal" and insert -- (maximal --, therefor.

CERTIFICATE OF CORRECTION (continued)
U.S. Pat. No. 11,912,692 B2

In the Claims

In Column 69, Line 36, in Claim 8, delete "method of 6," and insert -- method of claim 6, --, therefor.